US008791111B2

(12) United States Patent
Schiemann et al.

(10) Patent No.: US 8,791,111 B2
(45) Date of Patent: Jul. 29, 2014

(54) PIPERIDINE AND PIPERAZINE DERIVATIVES

(75) Inventors: Kai Schiemann, Seeheim-Jugenheim (DE); Melanie Schultz, Darmstadt (DE); Andree Blaukat, Schriesheim (DE); Ingo Kober, Gross-Gerau (DE)

(73) Assignee: Merck Patent GmbH, Darmstadt (DE)

( * ) Notice: Subject to any disclaimer, the term of this patent is extended or adjusted under 35 U.S.C. 154(b) by 196 days.

(21) Appl. No.: 12/681,440

(22) PCT Filed: Sep. 19, 2008

(86) PCT No.: PCT/EP2008/007893
§ 371 (c)(1),
(2), (4) Date: Apr. 2, 2010

(87) PCT Pub. No.: WO2009/046841
PCT Pub. Date: Apr. 16, 2009

(65) Prior Publication Data
US 2010/0222341 A1     Sep. 2, 2010

(30) Foreign Application Priority Data
Oct. 5, 2007 (DE) .......................... 10 2007 047 737

(51) Int. Cl.
*A61K 31/535* (2006.01)
*A61K 31/497* (2006.01)
*C07D 403/06* (2006.01)
*C07D 413/06* (2006.01)

(52) U.S. Cl.
USPC ................... 514/233.8; 514/254.04; 544/364; 544/368

(58) Field of Classification Search
USPC ................... 514/233.8, 254.04; 544/364, 368
See application file for complete search history.

(56) References Cited

U.S. PATENT DOCUMENTS

| 4,960,778 A * | 10/1990 | Lesieur et al. ........... 514/252.19 |
| 5,698,553 A | 12/1997 | Prucher et al. |
| 6,319,916 B1 * | 11/2001 | Goto et al. ............... 514/211.09 |
| 6,407,122 B1 | 6/2002 | Mantegani et al. |
| 6,969,711 B2 * | 11/2005 | Shibuya et al. ............... 514/218 |

FOREIGN PATENT DOCUMENTS

| EP | 0 709 384 A1 | 5/1996 |
| EP | 1 254 661 A1 | 11/2002 |
| JP | 60 130573 A | 7/1985 |
| WO | WO 98/18793 A1 | 5/1998 |
| WO | WO 99/28318 A1 | 6/1999 |
| WO | WO 00/00197 A1 | 1/2000 |
| WO | WO 02/30422 | 4/2002 |
| WO | WO 02/085352 A1 | 10/2002 |

OTHER PUBLICATIONS

Albers et al. J.Med. Chem. vol. 54, pp. 4619-4626 (2011).*
Osman et al. Indian Journal of Chemistry, Section B, vol. 19B(8), p. 707-709 (1980).*
Barbayianni et al. Expert Opin.Ther. Patents, vol. 23(9), pp. 1123-1132 (2013).*
Gierse et al. the Journal of Pharmacology and Experimental Therapeutics, vol. 334, pp. 310-317 (2010).*
Cancer Drug Design and Discovery, Neidle, Stephen,ed. (Elsevier/Academic Press), pp. 427-431 (2008).*
"International Search Report," International Application No. PCT/EP2008/007893, Date of Completion Feb. 23, 2009, Date of Mailing Mar. 26, 2009, 5 pages.
Leibrock J. et al, "A New Eliprodil Analogue With Higher Affinity for the N-Methyl-D-Aspartate (NMDA) Receptor," Jun. 1, 1997, Bd. 52, Nr.. ISSN:0031-7144, XP001093620.
Yous, Said; Lebegue, Nicolas; Poupaert, Jacques-Henry; Chavatte, Philippe; Berthelot, Pascal: "Lipid-lowering properties of 6-benzoyl-2(3H)-benzothiazolone and structurally related compounds," Journal of Enzme Inhibition and Medicinal Chemistry, Bd.20, 2005, Seiten 525-592, XP008102609.
Database Registry, Chemical Abstracts Servie, Columbus, Ohio, US; RN 1026456-19-8 XP002516273, entered into STN on Jun. 8, 2008.
Database Registry, Chemical Abastacts Service, Columbus Ohio, US; RN 732947-29-4 XP002518095, enter into STN on Aug. 25, 2004.

* cited by examiner

*Primary Examiner* — James O Wilson
*Assistant Examiner* — Ebenezer O Sackey
(74) *Attorney, Agent, or Firm* — Millen, White, Zelano & Branigan, P.C.

(57) ABSTRACT

Compounds of the formula (I), in which $R^1$, $R^2$, $R^3$, D, G, Q and W have the meanings indicated in Claim (1), can and be employed for the treatment of tumors.

26 Claims, No Drawings

PIPERIDINE AND PIPERAZINE DERIVATIVES

BACKGROUND OF THE INVENTION

The invention was based on the object of finding novel compounds having valuable properties, in particular those which can be used for the preparation of medicaments.

The present invention relates to compounds and to the use of compounds for the treatment of diseases which are accompanied by an increase in the lysophosphatidic acid level, furthermore to pharmaceutical compositions which comprise these compounds.

In detail, the present invention relates to compounds of the formula I, which preferably inhibit one or more enzymes which regulate and/or modulate the lysophosphatidic acid (LPA) level, to compositions which comprise these compounds, and to processes for the use thereof for the treatment of diseases and complaints, such as angiogenesis, cancer, tumour formation, growth and propagation, arteriosclerosis, ocular diseases, choroidal neo-vascularisation and diabetic retinopathy, inflammatory diseases, arthritis, neurodegeneration, restenosis, wound healing or transplant rejection. In particular, the compounds according to the invention are suitable for the therapy or prophylaxis of cancer diseases.

Autotaxin (ATX) is an enzyme which is responsible for the increase in the lysophosphatidic acid level in ascites and plasma (Xu et al. 1995, Clinical Cancer Research Vol. 1, page 1223 and Xu et al. 1995, Biochem. J. Vol-309, page 933). ATX converts lysophatidylcholine (LPC) into lysophosphatidic acid (Tokumura et al. 2002, J. Biol. Chem., Vol 277, page 39436 and Umezu-Gozo et al. 2002, J. Biol. Chem., Vol. 158, page 227) LPA is an intercellular lipid mediator which influences a multiplicity of biological and biochemical processes, such as, for example, smooth muscle contraction, thrombocyte aggregation and apoptosis (Tigyi et al. 2003 Prog. Lipid Res. Vol 42, page. 498 and Mills et al. 2003 Nat. Rev. Cancer Vol. 3, page 582 and Lynch et al. 2001 Prost. Lipid Med. Vol. 64, page 33). In addition, LPA can be found in increased concentrations in plasma and ascites fluid from ovarian cancer patients in the early and late phase. LPA plays a role there in tumour cell proliferation and invasion thereof into neighbouring tissue, which can result in metastasisation (Xu et al. 1995, Clinical Cancer Research Vol. 1, page 1223 and Xu et al. 1995, Biochem. J. Vol-309, page 933). These biological and phatobiological processes are switched on by the activation by LPA of G-protein-coupled receptors (Contos et al. 2000, Mol. Pharm. Vol 58, page. 1188).

For this reason, it is desirable to lower the LPA level for the treatment of tumour patients. This can be achieved by the inhibition of enzymes which are involved in LPA biosynthesis, such as, for example, autotaxin (ATX, Sano et al. 2002, J. Biol. Chem. Vol. 277, page 21197 and Aoki et al. 2003, J. Biol. Chem. Vol. 277 page 48737). Autotaxin belongs to the enzyme family of the nucleotides pyrophosphatases and phosphodiesterases (coding et al. 1998, Immunol. Rev. Vol. 161, page 11) and represents an important starting point in antitumour therapy (Mills et al. 2003 Nat. Rev. Cancer Vol. 3, page 582 and Goto et al. 2004 J. Cell. Biochem. Vol. 92, page 1115) since it is expressed to an increased extent in tumours and causes tumour cell proliferation and invasion thereof into neighbouring tissue, which can result in metastasisation (Nam et al. 2000, Oncogene, Vol. 19 page 241). In addition, autotaxin together with other angiogenetic factors causes blood vessel formation in the course of angiogenesis (Nam et al. 2001, Cancer Res. Vol. 61 page. 6938). Angiogenesis is an important process in tumour growth, which ensures supply of the tumour with nutrients. For this reason, inhibition of angiogenesis is an important starting point in cancer and tumour therapy, in which it is intended to starve the tumour (Folkman, 2007, Nature Reviews Drug Discovery Vol. 6, page 273-286).

Surprisingly, it has been found that the compounds according to the invention cause specific inhibition of the enzyme family of the nucleotides pyrophosphatases and phosphodiesterases, in particular autotaxin. The compounds according to the invention preferably exhibit an advantageous biological activity, which can easily be detected in the assays described, for example, herein. In assays of this type, the compounds according to the invention preferably exhibit and cause an inhibiting effect, which is usually documented by $IC_{50}$ values in a suitable range, preferably in the micromolar range and more preferably in the nanomolar range.

In general, all solid and non-solid tumours can be treated with the compounds of the formula I, such as, for example, monocytic leukaemia, brain, urogenital, lymphatic system, stomach, laryngeal and lung carcinoma, including lung adenocarcinoma and small-cell lung carcinoma. Further examples include prostate, pancreatic and breast carcinoma.

As discussed herein, effects of the compound according to the invention are relevant for various diseases. Accordingly, the compounds according to the invention are useful in the prophylaxis and/or treatment of diseases which are influenced by inhibition of one or more nucleotides pyrophosphatases and/or phosphodiesterases, in particular autotaxin.

The present invention therefore relates to compounds according to the invention as medicaments and/or medicament active ingredients in the treatment and/or prophylaxis of the said diseases and to the use of compounds according to the invention for the preparation of a pharmaceutical agent for the treatment and/or prophylaxis of the said diseases, and also to a method for the treatment of the said diseases comprising the administration of one or more compounds according to the invention to a patient in need of such administration.

It can be shown that the compounds according to the invention have an advantageous action in a xenotransplant tumour model.

The host or patient can belong to any mammalian species, for example a primate species, in particular humans; rodents, including mice, rats and hamsters; rabbits; horses, cattle, dogs, cats, etc. Animal models are of interest for experimental investigations, where they provide a model for the treatment of a human disease.

The sensitivity of a certain cell to treatment with the compounds according to the invention can be determined by testing in vitro. Typically, a culture of the cell is combined with a compound according to the invention at various concentrations for a time which is sufficient to enable the active agents to induce cell death or to inhibit migration, usually between approximately one hour and one week. For testing in vitro, cultivated cells from a biopsy sample can be used. The viable cells remaining after the treatment are then counted.

The dose varies depending on the specific compound used, the specific disease, the patient status, etc. Typically, a therapeutic dose is sufficient to considerably reduce the undesired cell population in the target tissue, while the viability of the patient is maintained. The treatment is generally continued until a considerable reduction has occurred, for example at least about a 50% reduction in the cell burden, and can be continued until essentially no undesired cells can be detected in the body.

PRIOR ART

Compounds which are capable of inhibiting autotaxin are described in Peng et al. Bioorganic & Medicinal Chemistry (Letters 17, 2007, page 1634-1640). The compounds described therein are lipid analogues, which do not have any structural features in common with the compounds according to the invention.

Other heterocyclic derivatives are described in WO 2002085352, WO 2002030422, EP 1002535, WO 9818793, EP 385848, FR 2637286, WO 2005097782, EP 709384, EP 396282, EP 49203.

SUMMARY OF THE INVENTION

The invention relates to compounds of the formula I

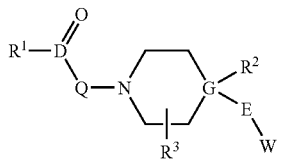

in which
$R^1$ denotes a bicyclic unsaturated or aromatic heterocycle having 1 to 4 N, O and/or S atoms, which may be unsubstituted or mono-, di- or trisubstituted by A, Hal, $NR_2$, $(CR_2)_nCN$, $OR^5$ and/or =O (carbonyl oxygen),
D denotes C or S,
G denotes N or C,
if G=N:
$R^2$ is absent,
if G=C:
$R^2$ denotes H or $Ar^1$
or also, together with the C atom to which $R^2$ is bonded and with E-W, denotes a spirocyclic radical selected from the group

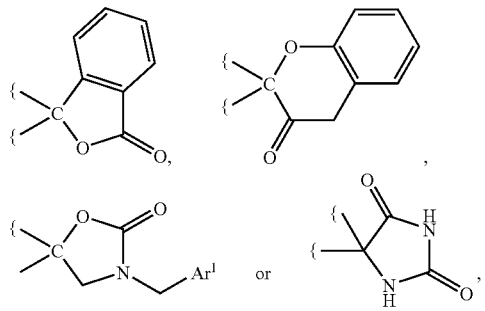

Q denotes unbranched or branched alkylene having 1, 2, 3 or 4 C atoms, in which 1-5H atoms may be replaced by A, $(CR_2)_n[X(CR_2)_n]_p$—Y, F and/or Cl,
$R^3$ denotes H, A, Ar, OR, SR, $NR_2$, Hal, $NO_2$, CN or $(CR_2)_n[X(CR_2)_n]_p$—Y,
X denotes O, NR or $CR_2$,
Y denotes OR or $NR_2$,
$R^5$ denotes H or unbranched or branched alkyl having 1, 2, 3, 4, 5 or 6 C atoms, in which 1-7H atoms may be replaced by F and/or Cl,
E denotes $COO(CR_2)_n$, $COO(CRR^4)$, $CO(CR_2)_mO$, $CONH(CR_2)_n$, $C(=S)NH(CR_2)_n$, $S(O)_qNH(CR_2)_n$, $S(O)_q(CR_2)_n$, $CO(CR_2)_n$, $(CR_2)_n$, $CO(CR_2)_mO(CR_2)_n$, $CO(CR_2)_mNH(CR_2)_n$, $CO(CH_2)_nCO$, $COCHR^6CHR^7$, $C(=S)O(CR_2)_n$, $CO(CRR^4)(CR_2)_n$, $COO(CRR^4)$, $(CRR^4)(CR_2)_n$, $S(O)_q$ $CR=CR$, $COCR=CR$, $(CR_2)_mCO$, $CONH(CR_2)_mCRR^4$ or $(CR_2)_mCONR$, $R^4$ denotes $COOR^5$, $Ar^1$, $NRCOOR^8$, $(CR_2)_nNR_2$ or NRCOOA,
$R^6$, $R^7$ together denote $(CH_2)_{1-4}$,
$R^8$ denotes phenyl, naphtyl or fuorenyl,
R denotes H or unbranched or branched alkyl having 1, 2, 3, 4, 5 or 6 C atoms,
W denotes Ar or Het,
Ar denotes phenyl, indanyl, naphthyl or biphenyl, each of which is unsubstituted or mono-, di-, tri-, tetra- or penta-substituted by Hal, A, $(CR_2)_nOR$, $O(CR_2)_nAr^1$, $(CR_2)_nNR_2$, SR, $NO_2$, CN, COOR, $CONR_2$, NRCOA, $NRSO_2A$, $SO_2NR_2$, $S(O)_qA$, CO-Het, $(CR_2)_nHet$, $O(CR_2)_nNR_2$, $O(CR_2)_nHet$, NHCOOA, $NHCONR_2$, $NHCOO(CR_2)_nNR_2$, $NHCOO(CR_2)_nHet$, $CR^5=CR^5Ar^1$, $SO_2Het$, $NHCONH(CR_2)_nNR_2$, $NHCONH(CR_2)_nHet$, $OCONH(CR_2)_nNR_2$, $OCONH(CR_2)_nHet$, $CONR(CR_2)_nNR_2$, $CONR(CR_2)_nHet$ and/or COA,
Het denotes a mono-, bi- or tricyclic saturated, unsaturated or aromatic heterocycle having 1 to 4 N, O and/or S atoms, which may be unsubstituted or mono-, di- or trisubstituted by Hal, A, $(CR_2)_nAr^1$, $O(CR_2)_nAr^1$, $(CR_2)_nOR$, $(CR_2)_nNR_2$, SR, $NO_2$, CN, COOR, $CONR_2$, NRCOA, $NRSO_2A$, $SO_2NR_2$, $S(O)_qA$, $CO-Het^1$, $(CR_2)_nHet^1$, $O(CR_2)_nNR_2$, $O(CR_2)_nHet^1$, NHCOOA, $NHCONR_2$, $NHCOO(CR_2)_n$ $NR_2$, $NHCOO(CR_2)_nHet^1$, $NHCONH(CR_2)_nNR_2$, $NHCONH(CR_2)_nHet^1$, $OCONH(CR_2)_nNR_2$, $OCONH(CR_2)_nHet^1$, $CO-Het^1$, CHO, COA, =S, =NH, =NA and/or =O (carbonyl oxygen),
$Het^1$ denotes a monocyclic saturated heterocycle having 1 to 2 N and/or O atoms, which may be mono- or disubstituted by A, OA, OH, Hal and/or =O (carbonyl oxygen),
$Ar^1$ denotes phenyl which is unsubstituted or mono-, di-, tri-, tetra- or pentasubstituted by Hal, CN, A and/or $(CR_2)_nOR$,
A denotes unbranched or branched alkyl having 1-10 C atoms, in which 1-7H atoms may be replaced by OR, CN, $NR_2$, F and/or Cl and/or in which one or two non-adjacent $CH_2$ groups may be replaced by O, NH, S, SO, $SO_2$ and/or by CH=CH groups,
or
cyclic alkyl having 3-7 C atoms,
m denotes 1, 2, 3, 4, 5 or 6,
n denotes 0, 1, 2, 3, 4, 5, 6, 7 or 8,
p denotes 1, 2, 3, 4, 5 or 6,
q denotes 0, 1 or 2,
Hal denotes F, Cl, Br or I,
and pharmaceutically usable tautomers, salts and stereoisomers thereof, including mixtures thereof in all ratios.

The invention also relates to the optically active forms (stereoisomers), the enantiomers, the racemates, the diastereomers and the hydrates and solvates of these compounds. The term solvates of the compounds is taken to mean adductions of inert solvent molecules onto the compounds which form owing to their mutual attractive force. Solvates are, for example, mono- or dihydrates or alcoholates.

Compounds of the formula I are also taken to mean the solvates and derivatives.

Pharmaceutically usable derivatives are taken to mean, for example, the salts of the compounds according to the invention and also so-called prodrug compounds.

Prodrug derivatives are taken to mean compounds of the formula I which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:
improved treatment, healing, prevention or elimination of a disease, syndrome, condition, complaint, disorder or side effects or also the reduction in the advance of a disease, complaint or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The invention relates to the compounds of the formula I and salts thereof and to a process for the preparation of compounds of the formula I according to the patent claims and pharmaceutically usable salts and stereoisomers thereof, characterised in that
a) a compound of the formula II

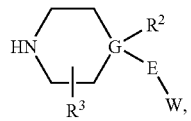

II in which $R^2$, $R^3$, G, E and W have the meanings indicated in Claim 1,
is reacted with a compound of the formula III

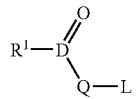

III in which
$R^1$, D and Q have the meanings indicated in Claim 1, and
L denotes Cl, Br, I or a free or reactively functionally modified OH group,
or
b) a compound of the formula IV

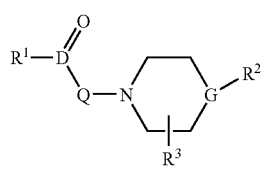

IV in which
$R^1$, $R^2$, $R^3$, D and Q have the meanings indicated in Claim 1 and G=N is reacted with a compound of the formula V

L-E-W   V in which
E and W have the meanings indicated in Claim 1, and
L denotes Cl, Br, I or a free or reactively functionally modified OH group,
and/or a base or acid of the formula I is converted into one of its salts.

A denotes alkyl and is preferably unbranched (linear) or branched, and has 1, 2, 3, 4, 5, 6, 7, 8, 9 or 10 C atoms. Alkyl preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl.

Alkyl very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl. Alkyl also denotes cycloalkyl.

Cycloalkyl preferably denotes cyclopropyl, cyclobutyl, cylopentyl, cyclohexyl or cycloheptyl.

$R^1$ preferably denotes a bicyclic unsaturated or aromatic heterocycle selected from the group

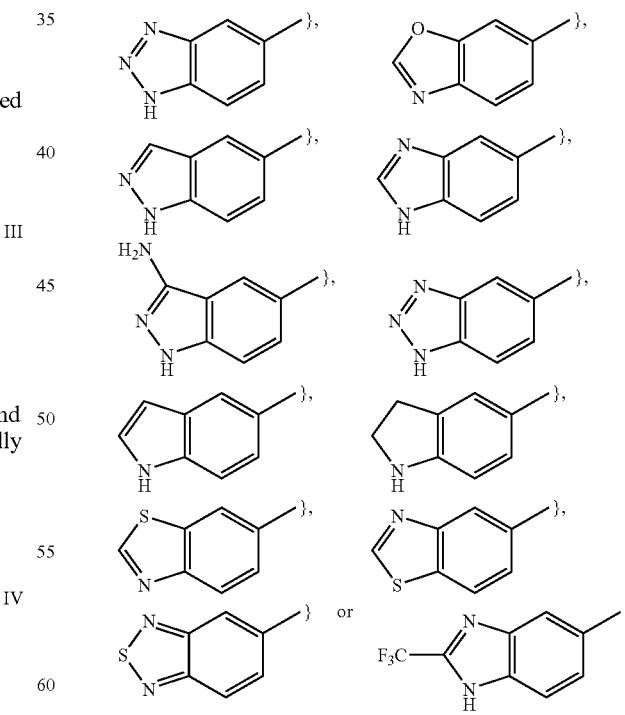

which may be unsubstituted or mono-, di- or trisubstituted by A, Hal, $NR_2$, $(CR_2)_n CN$, $OR^5$ and/or =O (carbonyl oxygen).

$R^1$ particularly preferably denotes a bicyclic unsaturated or aromatic heterocycle selected from the group

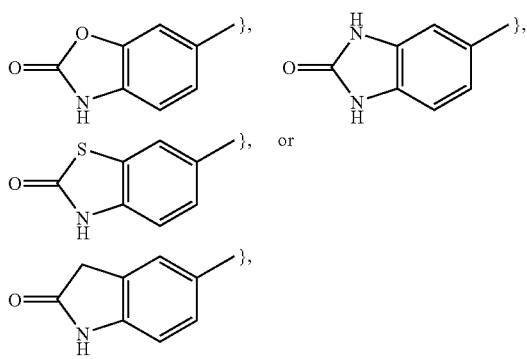

which may additionally be mono- or disubstituted by A, Hal, $NR_2$, $(CR_2)_nCN$ and/or $OR^5$.

$R^2$ preferably denotes
if G=N: absent,
if G=C: H.

$R^3$ preferably denotes H.

Q preferably denotes methylene or ethylene.

$R^5$ preferably denotes H or unbranched or branched alkyl having 1, 2, 3 or 4 C atoms, in which 1-5 H atoms may be replaced by F.

D preferably denotes C.

R preferably denotes H, methyl or ethyl, particularly preferably H.

Ar preferably denotes phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-methoxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl, 2,5-dimethyl-4-chlorophenyl, naphthyl or biphenyl.

Ar furthermore preferably denotes phenyl, indanyl, naphthyl or biphenyl, each of which is unsubstituted or mono-, di-, tri-, tetra- or pentasubstituted by Hal, A, $(CR_2)_nOR$, $O(CR_2)_nAr^1$, $(CR_2)_nNR_2$, SR, $NO_2$, CN, COOR, $CONR_2$, NRCOA, $NRSO_2A$, $SO_2NR_2$, $S(O)_qA$, CO-Het, $(CR_2)_n$Het, $O(CR_2)_n NR_2$, $CR^5=CR^5Ar^1$ and/or $SO_2$Het.

$Ar^1$ preferably denotes phenyl which is unsubstituted or mono-, di-, tri-, tetra- or pentasubstituted by Hal, CN, A and/or $(CR_2)_nOR$.

Irrespective of further substitutions, Het denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4-5-yl, 2,1,3-benzoxadiazol-5-yl or dibenzofuranyl.

The heterocyclic radicals may also be partially or fully hydrogenated. Irrespective of further substitutions, Het can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-,-2-,-3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl, 2,3-dihydro-2-oxofuranyl, 3,4-dihydro-2-oxo-1H-quinazolinyl, 2,3-dihydrobenzoxazolyl, 2-oxo-2,3-dihydrobenzoxazolyl, 2,3-dihydrobenzimidazolyl, 1,3-dihydroindole, 2-oxo-1,3-dihydroindole or 2-oxo-2,3-dihydrobenzimidazolyl.

Het furthermore preferably denotes a mono- or bicyclic saturated, unsaturated or aromatic heterocycle having 1 to 3 N, O and/or S atoms, which may be unsubstituted or mono- or disubstituted by Hal, A, $(CR_2)_nAr^1$ and/or =O (carbonyl oxygen) substituted piperidinyl, piperazinyl, pyrrolidinyl, morpholinyl, furanyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, indolyl, benzo-1,3-dioxolyl, indazolyl, 2,3-dihydro-benzo-1,4-dioxinyl, chromanyl, thiazolidinyl, isoindolyl, tetrahydrofuranyl, carbazolyl, benzo[b]thiophenyl or benzo-2,1,3-thiadiazolyl.

$Het^1$ preferably denotes pyrrolidine, piperidine, piperazine or morpholine, each of which is unsubstituted or mono- or disubstituted by A and/or =O (carbonyl oxygen).

Hal preferably denotes F, Cl or Br, but also I, particularly preferably F or Cl.

The indices have the following preferred meanings
m 1, 2, 3 or 4,
n 0, 1, 2, 3 or 4, p 1, 2, 3 or 4,
q 0, 1 or 2.

Throughout the invention, all radicals which occur more than once, such as, for example, R, may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above.

Some preferred groups of compounds may be expressed by the following sub-formulae Ia to Ip, which conform to the formula I and in which the radicals not designated in greater detail have the meaning indicated for the formula I, but in which in Ia $R^1$ denotes a bicyclic unsaturated or aromatic heterocycle selected from the group

[structures shown]

which may be unsubstituted or mono-, di- or trisubstituted by A, Hal, $NR_2$, $(CR_2)_nCN$, $OR^5$ and/or =O (carbonyl oxygen);

in Ib $R^1$ denotes a bicyclic unsaturated or aromatic heterocycle selected from the group

[structures shown]

which may additionally be mono- or disubstituted by A, Hal, $NR_2$, $(CR_2)_nCN$ and/or $OR^5$;

in Ic if G=N:
  $R^2$ is absent,
  if G=C:
  $R^2$ denotes H;
in Id $R^3$ denotes H;
in Ie Q denotes unbranched or branched methylene, ethylene, propylene or butylene;
in If $R^5$ denotes H or unbranched or branched alkyl having 1, 2, 3 or 4 C atoms, in which 1-5H atoms may be replaced by F;
in Ig D denotes C;
in Ih R denotes H, methyl or ethyl;
in Ii R denotes H;
in Ij Ar denotes phenyl, indanyl, naphthyl or biphenyl, each of which is unsubstituted or mono-, di-, tri-, tetra- or pentasubstituted by Hal, A, $(CR_2)_nOR$, $O(CR_2)_nAr^1$, $(CR_2)_nNR_2$, SR, $NO_2$, CN, COOR, $CONR_2$, NRCOA, $NRSO_2A$, $SO_2NR_2$, $S(O)_qA$, CO-Het, $(CR_2)_nHet$, $O(CR_2)_nNR_2$, $CR^5=CR^5Ar^1$ and/or $SO_2Het$;
in Ik Het denotes a mono- or bicyclic saturated, unsaturated or aromatic heterocycle having 1 to 3 N, O and/or S atoms, which may be unsubstituted or mono- or disubstituted by Hal, A, $Ar^1$ and/or =O (carbonyl oxygen);
in Il Het denotes piperidinyl, piperazinyl, pyrrolidinyl, morpholinyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, indolyl, benzo-1,3-dioxolyl, indazolyl, 2,3-dihydrobenzo-1,4-dioxinyl, chromanyl or benzo-2,1,3-thiadiazolyl, each of which is unsubstituted or mono- or disubstituted by Hal, A, $Ar^1$ and/or =O (carbonyl oxygen);
in Im A denotes unbranched or branched alkyl having 1-10 C atoms, in which 1-7H atoms may be replaced by F and/or Cl;
in In m denotes 1, 2, 3 or 4,
  n denotes 0, 1, 2, 3 or 4,
  p denotes 1, 2, 3 or 4,
  q denotes 0, 1 or 2;
in Io $R^1$ denotes a bicyclic unsaturated or aromatic heterocycle selected from the group

[structures shown]

-continued

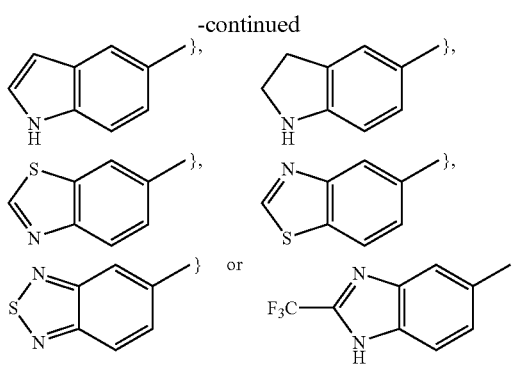

which may be unsubstituted or mono-, di- or trisubstituted by A, Hal, NR$_2$, (CR$_2$)$_n$CN, OR$^5$ and/or =O (carbonyl oxygen),
D denotes C,
G denotes N or C,
if G=N:
R$^2$ is absent,
if G=C:
R$^2$ denotes H or Ar$^1$
or also, together with the C atom to which R$^2$ is bonded and with E-W, denotes a spirocyclic radical selected from the group

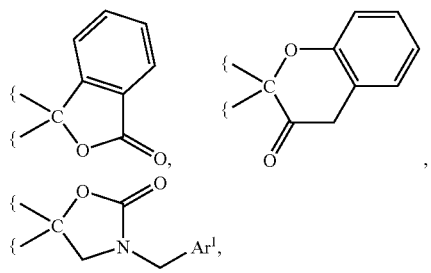

Q denotes unbranched or branched methylene, ethylene, propylene or butylene,
R$^3$ denotes H,
R$^5$ denotes H or unbranched or branched alkyl having 1, 2, 3 or 4 C atoms, in which 1-5H atoms may be replaced by F,
E denotes COO(CR$_2$)$_n$, COO(CRR$^4$), CO(CR$_2$)$_m$O, CONH(CR$_2$)$_n$, S(O)$_q$(CR$_2$)$_n$, CO(CR$_2$)$_n$, (CR$_2$)$_n$, CO(CR$_2$)$_m$O(CR$_2$)$_p$, CO(CR$_2$)$_m$NH(CR$_2$)$_p$, C(=S)O (CR$_2$)$_n$, CO(CRR$^4$)(CR$_2$)$_m$, COO(CRR$^4$), (CRR$^4$)(CR$_2$)$_n$, S(O)$_q$CR=CR, COCR=CR, (CR$_2$)$_m$CO or (CR$_2$)$_m$CONR,
R$^4$ denotes COOR$^5$, Ar$^1$, (CR$_2$)$_n$NR$_2$ or NRCOOA,
R denotes H or unbranched or branched alkyl having 1, 2, 3, 4, 5 or 6 C atoms,
W denotes Ar or Het,
Ar denotes phenyl, indanyl, naphthyl or biphenyl, each of which is unsubstituted or mono-, di-, tri-, tetra- or pentasubstituted by Hal, A, (CR$_2$)$_n$OR, O(CR$_2$)$_n$Ar$^1$, (CR$_2$)$_n$NR$_2$, SR, NO$_2$, CN, COOR, CONR$_2$, NRCOA, NRSO$_2$A, SO$_2$NR$_2$, S(O)$_q$A, CO-Het, (CR$_2$)$_n$Het, O(CR$_2$)$_n$NR$_2$, CR$^5$=CR$^5$Ar$^1$ and/or SO$_2$Het,
Het denotes a mono- or bicyclic saturated, unsaturated or aromatic heterocycle having 1 to 3 N, O and/or S atoms, which may be unsubstituted or mono- or disubstituted by Hal, A, Ar$^1$ and/or =O (carbonyl oxygen), Ar$^1$ denotes phenyl which is unsubstituted or mono-, di-, tri-, tetra- or pentasubstituted by Hal, CN, A and/or (CR$_2$)$_n$OR,
A denotes unbranched or branched alkyl having 1-10 C atoms, in which 1-7H atoms may be replaced by F and/or Cl,
m denotes 1, 2, 3 or 4,
n denotes 0, 1, 2, 3 or 4,
p denotes 1, 2, 3 or 4,
q denotes 0, 1 or 2,
Hal denotes F, Cl, Br or I;
in Ip R$^1$ denotes a bicyclic unsaturated or aromatic heterocycle selected from the group

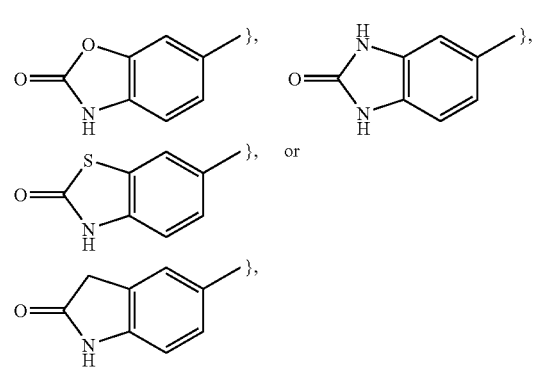

which may additionally be mono- or disubstituted by A, Hal, NR$_2$, (CR$_2$)$_n$CN and/or OR$^5$,
D denotes C,
G denotes N or C,
if G=N:
R$^2$ is absent,
if G=C:
R$^2$ denotes H or Ar$^1$
or also, together with the C atom to which R$^2$ is bonded and with E-W, a spirocyclic radical selected from the group

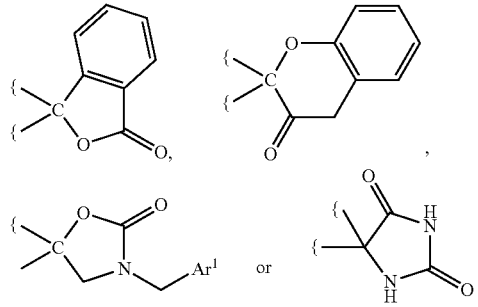

Q denotes methylene, ethylene, propylene or butylene,
R$^3$ denotes H,
R$^5$ denotes H or unbranched or branched alkyl having 1, 2, 3 or 4 C atoms, in which 1-5H atoms may be replaced by F,
E denotes COO(CR$_2$)$_n$, COO(CRR$^4$), CO(CR$_2$)$_m$O, CONH(CR$_2$)$_n$, S(O)$_q$(CR$_2$)$_n$, CO(CR$_2$), (CR$_2$)$_n$, CO(CR$_2$)$_m$O(CR$_2$)$_p$, CO(CR$_2$)$_m$NH(CR$_2$)$_p$, C(=S)O (CR$_2$)$_n$, CO(CRR$^4$)(CR$_2$)$_m$, COO(CRR$^4$), (CRR$^4$)(CR$_2$)$_n$, S(O)$_q$CR=CR, COCR=CR, (CR$_2$)$_m$CO or (CR$_2$)$_m$CONR, $R^4$ denotes $COOR^5$, $Ar^1$, $(CR_2)_nNR_2$ or NRCOOA,
R denotes H, methyl or ethyl,
W denotes Ar or Het,
Ar denotes phenyl, indanyl, naphthyl or biphenyl, each of which is unsubstituted or mono-, di-, tri-, tetra- or pentasubstituted by Hal, A, $(CR_2)_nOR$, $O(CR_2)_nAr^1$, $(CR_2)_nNR_2$, SR, $NO_2$, CN, COOR, $CONR_2$, NRCOA, $NRSO_2A$, $SO_2NR_2$, $S(O)_qA$, CO-Het, $(CR_2)_n$Het, $O(CR_2)_nNR_2$, $CR^5=CR^5Ar^1$ and/or $SO_2$Het,
Het denotes piperidinyl, piperazinyl, pyrrolidinyl, morpholinyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, indolyl, benzo-1,3-dioxolyl, indazolyl, 2,3-dihydrobenzo-1,4-dioxinyl, chromanyl or benzo-2,1,3-thiadiazolyl, each of which is unsubstituted or mono- or disubstituted by Hal, A, $Ar^1$ and/or =O (carbonyl oxygen),
$Ar^1$ denotes phenyl which is unsubstituted or mono-, di-, tri-, tetra- or pentasubstituted by Hal, CN, A and/or $(CR_2)_nOR$,
A denotes unbranched or branched alkyl having 1-10 C atoms, in which 1-7H atoms may be replaced by F and/or Cl,
m denotes 1, 2, 3 or 4,
n denotes 0, 1, 2, 3 or 4,
p denotes 1, 2, 3 or 4,
q denotes 0, 1 or 2,
Hal denotes F, Cl, Br or I;
and pharmaceutically usable salts, tautomers and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

The starting materials can, if desired, also be formed in situ by not isolating them from the reaction mixture, but instead immediately converting them further into the compounds of the formula I.

Compounds of the formula I can preferably be obtained by reacting a compound of the formula II with a compound of the formula III.

In the compounds of the formula III, L preferably denotes Cl, Br, I or a free or reactively modified OH group, such as, for example, an activated ester, an imidazolide or alkylsulfonyloxy having 1-6 C atoms (preferably methylsulfonyloxy or trifluoromethylsulfonyloxy) or arylsulfonyloxy having 6-10 C atoms (preferably phenyl- or p-tolylsulfonyloxy).

The reaction preferably succeeds in the presence of a dehydrating agent, such as, for example, a carbodiimide, such as N,N'-dicyclohexylcarbodiimide ("DCCI"), 1,1'-carbonyldiimidazole or N-3-dimethylaminopropyl-N'-ethylcarbodiimide ("DAPECI"), furthermore propanephosphonic anhydride (cf. Angew. Chem. 92, 129 (1980)), diphenylphosphoryl azide or 2-ethoxy-N-ethoxycarbonyl-1,2-dihydroquinoline.

The reaction is generally carried out in the presence of an acid-binding agent, preferably an organic base, such as DIPEA, triethylamine, dimethylaniline, pyridine or quinoline.

The addition of an alkali or alkaline-earth metal hydroxide, carbonate or bicarbonate or another salt of a weak acid of the alkali or alkaline-earth metals, preferably of potassium, sodium, calcium or caesium, may also be favourable.

Depending on the conditions used, the reaction time is between a few minutes and 14 days, the reaction temperature is between about −30° and 140°, normally between −10° and 90°, in particular between about 0° and about 70°.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to acetonitrile, dichloromethane and/or DMF.

The starting compounds of the formulae II and III are generally known. If they are novel, however, they can be prepared by methods known per se. The starting materials are generally also commercially available.

Compounds of the formula I can furthermore preferably be obtained by reacting a compound of the formula IV with a compound of the formula V. In the compounds of the formula V, L preferably denotes Cl, Br, I or a free or reactively modified OH group, such as, for example, an activated ester, an imidazolide or alkylsulfonyloxy having 1-6 C atoms (preferably methylsulfonyloxy or trifluoromethylsulfonyloxy) or arylsulfonyloxy having 6-10 C atoms (preferably phenyl- or p-tolylsulfonyloxy).

The reaction is generally carried out under conditions as indicated above.

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline-earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline-earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)-methylamine (tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; $di(C_1-C_4)$ alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline-earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The invention furthermore relates to medicaments comprising at least one compound of the formula I and/or pharmaceutically usable and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or more usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound of the formula I and/or pharmaceutically usable and stereoisomers thereof, including mixtures thereof in all ratios, and at least one further medicament active ingredient.

The invention also relates to a set (kit) consisting of separate packs of (a) an effective amount of a compound of the formula I and/or pharmaceutically usable and stereoisomers thereof, including mixtures thereof in all ratios,
and
(b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically usable and stereoisomers thereof, including mixtures thereof in all ratios, and an effective amount of a further medicament active ingredient in dissolved or lyophilised form.

The medicaments from Table 1 are preferably, but not exclusively, combined with the compounds of the formula I. A combination of the formula I and medicaments from Table I can also be combined with compounds of the formula VI.

TABLE 1

| | | |
|---|---|---|
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechlorethamine |
| | Thiotepa | Streptozocin |
| | Chlorambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aeterna) |
| | Carboxyphthalatoplatinum | Satraplatin (Johnson Matthey) |
| | Tetraplatin | |
| | Ormiplatin | BBR-3464 (Hoffmann-La Roche) |
| | Iproplatin | SM-11355 (Sumitomo) |
| | | AP-5280 (Access) |

TABLE 1-continued

| | | |
|---|---|---|
| Antimetabolites | Azacytidine | Tomudex |
| | Gemcitabine | Trimetrexate |
| | Capecitabine | Deoxycoformycin |
| | 5-Fluorouracil | Fludarabine |
| | Floxuridine | Pentostatin |
| | 2-Chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-Fluorodesoxycytidine | Irofulven (MGI Pharma) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma-Tau) |
| | Irinotecan (CPT-11) | Diflomotecan (Beaufour-Ipsen) |
| | 7-Ethyl-10-hydroxycamptothecin | TAS-103 (Taiho) |
| | Topotecan | Elsamitrucin (Spectrum) |
| | Dexrazoxanet (TopoTarget) | J-107088 (Merck & Co) |
| | Pixantrone (Novuspharrna) | BNP-1350 (BioNumerik) |
| | Rebeccamycin analogue (Exelixis) | CKD-602 (Chong Kun Dang) |
| | BBR-3576 (Novuspharrna) | KW-2170 (Kyowa Hakko) |
| Antitumour antibiotics | Dactinomycin (Actinomycin D) | Amonafide |
| | Doxorubicin (Adriamycin) | Azonafide |
| | Deoxyrubicin | Anthrapyrazole |
| | Valrubicin | Oxantrazole |
| | Daunorubicin (Daunomycin) | Losoxantrone |
| | | Bleomycin sulfate (Blenoxan) |
| | Epirubicin | Bleomycinic acid |
| | Therarubicin | Bleomycin A |
| | Idarubicin | Bleomycin B |
| | Rubidazone | Mitomycin C |
| | Plicamycinp | MEN-10755 (Menarini) |
| | Porfiromycin | GPX-100 (Gem Pharmaceuticals) |
| | Cyanomorpholinodoxorubicin | |
| | Mitoxantrone (Novantrone) | |
| Antimitotic agents | Paclitaxel | SB 408075 (GlaxoSmithKline) |
| | Docetaxel | E7010 (Abbott) |
| | Colchicine | PG-TXL (Cell Therapeutics) |
| | Vinblastine | |
| | Vincristine | |
| | Vinorelbine | IDN 5109 (Bayer) |
| | Vindesine | A 105972 (Abbott) |
| | Dolastatin 10 (NCI) | A 204197 (Abbott) |
| | Rhizoxin (Fujisawa) | LU 223651 (BASF) |
| | Mivobulin (Warner-Lambert) | D 24851 (ASTA Medica) |
| | | ER-86526 (Eisai) |
| | Cemadotin (BASF) | Combretastatin A4 (BMS) |
| | RPR 109881A (Aventis) | Isohomohalichondrin-B (PharmaMar) |
| | TXD 258 (Aventis) | |
| | Epothilone B (Novartis) | ZD 6126 (AstraZeneca) |
| | T 900607 (Tularik) | PEG-Paclitaxel (Enzon) |
| | T 138067 (Tularik) | AZ10992 (Asahi) |
| | Cryptophycin 52 (Eli Lilly) | !DN-5109 (Indena) |
| | Vinflunine (Fabre) | AVLB (Prescient NeuroPharma) |
| | Auristatin PE (Teikoku hormone) | Azaepothilon B (BMS) |
| | BMS 247550 (BMS) | BNP-7787 (BioNumerik) |
| | BMS 184476 (BMS) | CA-4-prodrug (OXiGENE) |
| | BMS 188797 (BMS) | Dolastatin-10 (NrH) |
| | Taxoprexin (Protarga) | CA-4 (OXiGENE) |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate synthase inhibitors | Pemetrexed (Eli Lilly) | Nolatrexed (Eximias) |
| | ZD-9331 (BTG) | CoFactor ™ (BioKeys) |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (Isotope Solutions) | O6-benzylguanine |

TABLE 1-continued

| | | |
|---|---|---|
| | Thymectacin (NewBiotics) | (Paligent) |
| | Edotreotid (Novartis) | |
| Farnesyl transferase inhibitors | Arglabin (NuOncology Labs) | Tipifarnib (Johnson & Johnson) |
| | Ionafarnib (Schering-Plough) | Perillyl alcohol (DOR BioPharma) |
| | BAY-43-9006 (Bayer) | |
| Pump inhibitors | CBT-1 (CBA Pharma) | Zosuquidar trihydrochloride (Eli Lilly) |
| | Tariquidar (Xenova) | |
| | MS-209 (Schering AG) | Biricodar dicitrate (Vertex) |
| Histone acetyl transferase inhibitors | Tacedinaline (Pfizer) | Pivaloyloxymethyl butyrate (Titan) |
| | SAHA (Aton Pharma) | |
| | MS-275 (Schering AG) | Depsipeptide (Fujisawa) |
| Metalloproteinase inhibitors | Neovastat (Aeterna Laboratories) | CMT-3 (CollaGenex) |
| | Marimastat (British Biotech) | BMS-275291 (Celltech) |
| Ribonucleoside reductase inhibitors | Gallium maltolate (Titan) | Tezacitabine (Aventis) |
| | Triapin (Vion) | Didox (Molecules for Health) |
| TNF-alpha agonists/ antagonists | Virulizin (Lorus Therapeutics) | Revimid (Celgene) |
| | CDC-394 (Celgene) | |
| Endothelin-A receptor antagonists | Atrasentan (Abbot) | YM-598 (Yamanouchi) |
| | ZD-4054 (AstraZeneca) | |
| Retinoic acid receptor agonists | Fenretinide (Johnson & Johnson) | Alitretinoin (Ligand) |
| | LGD-1550 (Ligand) | |
| Immunomodulators | Interferon | Dexosome therapy (Anosys) |
| | Oncophage (Antigenics) | Pentrix (Australian Cancer Technology) |
| | GMK (Progenics) | |
| | Adenocarcinoma vaccine (Biomira) | JSF-154 (Tragen) |
| | | Cancer vaccine (Intercell) |
| | CTP-37 (AVI BioPharma) | Norelin (Biostar) |
| | JRX-2 (Immuno-Rx) | BLP-25 (Biomira) |
| | PEP-005 (Peplin Biotech) | MGV (Progenics) |
| | Synchrovax vaccines (CTL Immuno) | !3-Alethin (Dovetail) |
| | | CLL-Thera (Vasogen) |
| | Melanoma vaccine (CTL Immuno) | |
| | p21-RAS vaccine (Gem-Vax) | |
| Hormonal and antihormonal agents | Oestrogens | Prednisone |
| | Conjugated oestrogens | Methylprednisolone |
| | Ethynyloestradiol | Prednisolone |
| | Chlorotrianisene | Aminoglutethimide |
| | Idenestrol | Leuprolide |
| | Hydroxyprogesterone caproate | Goserelin |
| | | Leuporelin |
| | Medroxyprogesterone | Bicalutamide |
| | Testosterone | Flutamide |
| | Testosterone propionate | Octreotide |
| | Fluoxymesterone | Nilutamide |
| | Methyltestosterone | Mitotan |
| | Diethylstilbestrol | P-04 (Novogen) |
| | Megestrol | 2-Methoxyoestradiol (Entre Med) |
| | Tamoxifen | |
| | Toremofin | Arzoxifen (Eli Lilly) |
| | Dexamethasone | |
| Photodynamic agents | Talaporfin (Light Sciences) | Pd-bacteriopheophorbide (Yeda) |
| | Theralux (Theratechnologies) | |
| | Motexafin gadolinium (Pharmacyclics) | Lutetium texaphyrin (Pharmacyclics) |
| | | Hypericin |
| Tyrosine kinase inhibitors | Imatinib (Novartis) | Kahalide F (PharmaMar) |
| | Leflunomide (Sugen/Pharmacia) | CEP-701 (Cephalon) |
| | | CEP-751 (Cephalon) |
| | ZDI839 (AstraZeneca) | MLN518 (Millenium) |
| | Erlotinib (Oncogene Science) | PKC412 (Novartis) |
| | | Phenoxodiol O |
| | Canertjnib (Pfizer) | Trastuzumab (Genentech) |
| | Squalamine (Genaera) | C225 (ImClone) |
| | SU5416 (Pharmacia) | rhu-Mab (Genentech) |
| | SU6668 (Pharmacia) | MDX-H210 (Medarex) |
| | ZD4190 (AstraZeneca) | 2C4 (Genentech) |
| | ZD6474 (AstraZeneca) | MDX-447 (Medarex) |
| | Vatalanib (Novartis) | ABX-EGF (Abgenix) |
| | PKI166 (Novartis) | IMC-1C11 (ImClone) |
| | GW2016 (GlaxoSmithKline) | |
| | EKB-509 (Wyeth) | |
| | EKB-569 (Wyeth) | |

TABLE 1-continued

| | | |
|---|---|---|
| Various agents | SR-27897 (CCK-A inhibitor, Sanofi-Synthelabo) | BCX-1777 (PNP inhibitor, BioCryst) |
| | Tocladesine (cyclic AMP agonist, Ribapharm) | Ranpirnase (ribonuclease stimulant, Alfacell) |
| | Alvocidib (CDK inhibitor, Aventis) | Galarubicin (RNA synthesis inhibitor, Dong-A) |
| | CV-247 (COX-2 inhibitor, Ivy Medical) | Tirapazamine (reducing agent, SRI International) |
| | P54 (COX-2 inhibitor, Phytopharm) | N-Acetylcysteine (reducing agent, Zambon) |
| | CapCell ™ (CYP450 stimulant, Bavarian Nordic) | R-Flurbiprofen (NF-kappaB inhibitor, Encore) |
| | GCS-IOO (gal3 antagonist, GlycoGenesys) | 3CPA (NF-kappaB inhibitor, Active Biotech) |
| | G17DT immunogen (gastrin inhibitor, Aphton) | Seocalcitol (vitamin D receptor agonist, Leo) |
| | Efaproxiral (oxygenator, Allos Therapeutics) | 131-I-TM-601 (DNA antagonist, TransMolecular) |
| | PI-88 (heparanase inhibitor, Progen) | Eflornithin (ODC inhibitor, ILEX Oncology) |
| | Tesmilifen (histamine antagonist, YM BioSciences) | Minodronic acid (osteoclast inhibitor, Yamanouchi) |
| | Histamine (histamine H2 receptor agonist, Maxim) | Indisulam (p53 stimulant, Eisai) |
| | Tiazofurin (IMPDH inhibitor, Ribapharm) | Aplidin (PPT inhibitor, PharmaMar) |
| | Cilengitide (integrin antagonist, Merck KGaA) | Rituximab (CD20 antibody, Genentech) |
| | SR-31747 (IL-1 antagonist, Sanofi-Synthelabo) | Gemtuzumab (CD33 antibody, Wyeth Ayerst) |
| | CCI-779 (mTOR kinase inhibitor, Wyeth) | PG2 (haematopoiesis promoter, Pharmagenesis) |
| | Exisulind (PDE-V inhibitor, Cell Pathways) | Immunol ™ (triclosan mouthwash, Endo) |
| | CP-461 (PDE-V inhibitor, Cell Pathways) | Triacetyluridine (uridine prodrug, Wellstat) |
| | AG-2037 (GART inhibitor, Pfizer) | SN-4071 (sarcoma agent, Signature BioScience) |
| | WX-UK1 (plasminogen activator inhibitor, Wilex) | TransMID-107 ™ (immunotoxin, KS Biomedix) |
| | PBI-1402 (PMN stimulant, ProMetic LifeSciences) | PCK-3145 (apoptosis promoter, Procyon) |
| | Bortezomib (proteasome inhibitor, Millennium) | Doranidazole (apoptosis promoter, Pola) |
| | SRL-172 (T-cell stimulant, SR Pharma) | CHS-828 (cytotoxic agent, Leo) |
| | TLK-286 (glutathione-S transferase inhibitor, Telik) | Trans-retinoic acid (differentiator, NIH) |
| | PT-100 (growth factor agonist, Point Therapeutics) | MX6 (apoptosis promoter, MAXIA) |
| | Midostaurin (PKC inhibitor, Novartis) | Apomine (apoptosis promoter, ILEX Oncology) |
| | Bryostatin-1 (PKC stimuant, GPC Biotech) | Urocidin (apoptosis promoter, Bioniche) |
| | CDA-II (apoptosis promoter, Everlife) | Ro-31-7453 (apoptosis promoter, La Roche) |
| | SDX-101 (apoptosis promoter, Salmedix) | Brostallicin (apoptosis promoter, Pharmacia) |
| | Ceflatonin (apoptosis promoter, ChemGenex) | |
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechlorethamine |
| | Thiotepa | Streptozocin |
| | Chlorambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aetema) |
| | Carboxyphthalatoplatinum | Satraplatin (Johnson Matthey) |
| | Tetraplatin | BBR-3464 (Hoffmann-La Roche) |
| | Ormiplatin | SM-11355 (Sumitomo) |
| | Iproplatin | AP-5280 (Access) |

TABLE 1-continued

| | | |
|---|---|---|
| Antimetabolites | Azacytidine | Tomudex |
| | Gemcitabine | Trimetrexate |
| | Capecitabine | Deoxycoformycin |
| | 5-Fluorouracil | Fludarabine |
| | Floxuridine | Pentostatin |
| | 2-Chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-Fluorodesoxycytidine | Irofulven (MGI Pharma) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | |
| | Teniposide or mitoxantrone | Quinamed (ChemGenex) |
| | | Gimatecan (Sigma-Tau) |
| | Irinotecan (CPT-11) | Diflomotecan (Beaufour-Ipsen) |
| | 7-Ethyl-10-hydroxycamptothecin | TAS-103 (Taiho) |
| | Topotecan | Elsamitrucin (Spectrum) |
| | Dexrazoxanet (TopoTarget) | J-107088 (Merck & Co) |
| | | BNP-1350 (BioNumerik) |
| | Pixantrone (Novuspharrna) | CKD-602 (Chong Kun Dang) |
| | Rebeccamycin analogue (Exelixis) | KW-2170 (Kyowa Hakko) |
| | BBR-3576 (Novuspharrna) | |
| Antitumour antibiotics | Dactinomycin (Actinomycin D) | Amonafide |
| | | Azonafide |
| | Doxorubicin (Adriamycin) | Anthrapyrazole |
| | Deoxyrubicin | Oxantrazole |
| | Valrubicin | Losoxantrone |
| | Daunorubicin (Daunomycin) | Bleomycin sulfate (Blenoxan) |
| | Epirubicin | Bleomycinic acid |
| | Therarubicin | Bleomycin A |
| | Idarubicin | Bleomycin B |
| | Rubidazone | Mitomycin C |
| | Plicamycinp | MEN-10755 (Menarini) |
| | Porfiromycin | GPX-100 (Gem Pharmaceuticals) |
| | Cyanomorpholinodoxo-rubicin | |
| | Mitoxantrone (Novantrone) | |
| Antimitotic agents | Paclitaxel | SB 408075 (GlaxoSmithKline) |
| | Docetaxel | E7010 (Abbott) |
| | Colchicine | |
| | Vinblastine | PG-TXL (Cell Therapeutics) |
| | Vincristine | |
| | Vinorelbine | IDN 5109 (Bayer) |
| | Vindesine | A 105972 (Abbott) |
| | Dolastatin 10 (NCI) | A 204197 (Abbott) |
| | Rhizoxin (Fujisawa) | LU 223651 (BASF) |
| | Mivobulin (Warner-Lambert) | D 24851 (ASTA Medica) |
| | | ER-86526 (Eisai) |
| | Cemadotin (BASF) | Combretastatin A4 (BMS) |
| | RPR 109881A (Aventis) | Isohomohalichondrin-B (PharmaMar) |
| | TXD 258 (Aventis) | |
| | Epothilone B (Novartis) | ZD 6126 (AstraZeneca) |
| | T 900607 (Tularik) | PEG-Paclitaxel (Enzon) |
| | T 138067 (Tularik) | AZ10992 (Asahi) |
| | Cryptophycin 52 (Eli Lilly) | !DN-5109 (Indena) |
| | Vinflunine (Fabre) | AVLB (Prescient NeuroPharma) |
| | Auristatin PE (Teikoku hormone) | |
| | | Azaepothilon B (BMS) |
| | BMS 247550 (BMS) | BNP-7787 (BioNumerik) |
| | BMS 184476 (BMS) | CA-4-prodrug (OXiGENE) |
| | BMS 188797 (BMS) | Dolastatin-10 (NrH) |
| | Taxoprexin (Protarga) | CA-4 (OXiGENE) |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate synthase inhibitors | Pemetrexed (Eli Lilly) | Nolatrexed (Eximias) |
| | ZD-9331 (BTG) | CoFactor ™ (BioKeys) |
| DNA antagonists | Trabectedin (PharmaMar) | Mafosfamide (Baxter International) |
| | Glufosfamide (Baxter International) | |
| | | Apaziquone (Spectrum Pharmaceuticals) |
| | Albumin + 32P (Isotope | |

TABLE 1-continued

| | | |
|---|---|---|
| | Solutions) | O6-benzylguanine |
| | Thymectacin (NewBiotics) | (Paligent) |
| | Edotreotid (Novartis) | |
| Farnesyl transferase inhibitors | Arglabin (NuOncology Labs) | Tipifarnib (Johnson & Johnson) |
| | Ionafarnib (Schering-Plough) | Perillyl alcohol (DOR BioPharma) |
| | BAY-43-9006 (Bayer) | |
| Pump inhibitors | CBT-1 (CBA Pharma) | Zosuquidar trihydrochloride (Eli Lilly) |
| | Tariquidar (Xenova) | |
| | MS-209 (Schering AG) | Biricodar dicitrate (Vertex) |
| Histone acetyl transferase inhibitors | Tacedinaline (Pfizer) | Pivaloyloxymethyl butyrate (Titan) |
| | SAHA (Aton Pharma) | |
| | MS-275 (Schering AG) | Depsipeptide (Fujisawa) |
| Metalloproteinase inhibitors | Neovastat (Aeterna Laboratories) | CMT-3 (CollaGenex) |
| | Marimastat (British Biotech) | BMS-275291 (Celltech) |
| Ribonucleoside reductase inhibitors | Gallium maltolate (Titan) | Tezacitabine (Aventis) |
| | Triapin (Vion) | Didox (Molecules for Health) |
| TNF-alpha agonists/ antagonists | Virulizin (Lorus Therapeutics) | Revimid (Celgene) |
| | CDC-394 (Celgene) | |
| Endothelin-A receptor antagonists | Atrasentan (Abbot) | YM-598 (Yamanouchi) |
| | ZD-4054 (AstraZeneca) | |
| Retinoic acid receptor agonists | Fenretinide (Johnson & Johnson) | Alitretinoin (Ligand) |
| | LGD-1550 (Ligand) | |
| Immunomodulators | Interferon | Dexosome therapy (Anosys) |
| | Oncophage (Antigenics) | Pentrix (Australian Cancer Technology) |
| | GMK (Progenics) | |
| | Adenocarcinoma vaccine (Biomira) | JSF-154 (Tragen) |
| | | Cancer vaccine (Intercell) |
| | CTP-37 (AVI BioPharma) | Norelin (Biostar) |
| | JRX-2 (Immuno-Rx) | BLP-25 (Biomira) |
| | PEP-005 (Peplin Biotech) | MGV (Progenics) |
| | Synchrovax vaccines (CTL Immuno) | !3-Alethin (Dovetail) |
| | | CLL-Thera (Vasogen) |
| | Melanoma vaccine (CTL Immuno) | |
| | p21-RAS vaccine (Gem-Vax) | |
| Hormonal and antihormonal agents | Oestrogens | Prednisone |
| | Conjugated oestrogens | Methylprednisolone |
| | Ethynyloestradiol | Prednisolone |
| | Chlorotrianisene | Aminoglutethimide |
| | Idenestrol | Leuprolide |
| | Hydroxyprogesterone caproate | Goserelin |
| | | Leuporelin |
| | Medroxyprogesterone | Bicalutamide |
| | Testosterone | Flutamide |
| | Testosterone propionate | Octreotide |
| | Fluoxymesterone | Nilutamide |
| | Methyltestosterone | Mitotan |
| | Diethylstilbestrol | P-04 (Novogen) |
| | Megestrol | 2-Methoxyoestradiol (EntreMed) |
| | Tamoxifen | |
| | Toremofin | Arzoxifen (Eli Lilly) |
| | Dexamethasone | |
| Photodynamic agents | Talaporfin (Light Sciences) | Pd-bacteriopheophorbide (Yeda) |
| | Theralux (Theratechnologies) | |
| | Motexafin gadolinium (Pharmacyclics) | Lutetium texaphyrin (Pharmacyclics) |
| | | Hypericin |
| Tyrosine kinase inhibitors | Imatinib (Novartis) | Kahalide F (PharmaMar) |
| | Leflunomide (Sugen/Pharmacia) | CEP-701 (Cephalon) |
| | | CEP-751 (Cephalon) |
| | ZDI839 (AstraZeneca) | MLN518 (Millenium) |
| | Erlotinib (Oncogene Science) | PKC412 (Novartis) |
| | | Phenoxodiol O |
| | Canertjnib (Pfizer) | Trastuzumab (Genentech) |
| | Squalamine (Genaera) | C225 (ImClone) |
| | SU5416 (Pharmacia) | rhu-Mab (Genentech) |
| | SU6668 (Pharmacia) | MDX-H210 (Medarex) |
| | ZD4190 (AstraZeneca) | 2C4 (Genentech) |
| | ZD6474 (AstraZeneca) | MDX-447 (Medarex) |
| | Vatalanib (Novartis) | ABX-EGF (Abgenix) |
| | PKI166 (Novartis) | IMC-1C11 (ImClone) |
| | GW2016 (GlaxoSmithKline) | |

TABLE 1-continued

| | | |
|---|---|---|
| Various agents | EKB-509 (Wyeth) <br> EKB-569 (Wyeth) <br> SR-27897 (CCK-A inhibitor, Sanofi-Synthelabo) <br> Tocladesine (cyclic AMP agonist, Ribapharm) <br> Alvocidib (CDK inhibitor, Aventis) <br> CV-247 (COX-2 inhibitor, Ivy Medical) <br> P54 (COX-2 inhibitor, Phytopharm) <br> CapCell ™ (CYP450 stimulant, Bavarian Nordic) <br> GCS-IOO (gal3 antagonist, GlycoGenesys) <br> G17DT immunogen (gastrin inhibitor, Aphton) <br> Efaproxiral (oxygenator, Allos Therapeutics) <br> PI-88 (heparanase inhibitor, Progen) <br> Tesmilifen (histamine antagonist, YM BioSciences) <br> Histamine (histamine H2 receptor agonist, Maxim) <br> Tiazofurin (IMPDH inhibitor, Ribapharm) <br> Cilengitide (integrin antagonist, Merck KGaA) <br> SR-31747 (IL-1 antagonist, Sanofi-Synthelabo) <br> CCI-779 (mTOR kinase inhibitor, Wyeth) <br> Exisulind (PDE-V inhibitor, Cell Pathways) <br> CP-461 (PDE-V inhibitor, Cell Pathways) <br> AG-2037 (GART inhibitor, Pfizer) <br> WX-UK1 (plasminogen activator inhibitor, Wilex) <br> PBI-1402 (PMN stimulant, ProMetic LifeSciences) <br> Bortezomib (proteasome inhibitor, Millennium) <br> SRL-172 (T-cell stimulant, SR Pharma) <br> TLK-286 (glutathione-S transferase inhibitor, Telik) <br> PT-100 (growth factor agonist, Point Therapeutics) <br> Midostaurin (PKC inhibitor, Novartis) <br> Bryostatin-1 (PKC stimuant, GPC Biotech) <br> CDA-II (apoptosis promoter, Everlife) <br> SDX-101 (apoptosis promoter, Salmedix) <br> Ceflatonin (apoptosis promoter, ChemGenex) | BCX-1777 (PNP inhibitor, BioCryst) <br> Ranpirnase (ribonuclease stimulant, Alfacell) <br> Galarubicin (RNA synthesis inhibitor, Dong-A) <br> Tirapazamine (reducing agent, SRI International) <br> N-Acetylcysteine (reducing agent, Zambon) <br> R-Flurbiprofen (NF-kappaB inhibitor, Encore) <br> 3CPA (NF-kappaB inhibitor, Active Biotech) <br> Seocalcitol (vitamin D receptor agonist, Leo) <br> 131-I-TM-601 (DNA antagonist, TransMolecular) <br> Eflornithin (ODC inhibitor, ILEX Oncology) <br> Minodronic acid (osteoclast inhibitor, Yamanouchi) <br> Indisulam (p53 stimulant, Eisai) <br> Aplidin (PPT inhibitor, PharmaMar) <br> Rituximab (CD20 antibody, Genentech) <br> Gemtuzumab (CD33 antibody, Wyeth Ayerst) <br> PG2 (haematopoiesis promoter, Pharmagenesis) <br> Immunol ™ (triclosan mouthwash, Endo) <br> Triacetyluridine (uridine prodrug, Wellstat) <br> SN-4071 (sarcoma agent, Signature BioScience) <br> TransMID-107 ™ (immunotoxin, KS Biomedix) <br> PCK-3145 (apoptosis promoter, Procyon) <br> Doranidazole (apoptosis promoter, Pola) <br> CHS-828 (cytotoxic agent, Leo) <br> Trans-retinoic acid (differentiator, NIH) <br> MX6 (apoptosis promoter, MAXIA) <br> Apomine (apoptosis promoter, ILEX Oncology) <br> Urocidin (apoptosis promoter, Bioniche) <br> Ro-31-7453 (apoptosis promoter, La Roche) <br> Brostallicin (apoptosis promoter, Pharmacia) | |

The compounds of the formula I are preferably combined with the with known anti-cancer agents:

These known anti-cancer agents include the following: oestrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors and other angiogenesis inhibitors. The present compounds are particularly suitable for administration at the same time as radiotherapy. The synergistic effects of inhibition of VEGF in combination with radiotherapy have been described in the art (see WO 00/61186).

"Oestrogen receptor modulators" refers to compounds which interfere with or inhibit the binding of oestrogen to the receptor, regardless of mechanism. Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl] phenyl 2,2-dimethylpropanoate, 4,4'-dihydroxybenzophenone-2,4-dinitrophenylhydrazone and SH646. "Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide and N-4-carboxyphenyl-retinamide.

"Cytotoxic agents" refers to compounds which result in cell death primarily through direct action on the cellular function or inhibit or interfere with cell myosis, including alkylating agents, tumour necrosis factors, intercalators, microtubulin inhibitors and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cisaminedichloro(2-methylpyridine)platinum, benzylguanine, glufosfamide, GPX100, (trans,trans,trans)bis-mu-(hexane-1,6-diamine)mu-[diamineplatinum(II)]bis[diamine(chloro)platinum(II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplastone, 3'-deamino-3'-morpholino-13-deoxo-10-hydroxycaminomycin, annamycin, galarubicin, elinafide, MEN10755 and 4-demethoxy-3-deamino-3-aziridinyl-4-methyl-sulfonyldaunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzenesulfonamide, anhydrovinblastine, N,N-dimethyl-L-valyl-L-valyl-N-methyl-L-valyl-L-prolyl-L-proline-t-butylamide, TDX258 and BMS188797.

Some examples of topoisomerase inhibitors are topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4':b,7]indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxyetoposide, GL331, N-[2-(dimethylamino)-ethyl]-9-hydroxy-5,6-dimethyl-6H-pyrido[4,3-b]carbazole-1-carboxamide, asulacrine, (5a,5aB,8aa, 9b)-9-[2-[N-[2-(dimethylamino)ethyl]-N-methylamino] ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]phenanthridinium, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethyl]amino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one and dimesna.

"Antiproliferative agents" include antisense RNA and DNA oligonucleotides such as G3139, ODN698, RVASK-RAS, GEM231 and INX3001 and anti-metabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-mannoheptopyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-ylacetic acid ester, swainsonine, lometrexol, dexrazoxane, methioninase, 2'-cyano-2'-deoxy-N4-palmitoyl-1-B-D-arabinofuranosyl cytosine and 3-aminopyridine-2-carboxaldehyde thiosemicarbazone. "Antiproliferative agents" also include monoclonal antibodies to growth factors other than those listed under "angiogenesis inhibitors", such as trastuzumab, and tumour suppressor genes, such as p53, which can be delivered via recombinant virus-mediated gene transfer (see U.S. Pat. No. 6,069,134, for example).

Particular preference is given to the use of the compound according to the invention for the treatment and prophylaxis of tumour diseases.

The tumour is preferably selected from the group of tumours of the squamous epithelium, of the bladder, of the stomach, of the kidneys, of head and neck, of the oesophagus, of the cervix, of the thyroid, of the intestine, of the liver, of the brain, of the prostate, of the urogenital tract, of the lymphatic system, of the stomach, of the larynx and/or of the lung.

The tumour is furthermore preferably selected from the group lung adenocarcinoma, small-cell lung carcinomas, pancreatic cancer, glioblastomas, colon carcinoma and breast carcinoma.

Preference is furthermore given to the use for the treatment of a tumour of the blood and immune system, preferably for the treatment of a tumour selected from the group of acute myeloid leukaemia, chronic myeloid leukaemia, acute lymphatic leukaemia and/or chronic lymphatic leukaemia.

In another aspect, the invention encompasses a for the treatment of a patient who has a neoplasm, such as a cancer, by administration of a compound of the formula (I) in combination with an antiproliferative agent. Suitable antiproliferative agents encompass those provided in Table 1.

Above and below, all temperatures are indicated in ° C. In the following examples, "conventional work-up" means: if necessary, water is added, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel; eluent: ethyl acetate/methanol 9:1.

Mass spectrometry (MS): EI (electron impact ionisation) M+

FAB (fast atom bombardment) (M+H)+

ESI (electrospray ionisation) (M+H)+

APCI-MS (atmospheric pressure chemical ionisation—mass spectrometry) (M+H)+

LC/MS method:

Solvent A: water+0.1% of TFA

Solvent B: acetonitrile+0.1% of TFA

Flow: 2.4 ml/min

35

Gradient: 0.0 min 4% of B
  2.6 min 100% of B
Column: Chromolith® Speed ROD RP-18e 50-4, 6 mm
HPLC method:
Solvent A: water+0.1% of TFA
Solvent B: acetonitrile+0.08% of TFA
Flow: 1.5 ml/min

36

Column: Chromolith® RP18e 100-4, 6 mm

EXAMPLE 1

The synthesis of 4-chlorobenzyl 4-[3-oxo-3-(2-oxo-2,3-dihydrobenzoxazol-6-yl)propyl]piperazine-1-carboxylate ("A1") is carried out analogously to the following scheme

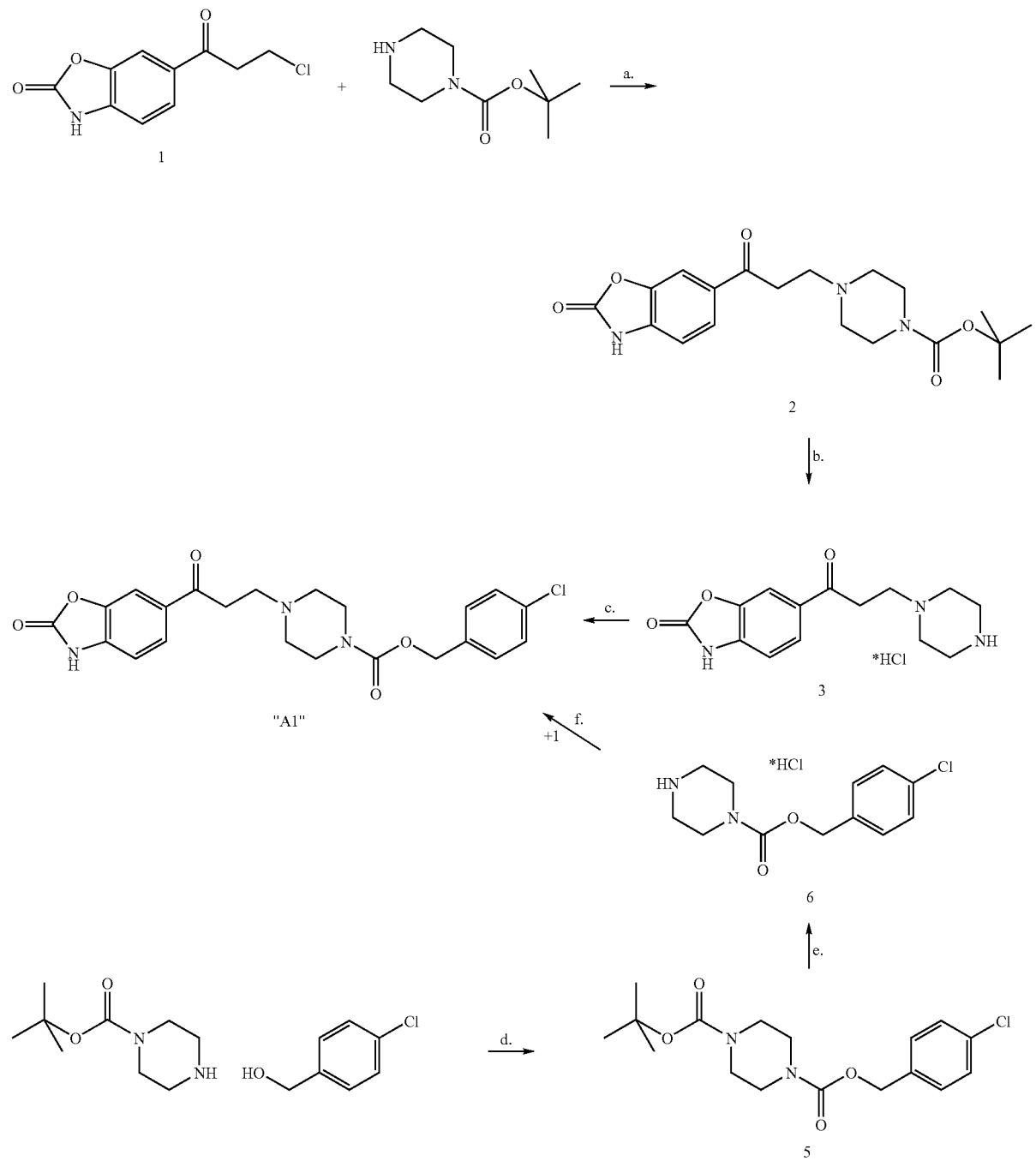

Gradient: 0.0 min 20% of B
  6.0 min 100% of B
  7.0 min 100% of B
  8.0 min 20% of B
  9.0 min 20% of B a. Compound 1 (8.60 g, 38.1 mmol) is initially introduced in DCM (80 ml), triethylamine (17.4 ml, 126 mmol)) is added at RT, and tert-butyl 1-piperazine-N-carboxylate (7.80 g, 41.9 mmol) is subsequently added at RT. Stirring is continued at RT for 18 h. Half of the solvent is removed in a rotary evaporator, diluted with ethyl ether (5 ml), and the precipitate which has formed is filtered off. The latter is washed with water and dried (vacuum drying cabinet). The resultant colourless product is reacted without further purification (colourless solid 2, 10.8 g, 28.8 mmol, 76%).

b. Compound 2 (10.5 g, 27.7 mmol) is taken up in 6N HCl in 2-propanol (170 ml), and stirring is continued at RT for 75 min. The precipitate is filtered off and dried, giving a colourless solid 3 (8.60 g, 27.6 mmol, 100%).

stirred at RT for 2 d. The reaction solution is added to water (500 ml), and the precipitate which has formed is filtered off with suction, rinsed with water and dried in vacuo, giving "A1" (7.50 g, 16.9 mmol, 98%).

EXAMPLE 2

The synthesis of 6-(3-{4-[2-(4-chlorophenoxy)acetyl]piperazin-1-yl}propionyl)-3H-benzoxazol-2-one ("A2") is carried out analogously to the following scheme

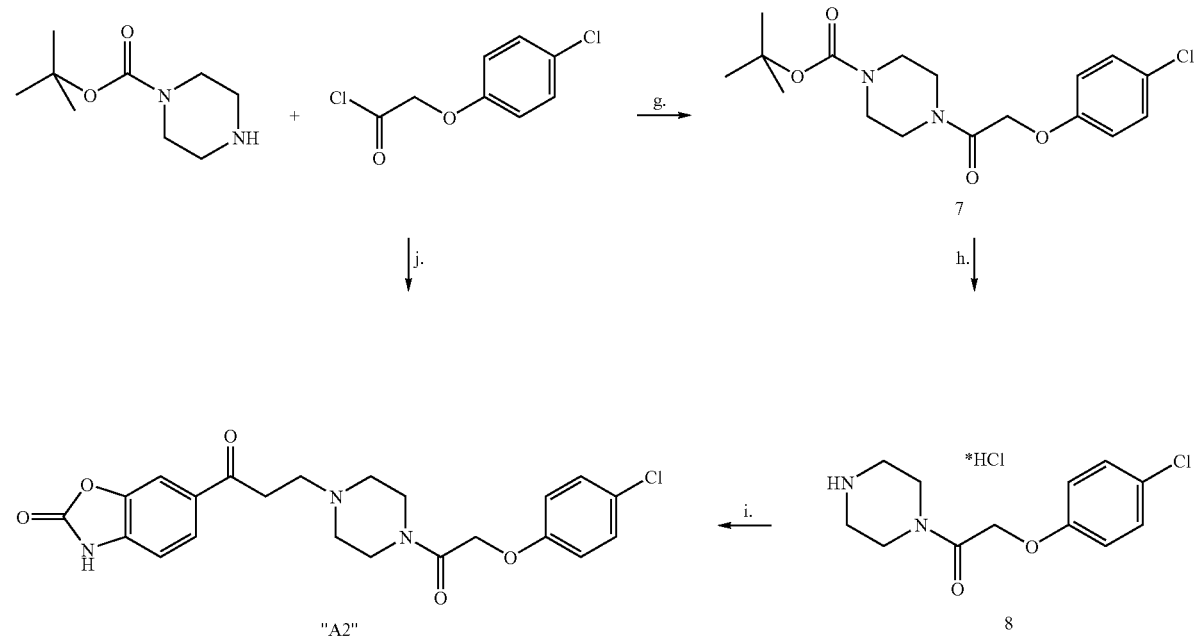

c. 4-Chlorobenzyl alcohol (27.4 mg, 0.19 mmol) is dissolved in DMF (5 ml), 1,1'-carbonyldiimidazole (31.1 mg, 0.19 mmol) is added, and stirring is continued at RT for 3 h. Compound 3 (60.0 mg, 0.19 mmol) is added to this mixture. Stirring is continued at RT for 18 h. Water (10 ml) is added to the reaction mixture, and the precipitate which has formed is filtered off. The latter is washed with water and dried (vacuum drying cabinet), giving 4-chlorobenzyl 4-[3-oxo-3-(2-oxo-2,3-dihydrobenzoxazol-6-yl)propyl]-piperazine-1-carboxylate ("A1") (85.0 mg, 019 mmol, 100%); [M+H$^+$] 445; Rt HPLC 3.57 [min].

Alternative Synthesis:

d. 4-Chlorobenzyl alcohol (10.0 g, 70.1 mmol) is dissolved in DCM (200 ml), 1,1'-carbonyldiimidazole (11.9 g, 73.6 mmol) is added, and stirring is continued at RT for 3 h. tert-Butyl 1-piperazine-N-carboxylate (14.4 g, 77.1 mmol) is added to this mixture. Stirring is continued at RT for 18 h. The reaction mixture is diluted with DCM (100 ml), washed 2× with water, the organic phase is dried over sodium sulfate, filtered off and evaporated to dryness. The dried crude substance 5 (24.5 g, 69.0 mmol, 98%) is reacted further without further purification.

e. Compound 5 (6.5 g, 18.3 mmol) is taken up in 6N HCl in 2-propanol (100 ml), and stirring is continued at RT for 45 min. The precipitate is filtered off and dried, giving a colourless solid 6 (5.04 g, 17.3 mmol, 95%).

f. Compound 1 (3.88 g, 17.2 mmol) is initially introduced in DMF (200 ml), compound 5 (5.00 g, 17.2 mmol) and sodium hydrogencarbonate (5.77 g, 68.7 mmol) are added at RT g. tert-Butyl 1-piperazine-N-carboxylate (0.50 g, 2.69 mmol) is dissolved in DCM (10 ml), triethylamine (0.74 ml, 5.37 mmol) and subsequently 4-chlorophenoxyacetyl chloride (0.55 g, 2.69 mmol) are added at RT, and the mixture is stirred at RT for a further 15 h. The reaction mixture is diluted with DCM (40 ml), washed 2× with water, the organic phase is dried over sodium sulfate, filtered off and evaporated to dryness. The dried crude substance 7 (0.95 g, 2.67 mmol, 100%) is reacted further without further purification.

h. Analogously to e., compound 7 (0.95 g, 2.67 mmol) is taken up in 6N HCl in 2-propanol (10 ml), and stirring is continued at RT for 45 min. The crude substance is evaporated to dryness and dried and used without further purification, giving compound 8 (0.73 g, 2.50 mmol, 94%).

i. Analogously to f., compound 1 (0.35 g, 1.56 mmol) in DMF (10 ml) is reacted with compound 8 (0.46 g, 1.56 mmol) and sodium hydrogencarbonate (0.53 g, 6.25 mmol) at RT and stirred at RT for 2 days. The reaction solution is added to water (50 ml), and the precipitate which has formed is filtered off with suction, rinsed with water and dried in vacuo, giving compound "A2" (0.52 g, 1.17 mmol, 75%); [M+H$^+$] 445; Rt HPLC 3.39 [min].

Alternative Process:

j. 4-Chlorophenoxyacetyl chloride (0.50 g, 2.44 mmol) was dissolved in DMF (10 ml), and compound 3 (0.76 g, 2.44 mmol) was added at RT. Stirring was continued at RT for 18 h. Water (10 ml) was added to the reaction mixture, and the precipitate which had formed was filtered off. The latter was washed with water and dried (vacuum drying cabinet). The colourless solid obtained was likewise compound "A2" (0.96 g, 2.16 mmol, 89%);

$^1$H-NMR (DMSO-d$_6$): δ [ppm]=2.37-243 (m, 2H), 2.43-2.48 (m, 2H), 2.71 (t, 2H), 3.15-3.21 (m, 2H), 3.34-3.45 (m, 4H), 4.81 (s, 2H), 6.93 (d, 2H), 7.17 (d, 1H), 7.30 (d, 2H), 7.83-7.88 (m, 2H), 11.72 (s(b), 1H).

EXAMPLE 3

The preparation of 6-(3-{4-[2-(4-chlorophenyl)ethylsulfonyl]piperazin-1-yl}propionyl)-3H-benzoxazol-2-one ("A3"), N-(4-trifluoromethoxybenzyl) 4-[3-oxo-3-(2-oxo-2,3-dihydrobenzoxazol-6-yl)-propyl]piperazine-1-carboxamide ("A4"), 6-(3-{4-[3-(4-trifluoromethylphenyl)propionyl]piperazin-1-yl}propionyl)-3H-benzoxazol-2-one ("A5") is carried out analogously to the following scheme

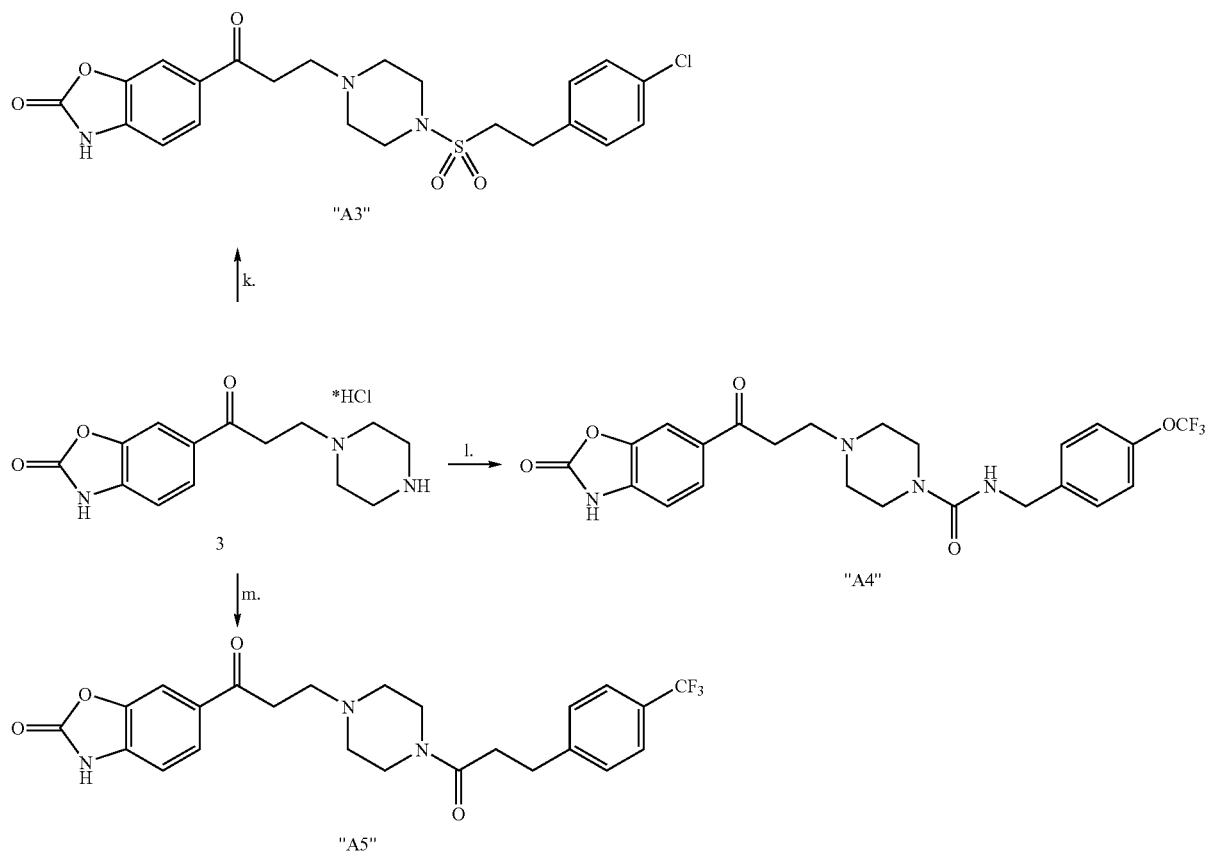

k. Compound 3 (0.50 g, 1.60 mmol) is dissolved in DMF (10 ml), triethylamine (0.49 g, 4.80 mmol) and subsequently 2-(4-chlorophenyl)ethylsulfonyl chloride (0.38 g, 1.60 mmol) are added at RT. Stirring is continued at RT for 18 h. Water (30 ml) is added to the reaction mixture, and the precipitate which has formed is filtered off. The latter is washed with water and dried (vacuum drying cabinet), giving compound "A3" (0.62 g, 1.30 mmol, 81%); [M+H$^+$]479.

l. Analogously to c., 4-trifluoromethoxybenzylamine (61.4 mg, 0.32 mmol) in DMF (2.5 ml) is reacted with 1,1'-carbonyldiimidazole (52.1 mg, 0.32 mmol) and compound 3 (100 mg, 0.32 mmol). Stirring is continued at RT for 18 h. Water (20 ml) is added to the reaction mixture, and the precipitate which has formed is filtered off. The latter is washed with water, recrystallised from MeOH/acetonitrile and dried (vacuum drying cabinet), giving "A4" (62.0 mg, 0.13 mmol, 39%); [M+H$^+$] 493; Rt HPLC 3.52 [min].

m. Compound 3 (0.15 g, 0.48 mmol) is dissolved in acetonitrile (10 ml), triethylamine (0.20 ml, 1.44 mmol) and subsequently 3-(4-trifluoromethyl-phenyl)propionyl chloride (114 mg, 0.48 mmol) are added at RT. Stirring is continued at 50° C. for 18 h. Water (50 ml) is added to the reaction mixture, and the precipitate which has formed is filtered off. The latter is washed with water and dried (vacuum drying cabinet), giving "A5" (143 mg, 0.30 mmol, 63%); [M+H$^+$] 476; Rt HPLC 3.63 [min];

$^1$H-NMR (DMSO-d$_6$): δ [ppm]=2.34 (s(b), 4H), 2.63-2.71 (m, 4H), 2.90 (t, 2H), 3.13-3.20 (m, 2H), 3.35-3.46 (m, 4H), 7.17 (d, 1H), 7.47 (d, 2H), 7.62 (d, 2H), 7.83-7.88 (m, 2H), 11.95 (s, 1H).

EXAMPLE 4

The preparation of 4-chlorobenzyl 4-[2-oxo-2-(2-oxo-2,3-dihydrobenzoxazol-6-yl)ethyl]piperazine-1-carboxylate ("A6") is carried out analogously to the following scheme

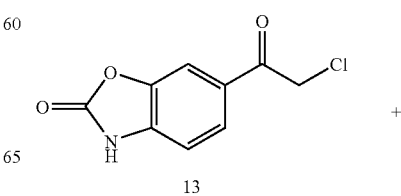

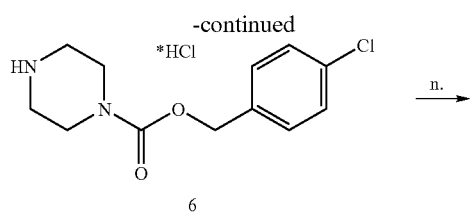

n. Compound 6 (150 mg, 0.52 mmol) is initially introduced in acetonitrile (5 ml), triethylamine (0.21 ml, 1.55 mmol) and compound 13 (116 mg, 0.55 mmol) are added at RT, and the mixture is stirred at 50° C. for 15 h. The reaction solution is evaporated to dryness and separated by preparative HPLC (Chromolith® prep, RP-18e, 100-25, with acetonitrile/water), giving compound "A6" (colourless solid, 63 mg, 0.15 mmol, 28%); [M+H⁺] 431; Rt HPLC 3.49 [min].

EXAMPLE 5

The preparation of N-(4-chlorobenzyl)-1-[3-oxo-3-(2-oxo-2,3-dihydrobenzoxazol-6-yl)propyl]piperidine-4-carboxamide ("A7") is carried out analogously to the following scheme o. 4-Chlorobenzylamine (0.27 ml, 2.18 mmol) and N-Boc-isonipecotinic acid (0.50 g, 2.18 mmol) are initially introduced in DMF (10 ml), N-(3-dimethylaminopropyl)-N'-ethylcarbodiimide hydrochloride (0.42 g, 2.18 mmol) and 1-hydroxybenzotriazole (0.29 g, 2.18 mmol) are added at RT, and the mixture is stirred at RT for 15 h. The reaction solution is poured into water, and the precipitate which has formed is filtered off. The latter is washed with water and dried (vacuum drying cabinet). The colourless product obtained was reacted without further purification (colourless solid 15, 0.68 g, 1.92 mmol, 88%).

p. Compound 15 (0.68 g, 2.18 mmol) is taken up in 6N HCl in 2-propanol (10 ml), and stirring is continued at RT for 1 h. The reaction solution is evaporated to dryness. The residue is triturated with ethyl acetate/diethyl ester, filtered off and dried, giving the colourless solid 16 (0.48 g, 1.68 mmol, 87%).

q. Compound 1 (100 mg, 0.44 mmol) is initially introduced in DMF (5 ml), and compound 16 (128 mg, 0.44 mmol) and subsequently sodium hydrogencarbonate (149 mg, 1.77 mmol) are added at RT. Stirring is continued at RT for 18 h. The reaction mixture is poured into water, and the precipitate which has formed is filtered off. The latter was washed with water and dried (vacuum drying cabinet). The residue is triturated with ethyl acetate/diethyl ether, filtered off again and dried, giving compound "A7" (112 mg, 0.25 mmol, 58%); [M+H⁺] 443; Rt HPLC 3.15 [min].

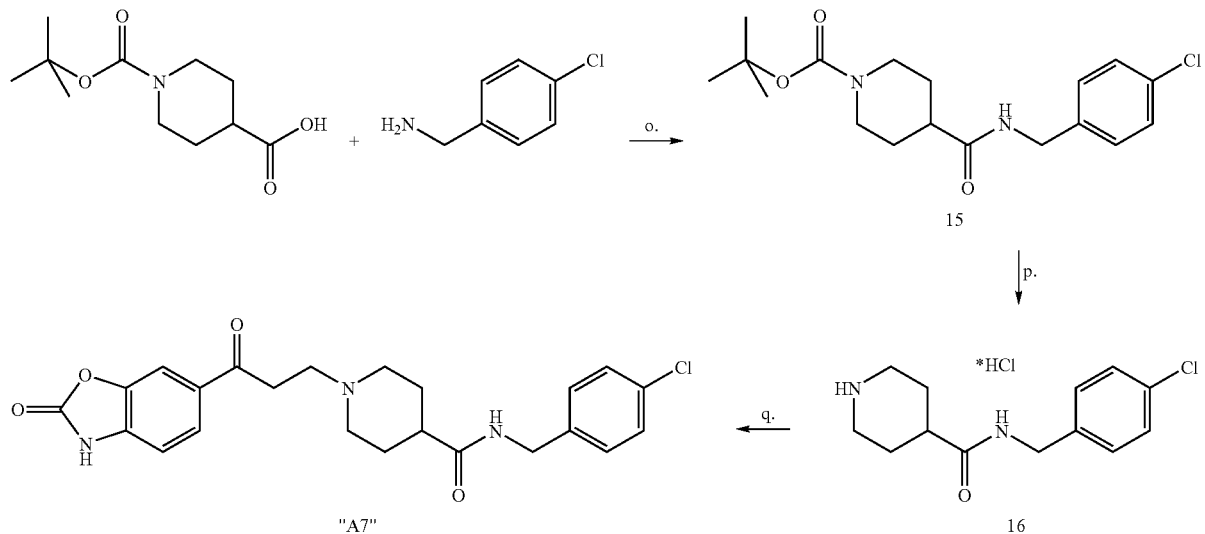

EXAMPLE 6

The preparation of

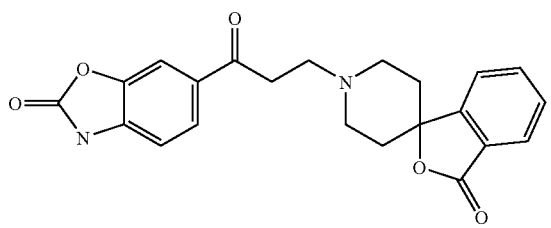

("A8")

is carried out analogously to the following scheme

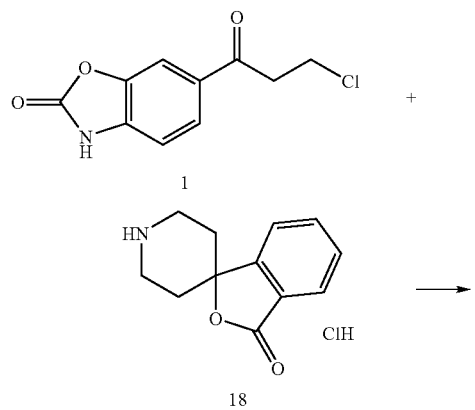

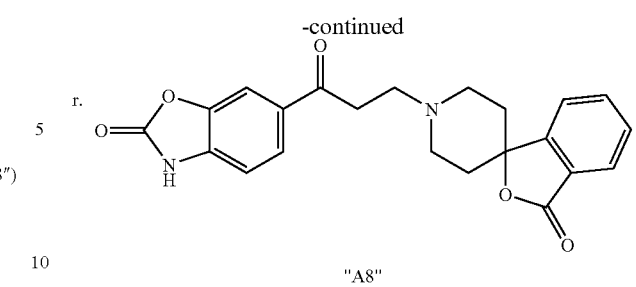

"A8"

r. Compound 1 (200 mg, 0.89 mmol) is initially introduced in DCM (7.5 ml), compound 18 (212 g, 0.89 mmol) and triethylamine (0.49 ml, 3.54 mmol) are added at RT, and the mixture is stirred at RT for 18 h. The reaction solution is evaporated to dryness, MeOH is added, the mixture is treated in an ultrasound bath for 2 min, filtered, and the residue is dried in vacuo, giving "A8" (209 mg, 0.53 mmol, 60%); [M+H$^+$] 393; Rt HPLC 2.72 [min].

Compound "A9"

"A9"

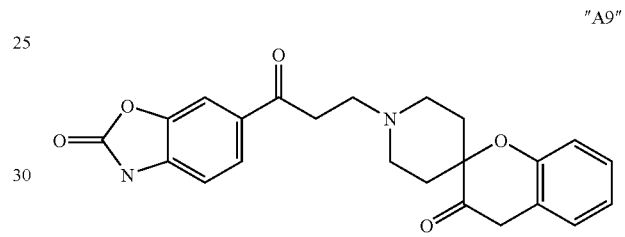

[M+H$^+$] 407, is obtained analogously.

The following compounds are obtained analogously to the above examples

| Compound No. | Name and/or structure | ESI [M + H]$^+$ | HPLC (RT in min) method |
|---|---|---|---|
| "A10" | 6-{3-[4-(2,3-Dihydrobenzo-1,4-dioxin-2-carbonyl)piperazin-1-yl]propionyl}-3H-benzoxazol-2-one | 438 | 3.07 |
| "A11" | 6-(3-{4-[2-(4-Fluorophenyl)ethyl]piperazin-1-yl}-propionyl)-3H-benzoxazol-2-one | 398 | |

| Compound No. | Name and/or structure | ESI [M + H]+ | HPLC (RT in min) method |
|---|---|---|---|
| "A12" | 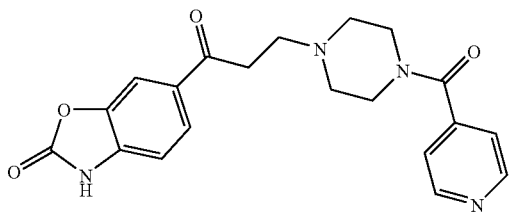<br>6-{3-[4-(Pyridine-4-carbonyl)piperazin-1-yl]-propionyl}-3H-benzoxazol-2-one | 381 | |
| "A13" | 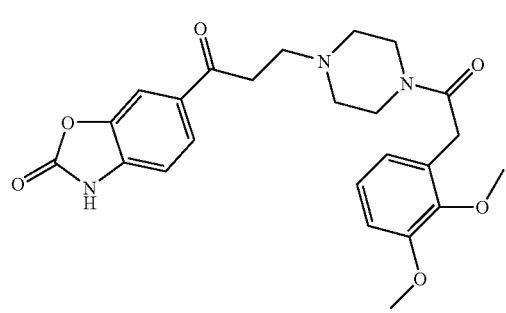<br>6-(3-{4-[2-(2,3-Dimethoxyphenyl)acetyl]-piperazin-1-yl}propionyl)-3H-benzoxazol-2-one | 454 | |
| "A14" | 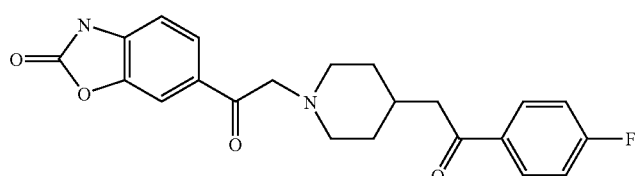<br>6-(2-{4-[2-(4-Fluorophenyl)-2-oxoethyl]piperidin-1-yl}acetyl)-3H-benzoxazol-2-one | 397 | |
| "A15" | 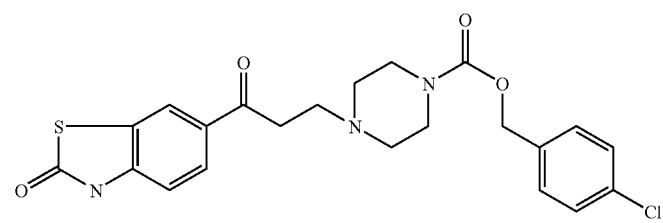<br>4-Chlorobenzyl 4-[3-oxo-3-(2-oxo-2,3-dihydro-benzothiazol-6-yl)propyl]piperazine-1-carboxylate | 461 | 3.49 |

1H-NMR (DMSO-d6) δ [ppm] = 2.38-2.44(m, 4H), 2.70(t, 2H), 3.17(t, 2H), 3.33-3.43(m, 4H), 5.06(s, 2H), 7.19(d, 1H), 7.38(d, 2H), 7.43(m, 2H), 7.91 (dd, 1H), 8.27(d, 1H), 12.07(s(b), 1H).

| | | | |
|---|---|---|---|
| "A16" | 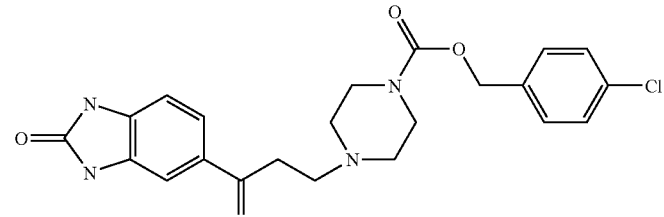<br>4-Chlorobenzyl 4-[3-oxo-3-(2-oxo-2,3-dihydro-1H-benzimidazol-5-yl)propyl]piperazine-1-carboxylate | 444 | 3.2 |

-continued

| Compound No. | Name and/or structure | ESI [M + H]+ | HPLC (RT in min) method |
|---|---|---|---|
| | ¹H-NMR (DMSO-d₆): δ [ppm] = 2.36-242(m, 4H), 2.69(t, 2H), 3.13(t, 2H), 3.37(s(b), 4H), 5.06(s, 2H), 7.00(d, 1H), 7.38(d, 2H), 7.43(d, 2H), 7.48(d, 1H), 7.68(dd, 1H), 10.90(s(b), 2H). | | |
| "A17" | 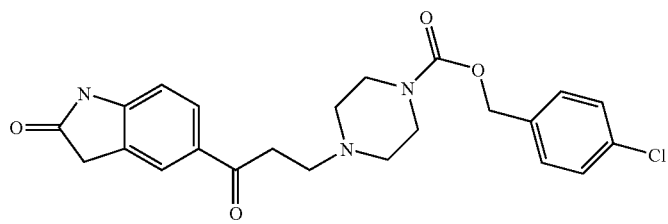<br>4-Chlorobenzyl 4-[3-oxo-3-(2-oxo-2,3-dihydro-1H-indol-5-yl)propyl]piperazine-1-carboxylate | 443 | 3.28 |
| "A18" | 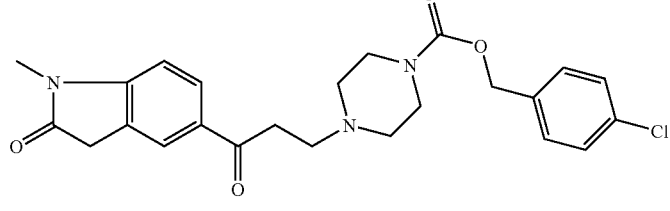<br>4-Chlorobenzyl 4-[3-(1-methyl-2-oxo-2,3-dihydro-1H-indol-5-yl)-3-oxopropyl]piperazine-1-carboxylate | 457 | 3.55 |
| "A19" | 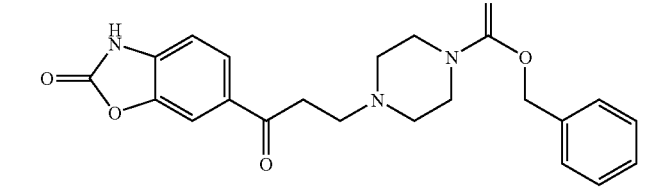<br>Benzyl 4-[3-oxo-3-(2-oxo-2,3-dihydro-benzoxazol-6-yl)propyl]piperazine-1-carboxylate | 410 | 3.09 |
| "A20" | 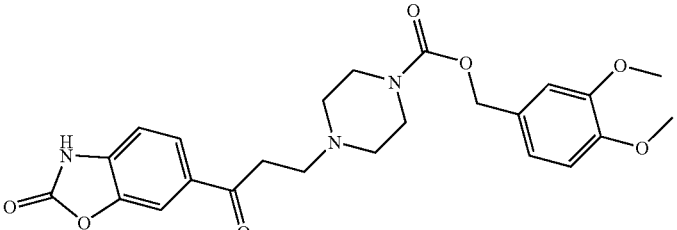<br>3,4-Dimethoxybenzyl 4-[3-oxo-3-(2,3-dihydrobenzoxazol-6-yl)propyl]piperazine-1-carboxylate | 470 | 2.77 |
| "A21" | 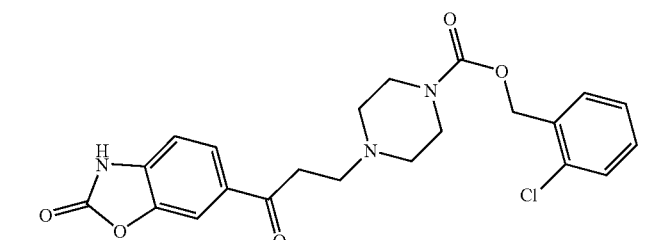<br>2-Chlorobenzyl 4-[3-oxo-3-(2-oxo-2,3-dihydro-benzoxazol-6-yl)propyl]piperazine-1-carboxylate | 445 | 3.41 |

-continued

| Compound No. | Name and/or structure | ESI [M + H]+ | HPLC (RT in min) method |
|---|---|---|---|
| "A22" | 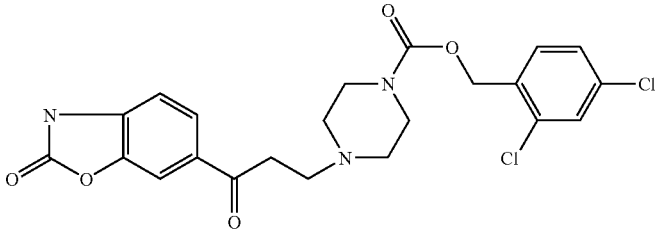<br>2,4-Dichlorobenzyl 4-[3-oxo-3-(2-oxo-2,3-dihydrobenzoxazol-6-yl)propyl]piperazine-1-carboxylate | 479 | 3.81 |
| "A23" | tert-Butylbenzyl 4-[3-oxo-3-(2-oxo-2,3-dihydro-benzoxazol-6-yl)propyl]piperazine-1-carboxylate | 467 | 4.21 |
| "A24" | 4-Methylbenzyl 4-[3-oxo-3-(2-oxo-2,3-dihydro-benzoxazol-6-yl)propyl]piperazine-1-carboxylate | 424 | 3.47 |
| "A25" | 4-Ethylbenzyl 4-[3-oxo-3-(2-oxo-2,3-dihydro-benzoxazol-6-yl)propyl]piperazine-1-carboxylate | 438 | 3.76 |
| "A26" | 3,4-Dimethylbenzyl 4-[3-oxo-3-(2-oxo-2,3-dihydrobenzoxazol-6-yl)propyl]piperazine-1-carboxylate | 438 | 3.65 |
| "A27" | 4-Chloro-2-methylbenzyl 4-[3-oxo-3-(2-oxo-2,3-dihydrobenzoxazol-6-yl)propyl]piperazine-1-carboxylate | 459 | 3.73 |
| "A28" | 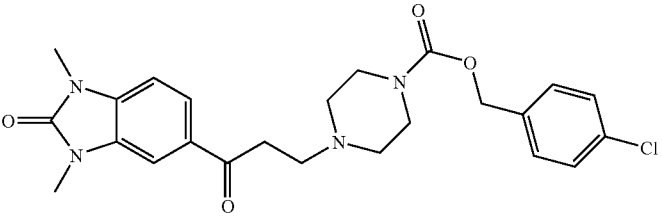<br>4-Chlorobenzyl 4-[3-(1,3-dimethyl-2-oxo-2,3-dihydro-1H-benzimidazol-5-yl)-3-oxopropyl]-piperazine-1-carboxylate | 472 | |
| "A29" | 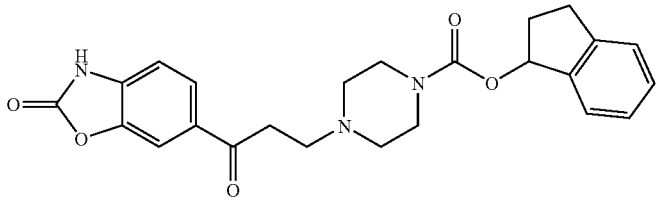<br>Indan-1-yl 4-[3-oxo-3-(2-oxo-2,3-dihydro-benzoxazol-6-yl)propyl]piperazine-1-carboxylate | 436 | 3.49 |
| "A30" | 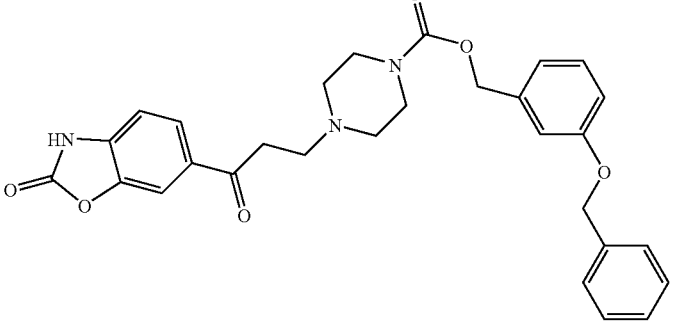<br>3-Benzyloxybenzyl 4-[3-oxo-3-(2-oxo-2,3-dihydrobenzoxazol-6-yl)propyl]piperazine-1-carboxylate | 517 | 4.16 |

-continued

| Compound No. | Name and/or structure | ESI [M + H]+ | HPLC (RT in min) method |
|---|---|---|---|
| "A31" | 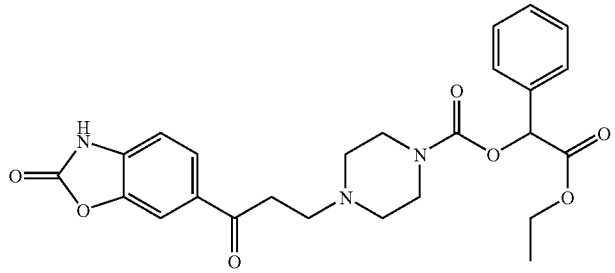<br>Ethoxycarbonylphenylmethyl 4-[3-oxo-3-(2-oxo-2,3-dihydrobenzoxazol-6-yl)propyl]piperazine-1-carboxylate | 483 | 3.57 |
| "A32" | 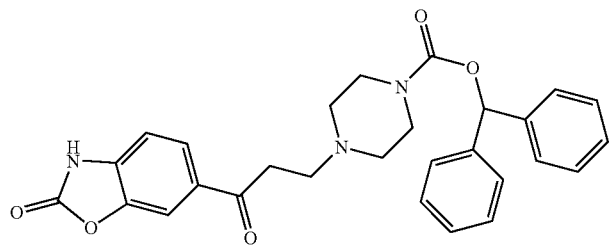<br>Benzohydryl 4-[3-oxo-3-(2-oxo-2,3-dihydro-benzoxazol-6-yl)propyl]piperazine-1-carboxylate | 487 | 3.97 |
| "A33" | 3-Methoxybenzyl 4-[3-oxo-3-(2-oxo-2,3-dihydro-benzoxazol-6-yl)propyl]piperazine-1-carboxylate | 440 | 3.23 |
| "A34" | 2-Methoxybenzyl 4-[3-oxo-3-(2-oxo-2,3-dihydro-benzoxazol-6-yl)propyl]piperazine-1-carboxylate | 440 | 3.25 |
| "A35" | 1-(4-Fluorophenyl)ethyl 4-[3-oxo-3-(2-oxo-2,3-dihydrobenzoxazol-6-yl)propyl]piperazine-1-carboxylate | 442 | 3.49 |
| "A36" | 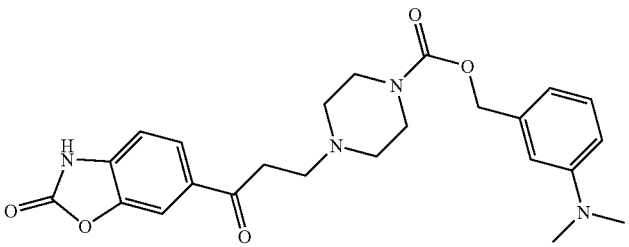<br>3-Dimethylaminobenzyl 4-[3-oxo-3-(2-oxo-2,3-dihydrobenzoxazol-6-yl)propyl]piperazine-1-carboxylate | 454 | 2.75 |
| "A37" | 4-Butoxybenzyl 4-[3-oxo-3-(2-oxo-2,3-dihydro-benzoxazol-6-yl)propyl]piperazine-1-carboxylate | 483 | 4.24 |
| "A38" | 4-Methoxybenzyl 4-[3-oxo-3-(2-oxo-2,3-dihydro-benzoxazol-6-yl)propyl]piperazine-1-carboxylate | 440 | 3.17 |
| "A39" | 4-Methoxycarbonylbenzyl 4-[3-oxo-3-(2-oxo-2,3-dihydrobenzoxazol-6-yl)propyl]piperazine-1-carboxylate | 468 | 3.12 |
| "A40" | 4-Trifluoromethylsulfanylbenzyl 4-[3-oxo-3-(2-oxo-2,3-dihydrobenzoxazol-6-yl)propyl]-piperazine-1-carboxylate | 511 | 4.11 |
| "A41" | 4-Isopropylbenzyl 4-[3-oxo-3-(2-oxo-2,3-dihydro-benzoxazol-6-yl)propyl]piperazine-1-carboxylate | 453 | 4.05 |

-continued

| Compound No. | Name and/or structure | ESI [M + H]+ | HPLC (RT in min) method |
|---|---|---|---|
| "A42" | 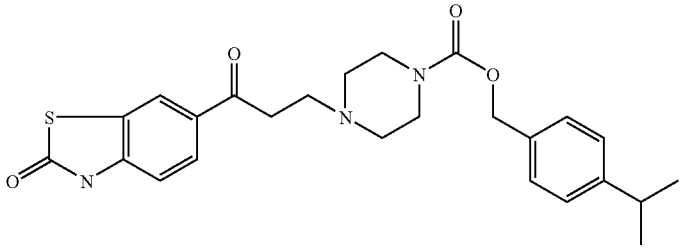<br>4-Isopropylbenzyl 4-[3-oxo-3-(2-oxo-2,3-dihydro-benzothiazol-6-yl)propyl]piperazine-1-carboxylate | 469 | 4.08 |
| "A43" | 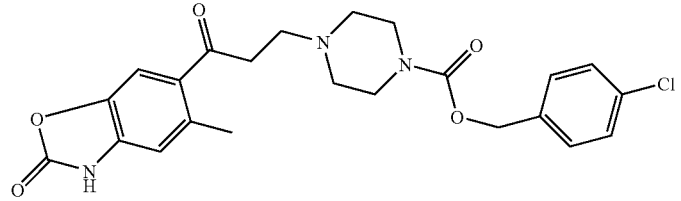<br>4-Chlorobenzyl 4-[3-(5-methyl-2-oxo-2,3-dihydro-benzoxazol-6-yl)-3-oxopropyl]piperazine-1-carboxylate | 459 | 3.71 |
| "A44" | 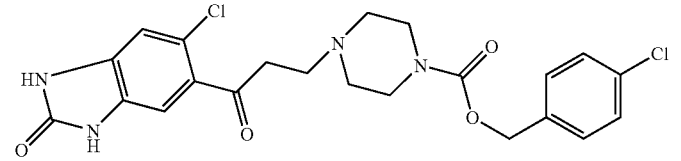<br>4-Chlorobenzyl 4-[3-(6-chloro-2-oxo-2,3-dihydro-1H-benzimidazol-5-yl)-3-oxopropyl]piperazine-1-carboxylate | 478 | 3.44 |
| "A45" | 3,4-Dichlorobenzyl 4-[3-oxo-3-(2-oxo-2,3-dihydrobenzoxazol-6-yl)porpyl]piperazine-1-carboxylate | 479 | 3.84 |
| "A46" | 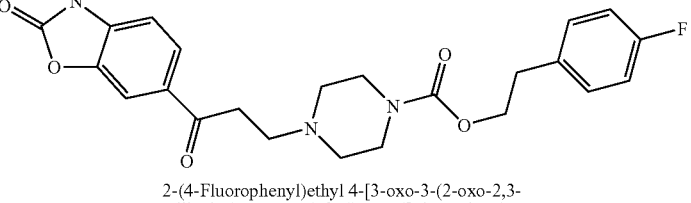<br>2-(4-Fluorophenyl)ethyl 4-[3-oxo-3-(2-oxo-2,3-dihydrobenzoxazol-6-yl)propyl]piperazine-1-carboxylate | 442 | 3.44 |
| "A47" | 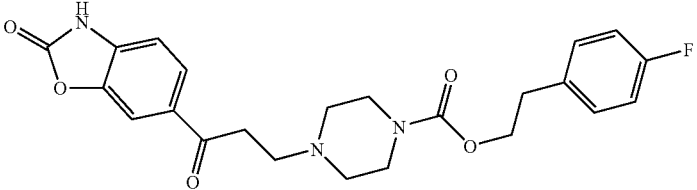<br>Chroman-4-yl 4-[3-oxo-3-(2-oxo-2,3-dihydro-benzoxazol-6-yl)propyl]piperazine-1-carboxylate | 452 | 3.36 |
| "A48" | 3-Chlorobenzyl 4-[3-oxo-3-(2-oxo-2,3-dihydro-benzoxazol-6-yl)propyl]piperazine-1-carboxylate | 445 | 3.55 |

-continued

| Compound No. | Name and/or structure | ESI [M + H]+ | HPLC (RT in min) method |
|---|---|---|---|
| "A49" | 3,5-Dichlorobenzyl 4-[3-oxo-3-(2-oxo-2,3-dihydrobenzoxazol-6-yl)propyl]piperazine-1-carboxylate | 479 | 3.92 |
| | 1H-NMR (DMSO-d6): δ [ppm] = 2.38-2.45(m, 4H), 2.64-2.74(m, 2H), 3.13-3.21(m, 2H), 3.28-3.42(m, 4H), 5.07(s, 2H), 7.16(d, 1H), 7.41(s, 2H), 7.56 (s, 1H), 7.82-7.88(m, 2H) | | |
| "A50" | 4-Trifluoromethylbenzyl 4-[3-oxo-3-(2-oxo-2,3-dihydrobenzoxazol-6-yl)propyl]piperazine-1-carboxylate | 478 | 3.79 |
| "A51" | 2-Fluoro-5-trifluoromethylbenzyl 4-[3-oxo-3-(2-oxo-2,3-dihydrobenzoxazol-6-yl)propyl]-piperazine-1-carboxylate | 496 | 3.76 |
| "A52" | 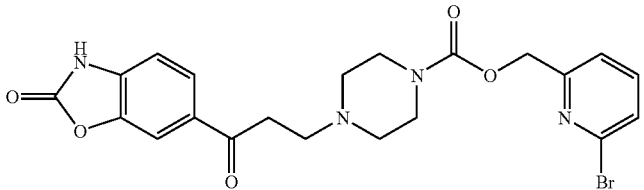<br>6-Bromopyridin-2-ylmethyl 4-[3-oxo-3-(2-oxo-2,3-dihydrobenzoxazol-6-yl)propyl]piperazine-1-carboxylate | 489, 491 | 2.8 |
| "A53" | 2-Fluoro-4-trifluoromethylbenzyl 4-[3-oxo-3-(2-oxo-2,3-dihydrobenzoxazol-6-yl)propyl]-piperazine-1-carboxylate | 496 | 3.84 |
| "A54" | 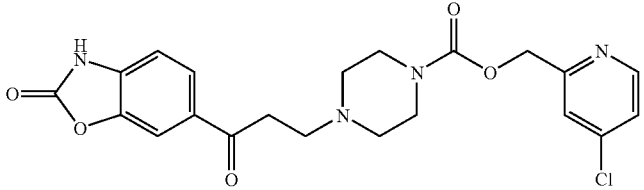<br>4-Chloropyridin-2-ylmethyl 4-[3-oxo-3-(2-oxo-2,3-dihydrobenzoxazol-6-yl)propyl]piperazine-1-carboxylate | 446 | 2.11 |
| "A55" | 4-Fluorobenzyl 4-[3-oxo-3-(2-oxo-2,3-dihydro-benzoxazol-6-yl)propyl]piperazine-1-carboxylate | 428 | 3.17 |
| "A56" | 4-Methyl-3-nitrobenzyl 4-[3-oxo-3-(2-oxo-2,3-dihydrobenzoxazol-6-yl)propyl]piperazine-1-carboxylate | 469 | 3.52 |
| "A57" | 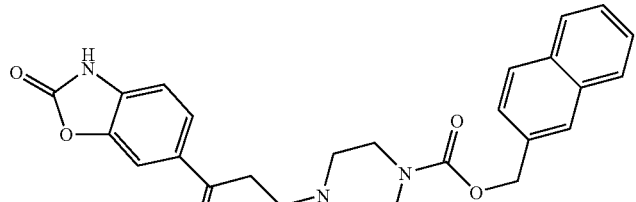<br>Naphthalen-2-ylmethyl 4-[3-oxo-3-(2-oxo-2,3-dihydrobenzoxazol-6-yl)propyl]piperazine-1-carboxylate | 460 | 3.76 |

-continued

| Compound No. | Name and/or structure | ESI [M + H]+ | HPLC (RT in min) method |
|---|---|---|---|
| "A58" | 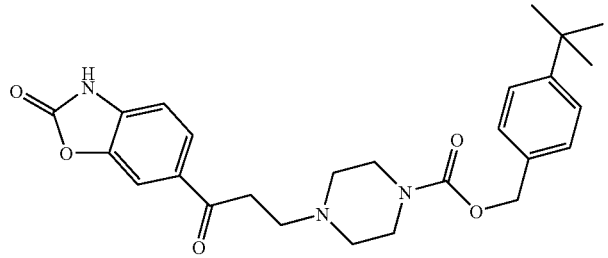  N-(4-tert-Butylbenzyl)-4-[3-oxo-3-(2-oxo-2,3-dihydrobenzoxazol-6-yl)propyl]piperazine-1-carboxamide | 466 | 3.79 |
| "A59" | N-(4-Chloro-3-trifluoromethylbenzyl)-4-[3-oxo-3-(2-oxo-2,3-dihydrobenzoxazol-6-yl)propyl]-piperazine-1-carboxamide | 512 | 3.65 |
| "A60" | N-(4-Cyanobenzyl)-4-[3-oxo-3-(2-oxo-2,3-dihydrobenzoxazol-6-yl)propyl]piperazine-1-carboxamide | 434 | 2.21 |
| "A61" | 2-(4-Bromophenyl)ethyl 4-[3-oxo-3-(2-oxo-2,3-dihydrobenzoxazol-6-yl)propyl]piperazine-1-carboxylate | 502, 504 | 3.73 |
| "A62" | Indan-2-yl 4-[3-oxo-3-(2-oxo-2,3-dihydro-benzoxazol-6-yl)propyl]piperazine-1-carboxylate | 436 | 3.47 |
| "A63" | 2-(4-Methoxyphenyl)ethyl 4-[3-oxo-3-(2-oxo-2,3-dihydrobenzoxazol-6-yl)propyl]piperazine-1-carboxylate | 454 | 3.33 |
| "A64" | Phenethyl 4-[3-oxo-3-(2-oxo-2,3-dihydro-benzoxazol-6-yl)propyl]piperazine-1-carboxylate | 424 | 3.28 |
| "A65" | 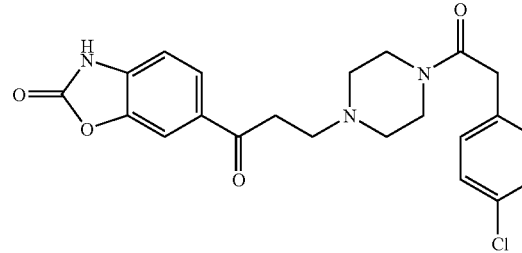  6-(3-{4-[2-(4-Chlorophenyl)acetyl]piperazin-1-yl}-propionyl)-3H-benzoxazol-2-one | 429 | 3.17 |
| "A66" | 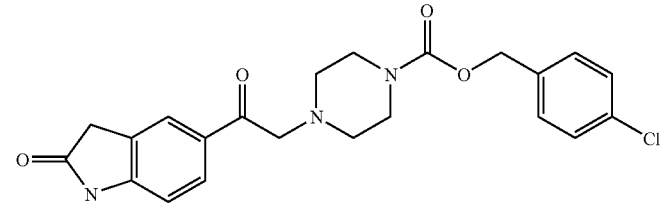  4-Chlorobenzyl 4-[2-oxo-2-(2-oxo-2,3-dihydro-1H-indol-5-yl)ethyl]piperazine-1-carboxylate | 429 | 3.25 |
| "A67" | 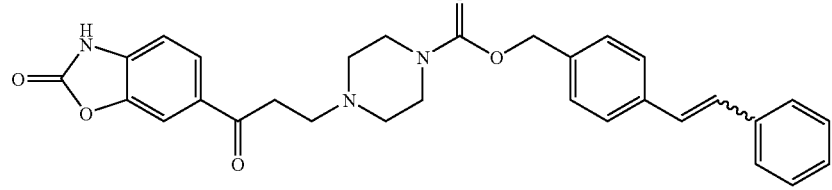  4-Styrylbenzyl 4-[3-oxo-3-(2-oxo-2,3-dihydro-benzoxazol-6-yl)propyl]piperazine-1-carboxylate | 513 | 4.32 |

-continued

| Compound No. | Name and/or structure | ESI [M + H]+ | HPLC (RT in min) method |
|---|---|---|---|
| "A68" | 4-Acetylaminobenzyl 4-[3-oxo-3-(2-oxo-2,3-dihydrobenzoxazol-6-yl)propyl]piperazine-1-carboxylate | 467 | 1.73 |
| "A69" | N-(4-Chlorobenzyl)-4-[3-oxo-3-(2-oxo-2,3-dihydrobenzoxazol-6-yl)propyl]piperazine-1-carboxamide | 444 | 2.91 |
| "A70" | 4-Methylsulfanylbenzyl 4-[3-oxo-3-(2-oxo-2,3-dihydrobenzoxazol-6-yl)propyl]piperazine-1-carboxylate | 457 | 3.65 |
| "A71" | 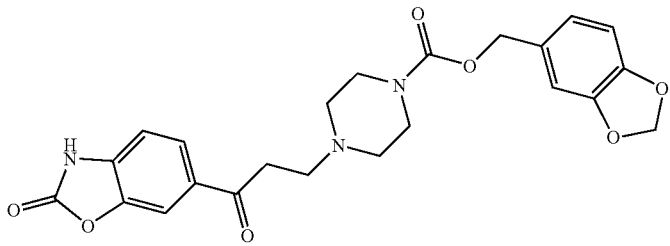Benzo-1,3-dioxol-5-ylmethyl 4-[3-oxo-3-(2-oxo-2,3-dihydrobenzoxazol-6-yl)propyl]piperazine-1-carboxylate | 454 | 3.12 |
| "A72" | 4-Trifluoromethoxybenzyl 4-[3-oxo-3-(2-oxo-2,3-dihydrobenzoxazol-6-yl)propyl]piperazine-1-carboxylate | 494 | 3.95 |
| "A73" | 4-Chlorobenzyl 4-[2-oxo-2-(2-oxo-2,3-dihydrobenzothiazol-6-yl)ethyl]piperazine-1-carboxylate | 447 | 3.52 |
| "A74" | 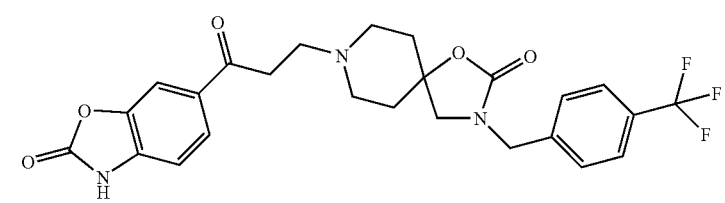8-[3-Oxo-3-(2-oxo-2,3-dihydrobenzoxazol-6-yl)-propyl]-3-(4-trifluoromethylbenzyl)-1-oxa-3,8-diazaspiro[4.5]decan-2-one | 504 | 3.68 |
| "A75" | 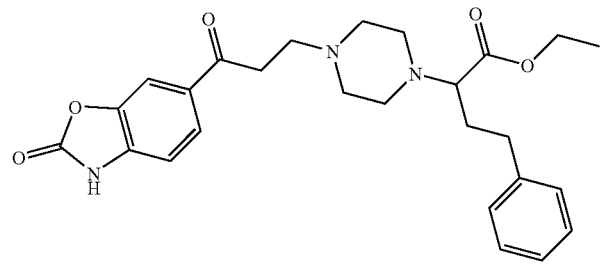Ethyl 2-{4-[3-oxo-3-(2-oxo-2,3-dihydro-benzoxazol-6-yl)propyl]piperazin-1-yl}-4-phenyl-butyrate | 467 | 4.08 |
| "A76" | 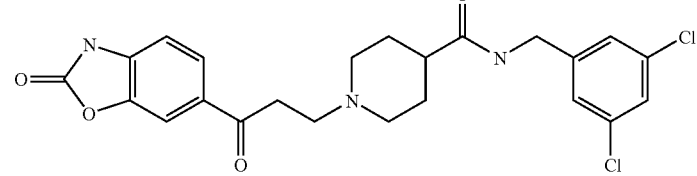N-(3,5-Dichlorobenzyl)-1-[3-oxo-3-(2-oxo-2,3-dihydrobenzoxazol-6-yl)propyl]piperidine-4-carboxamide | 477 | |

| Compound No. | Name and/or structure | ESI [M + H]+ | HPLC (RT in min) method |
|---|---|---|---|

¹H-NMR (DMSO-d₆): δ [ppm] = 1.51-1.62(m, 2H), 1.65-1.74(m, 2H), 1.94-2.03(m, 2H), 2.13-2.22(m, 1H), 2.63-2.72(m, 2H), 2.89-2.98(m, 2H), 3.12-3.21(m, 2H), 4.25(d, 2H), 7.14(d, 1H), 7.27(s, 1H), 7.47(s, 1H), 7.78-7.86 (m, 2H), 8.34(t, 1H).

"A77"

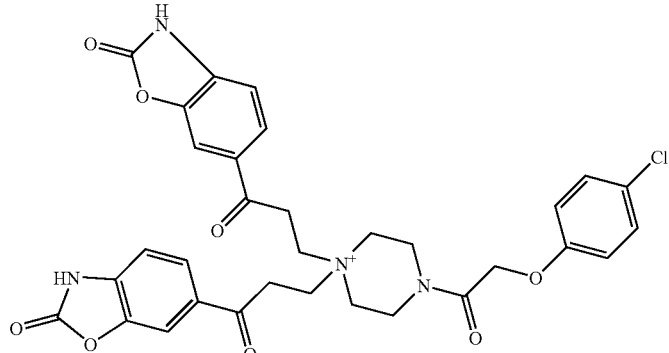

4-[2-(4-Chlorophenoxy)acetyl]-1,1-bis[3-oxo-3-(2-oxo-2,3-dihydrobenzoxazol-6-yl)propyl]-piperazin-1-ium

635

"A78"

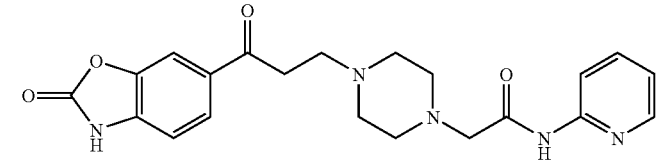

2-{3-Oxo-3-(2-oxo-2,3-dihydrobenzoxazol-6-yl)propyl]piperazin-1-yl}-N-pyridin-2-ylacetamide

410

"A79"

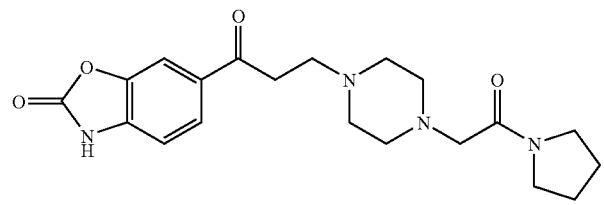

6-{3-[4-(2-Oxo-2-pyrrolidin-1-ylethyl)piperazin-1-yl]propionyl}-3H-benzoxazol-2-one

387

"A80"

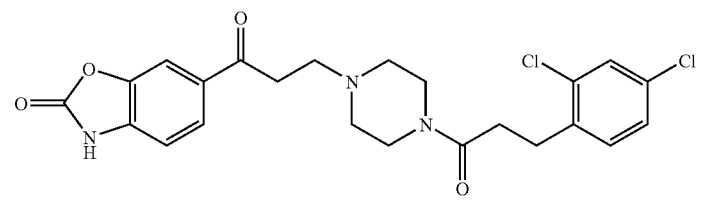

6-(3-{4-[3-(2,4-Dichlorophenyl)propionyl]-piperazin-1-yl}propionyl)-3H-benzoxazol-2-one

477

¹H-NMR (DMSO-d₆): δ [ppm] = 2.32-2.39(m, 4H), 2.60(t, 2H), 2.68(t, 2H), 2.89(t, 2H), 3.18(t, 2H), 3.35-3.46(m, 4H), 7.17(d, 1H), 7.35(dd, 1H), 7.41 (d, 1H), 7.56(d, 1H), 7.83-7.87(m, 2H), 11.75(s, 1H).

"A81"

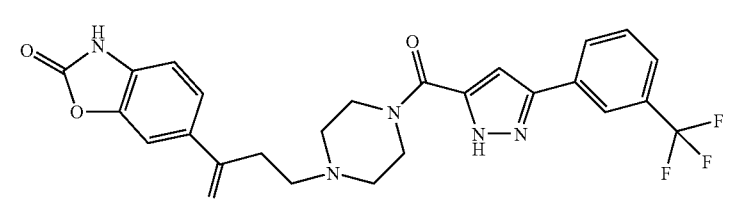

6-(3-{4-[5-(3-Trifluoromethylphenyl)-2H-pyrazole-3-carbonyl]piperazin-1-yl}propionyl)-3H-benzoxazol-2-one

514

| Compound No. | Name and/or structure | ESI [M + H]+ | HPLC (RT in min) method |
|---|---|---|---|
| "A82" | 6-{3-[4-(1-Oxo-2H-pyridin-1-ylmethyl)piperidin-1-yl]propionyl}-3H-benzoxazol-2-one | 382 | |
| "A83" | 6-{3-[4-(2-Dimethylamino-3-phenylpropionyl)-piperazin-1-yl]propionyl}-3H-benzoxazol-2-one | 452 | |

1H-NMR (DMSO-d6): δ [ppm] = 2.27(s, 6H), 2.30-2.37(m, 2H), 2.58(t, 2H), 2.73-2.80(m, 1H), 2.97-3.03(m, 3H), 3.11(t, 2H), 3.34-3.43(m, 4H), 5.82 (s(b), 1H), 7.11-7.26(m, 6H), 7.80-7.84(m, 2H), 11.25(s, 1H).

| Compound No. | Name and/or structure | ESI [M + H]+ | HPLC (RT in min) method |
|---|---|---|---|
| "A84" | tert-Butyl ((S)-1-(4-chlorobenzyl)-2-oxo-2-{4-[3-oxo-3-(2-oxo-2,3-dihydrobenzoxazol-6-yl)-propyl]piperazin-1-yl}ethyl)carbamate | 558 | |
| "A85" | 6-(3-{4-[(S)-2-Amino-3-(4-chlorophenyl)-propionyl]piperazin-1-yl}propionyl)-3H-benzoxazol-2-one | 458 | |
| "A86" | 5-Bromopyridin-3-ylmethyl 4-[3-oxo-3-(2-oxo-2,3-dihydrobenzoxazol-6-yl)propyl]piperazine-1-carboxylate | 489, 491 | |

-continued

| Compound No. | Name and/or structure | ESI [M + H]+ | HPLC (RT in min) method |
|---|---|---|---|
| "A87" | 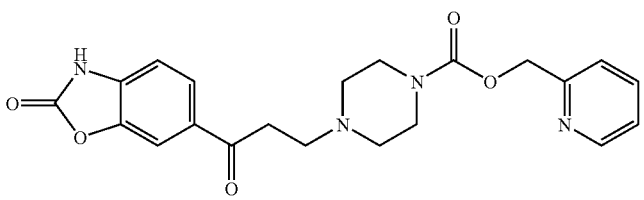<br>Pyridin-2-ylmethyl 4-[3-oxo-3-(2-oxo-2,3-dihydrobenzoxazol-6-yl)propyl]piperazine-1-carboxylate | 411 | |
| "A88" | 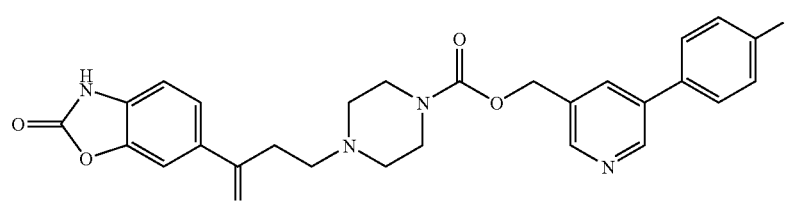<br>5-(4-Fluorophenyl)pyridin-3-ylmethyl 4-[3-oxo-3-(2-oxo-2,3-dihydrobenzoxazol-6-yl)propyl]-piperazine-1-carboxylate | 506 | |
| "A89" | Pyridin-3-ylmethyl 4-[3-oxo-3-(2-oxo-2,3-dihydrobenzoxazol-6-yl)propyl]piperazine-1-carboxylate | 411 | |
| "A90" | 6-Chloropyridin-3-ylmethyl 4-[3-oxo-3-(2-oxo-2,3-dihydrobenzoxazol-6-yl)propyl]piperazine-1-carboxylate | 446 | |
| "A91" | 2-Chloropyridin-4-ylmethyl 4-[3-oxo-3-(2-oxo-2,3-dihydrobenzoxazol-6-yl)propyl]piperazine-1-carboxylate | 446 | |
| "A92" | N-(3,5-Dichlorobenzyl)-4-[3-oxo-3-(2-oxo-2,3-dihydrobenzoxazol-6-yl)propyl]piperazine-1-carboxamide | 478 | |
| "A93" | 2-Trifluoromethoxybenzyl 4-[3-oxo-3-(2-oxo-2,3-dihydrobenzoxazol-6-yl)propyl]piperazine-1-carboxylate | 494 | |
| "A94" | 3,4,5-Trimethoxybenzyl 4-[3-oxo-3-(2-oxo-2,3-dihydrobenzoxaozl-6-yl)propyl]piperazine-1-carboxylate | 501 | |
| "A95" | 3-Trifluoromethylsulfanylbenzyl 4-[3-oxo-3-(2-oxo-2,3-dihydrobenzoxazol-6-yl)propyl]-piperazine-1-carboxylate | 510 | |
| "A96" | Furan-2-ylmethyl 4-[3-oxo-3-(2-oxo-2,3-dihydrobenzoxazol-6-yl)propyl]piperazine-1-carboxylate | 400 | |
| "A97" | 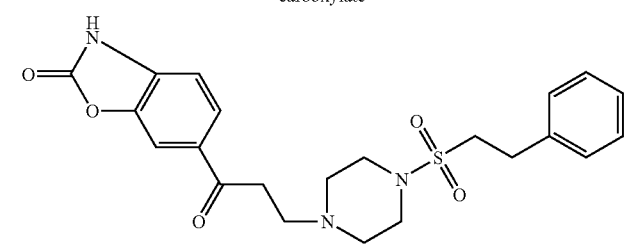<br>6-{3-[4-(2-Phenylethylsulfonyl)piperazin-1-yl]-propionyl}-3H-benzoxazol-2-one | 445 | |

-continued

| Compound No. | Name and/or structure | ESI [M + H]+ | HPLC (RT in min) method |
|---|---|---|---|
| "A98" | 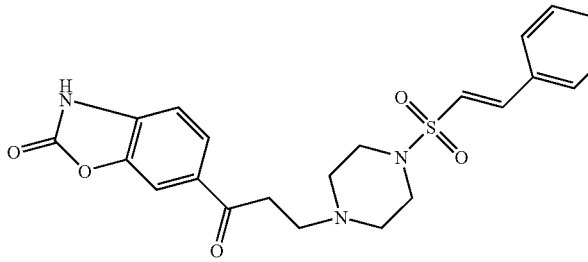<br>6-{3-[4-((E)-2-Phenylethenesulfonyl)piperazin-1-yl]propionyl}-3H-benzoxazol-2-one | 443 | |
| "A99" | 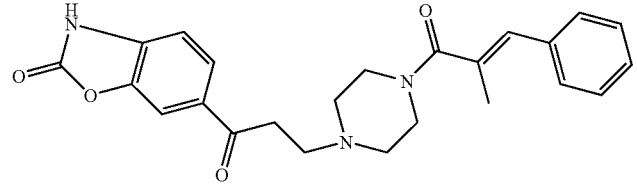<br>6-{3-[4-((E)-2-Methyl-3-phenylacryloyl)-piperazin-1-yl]propionyl}-3H-benzoxazol-2-one | 420 | |
| "A100" | 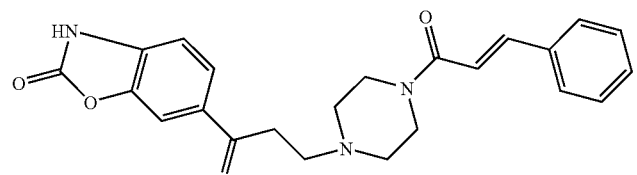<br>6-(3-{4-[(E)-(3-Phenylacryloyl)]piperazin-1-yl}-propionyl)-3H-benzoxazol-2-one | 406 | |
| "A101" | 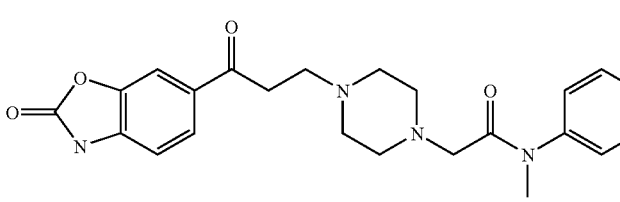<br>N-Methyl-2-{4-[3-oxo-3-(2-oxo-2,3-dihydro-benzoxazol-6-yl)propyl]piperazin-1-yl}-N-phenylacetamide | 423 | |
| "A102" | 3,5-Bistrifluoromethylbenzyl 4-[3-oxo-3-(2-oxo-2,3-dihydrobenzoxazol-6-yl)propyl]piperazine-1-carboxylate | 546 | |
| "A103" | 3-Chloro-5-trifluoromethylbenzyl 4-[3-oxo-3-(2-oxo-2,3-dihydrobenzoxazol-6-yl)propyl]-piperazine-1-carboxylate | 513 | |
| "A104" | 3,5-Dimethoxybenzyl 4-[3-oxo-3-(2-oxo-2,3-dihydrobenzoxazol-6-yl)propyl]piperazine-1-carboxylate | 470 | |
| "A105" | 3,5-Dimethylbenzyl 4-[3-oxo-3-(2-oxo-2,3-dihydrobenzoxazol-6-yl)propyl]piperazine-1-carboxylate | 438 | |
| "A106" | 3,5-Dibromobenzyl 4-[3-oxo-3-(2-oxo-2,3-dihydrobenzoxazol-6-yl)propyl]piperazine-1-carboxylate | 565, 567, 569 | |
| "A107" | 3-Fluoro-5-trifluoromethylbenzyl 4-[3-oxo-3-(2-oxo-2,3-dihydrobenzoxazol-6-yl)propyl]-piperazine-1-carboxylate | 496 | |
| "A108" | 3-Chloro-5-fluorobenzyl 4-[3-oxo-3-(2-oxo-2,3-dihydrobenzoxazol-6-yl)propyl]piperazine-1-carboxylate | 463 | |

| Compound No. | Name and/or structure | ESI [M + H]+ | HPLC (RT in min) method |
|---|---|---|---|
| "A109" | 3-Trifluoromethylbenzyl 4-[3-oxo-3-(2-oxo-2,3-dihydrobenzoxazol-6-yl)propyl]piperazine-1-carboxylate | 478 | |
| "A110" | 3,5-Difluorobenzyl 4-[3-oxo-3-(2-oxo-2,3-dihydrobenzoxazol-6-yl)propyl]piperazine-1-carboxylate | 446 | |
| "A111" | 2-Fluorobenzyl 4-[3-oxo-3-(2-oxo-2,3-dihydro-benzoxazol-6-yl)propyl]piperazine-1-carboxylate | 428 | |
| "A112" | 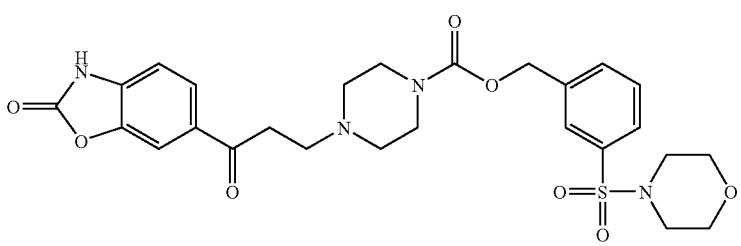<br>3-(Morpholine-4-sulfonyl)benzyl-4-[3-oxo-3-(2-oxo-2,3-dihydrobenzoxazol-6-yl)propyl]-piperazine-1-carboxylate | 560 | |
| "A131" | 4-Cyanobenzyl 4-[3-oxo-3-(2-oxo-2,3-dihydro-benzoxazol-6-yl)propyl]piperazine-1-carboxylate | 435 | |
| "A114" | 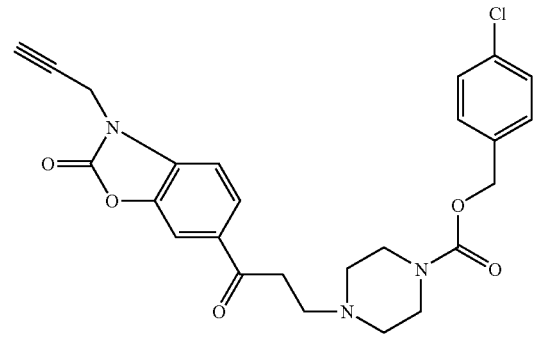<br>4-Chlorobenzyl 4-[3-oxo-3-(2-oxo-3-prop-2-ynyl-2,3-dihydrobenzoxazol-6-yl)propyl]-piperazine-1-carboxylate | 483 | |
| "A115" | 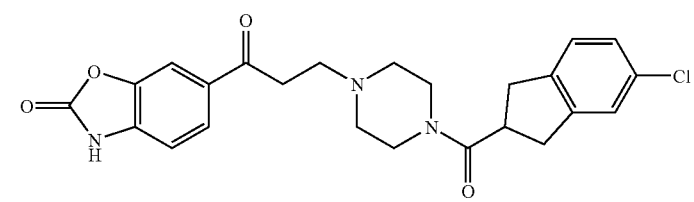<br>6-{3-[4-(5-Chloroindane-2-carbonyl)piperazin-1-yl]propionyl}-3H-benzoxazol-2-one | 455 | |
| "A116" | 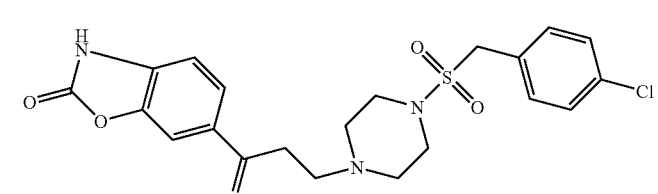<br>6-{3-[4-(4-Chlorophenylmethanesulfonyl)-piperazin-1-yl]propionyl}-3H-benzoxazol-2-one | 465 | |

| Compound No. | Name and/or structure | ESI [M + H]+ | HPLC (RT in min) method |
|---|---|---|---|
| "A117" | 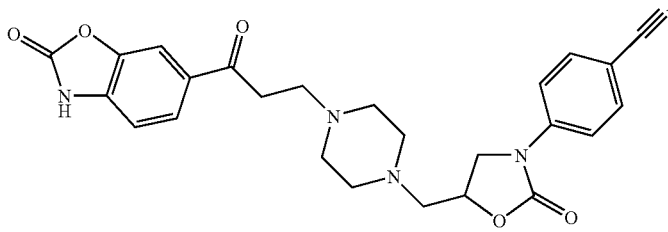<br>4-(2-Oxo-5-{4-[3-oxo-3-(2-oxo-2,3-dihydro-benzoxazol-6-yl)propyl]piperazin-1-ylmethyl}-oxazolidin-3-yl)benzontrile | 476 | |
| "A118" | 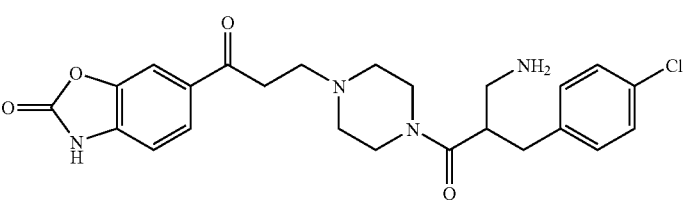<br>6-(3-{4-[2-Aminomethyl-3-(4-chlorophenyl)-propionyl]piperazin-1-yl}propionyl)-3H-benzoxazol-2-one | 472 | |
| "A119" | 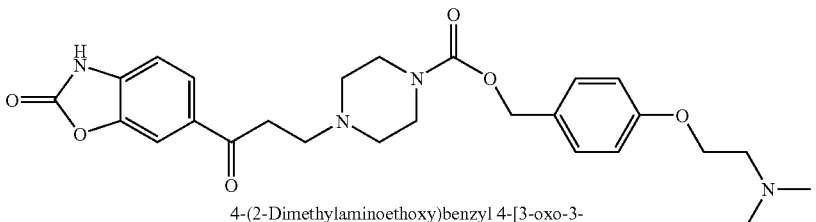<br>4-(2-Dimethylaminoethoxy)benzyl 4-[3-oxo-3-(2-oxo-2,3-dihydrobenzoxazol-6-yl)propyl]-piperazine-1-carboxylate | 498 | |
| "A120" | 2,4,6-Trimethylbenzyl 4-[3-oxo-3-(2-oxo-2,3-dihydrobenzoxazol-6-yl)propyl]piperazine-1-carboxylate | 453 | |
| "A121" | 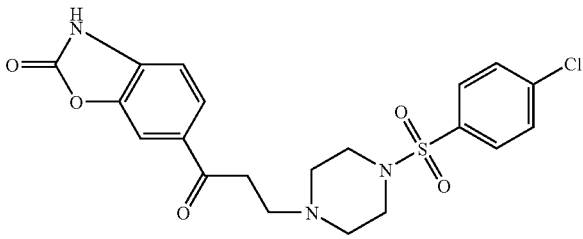<br>6-{3-[4-(4-Chlorobenzenesulfonyl)piperazin-1-yl]propionyl}-3H-benzoxazol-2-one | 451 | |
| "A122" | 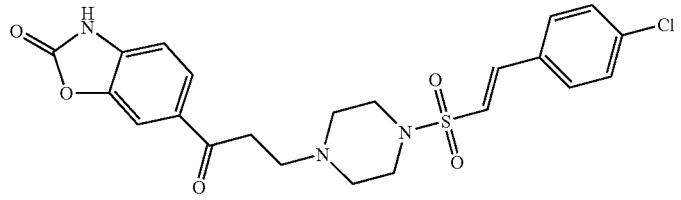<br>6-(3-{4-[((E)-2-(4-Chlorophenyl)ethenesulfonyl]-piperazin-1-yl}propionyl)-3H-benzoxazol-2-one | 477 | |

| Compound No. | Name and/or structure | ESI [M + H]+ | HPLC (RT in min) method |
|---|---|---|---|
| "A123" | 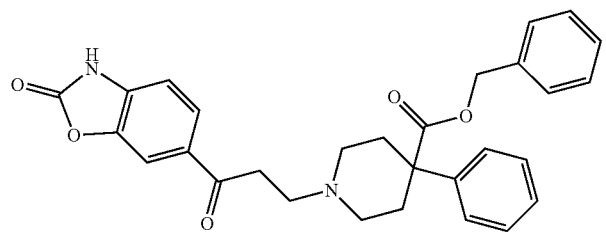<br>Benzyl 1-[3-oxo-3-(2-oxo-2,3-dihydro-benzoxazol-6-yl)propyl]-4-phenylpiperidine-4-carboxylate | 486 | |
| "A124" | 3-Cyanobenzyl 4-[3-oxo-3-(2-oxo-2,3-dihydro-benzoxazol-6-yl)propyl]piperazine-1-carboxylate | 435 | |
| "A125" | 6-(3-{4-[2-(3,5-Difluorophenyl)acetyl]piperazin-1-yl}propionyl)-3H-benzoxazol-2-one | 430 | |
| "A126" | 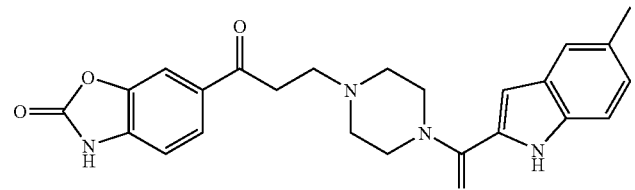<br>6-{3-[4-(5-Methyl-1H-indole-2-carbonyl)-piperazin-1-yl]propionyl}-3H-benzoxazol-2-one | 433 | |
| "A127" | 6-{3-[4-(5-Chloro-1H-indole-2-carbonyl)-piperazin-1-yl]propionyl}-3H-benzoxazol-2-one | 454 | |
| "A128" | 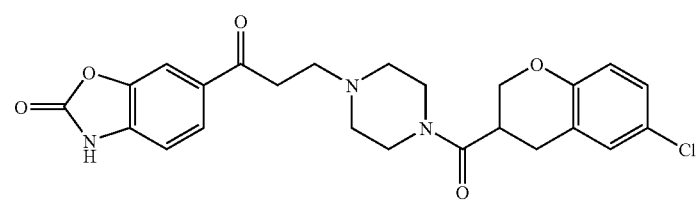<br>6-{3-[4-(6-Chlorochroman-3-carbonyl)-piperazin-1-yl]propionyl}-3H-benzoxazol-2-one | 471 | |
| "A129" | 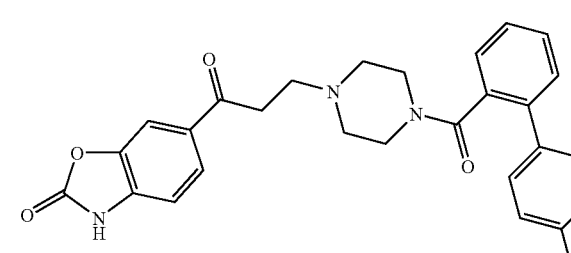<br>6-{3-[4-(4'-Methylbiphenyl-2-carbonyl)-piperazin-1-yl]propionyl}-3H-benzoxazol-2-one | 471 | |

-continued

| Compound No. | Name and/or structure | ESI [M + H]+ | HPLC (RT in min) method |
|---|---|---|---|
| "A130" | 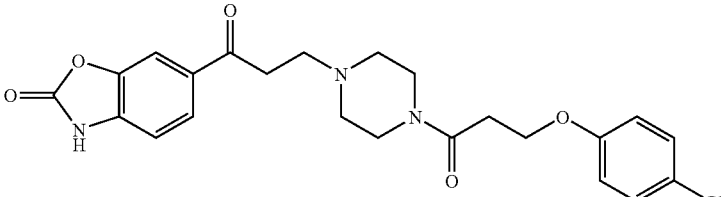<br>6-(3-{4-[3-(4-Chlorophenoxy)propionyl]-piperazin-1-yl}propionyl)-3H-benzoxazol-2-one | 459 | |

The following compounds can be prepared using methods known to the person skilled in the art. They are preferably prepared by the synthetic methods from Example 1 to 6 of the above-mentioned compounds:

| Compound No. | Name and/or structure | ESI [M + H]+ | HPLC (RT in min) method |
|---|---|---|---|
| "B1" | 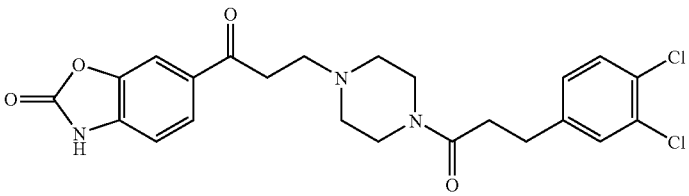 [SMILES: O=C(CCN1CCN(C(=O)CCc2ccc(Cl)c(Cl)c2)CC1)c1ccc2[nH]c(=O)oc2c1]<br>6-(3-{4-[3-(3,4-Dichlorophenyl)propionyl]-piperazin-1-yl}propionyl)-3H-benzoxazol-2-one | 477 | 3.55 |
| "B2" | 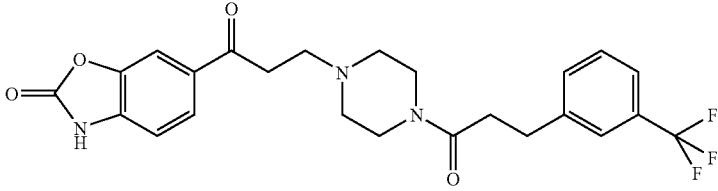 [SMILES: O=C(CCN1CCN(C(=O)CCc2cccc(C(F)(F)F)c2)CC1)c1ccc2[nH]c(=O)oc2c1]<br>6-(3-{4-[3-(3-Trifluoromethylphenyl)propionyl]-piperazin-1-yl}propionyl)-3H-benzoxazol-2-one | 476 | 3.36 |
| "B3" | 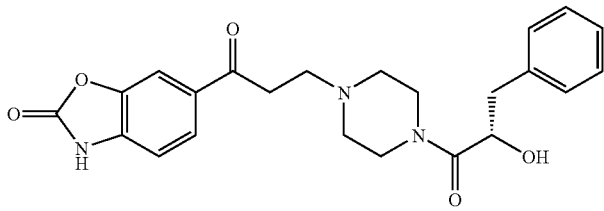 [SMILES: O=C(CCN1CCN(C(=O)[C@@H](O)Cc2ccccc2)CC1)c1ccc2[nH]c(=O)oc2c1]<br>6-{3-[4-((S)-2-Hydroxy-3-phenylpropionyl)-piperazin-1-yl]propionyl}-3H-benzoxazol-2-one | 424 | 2.43 |
| "B4" | 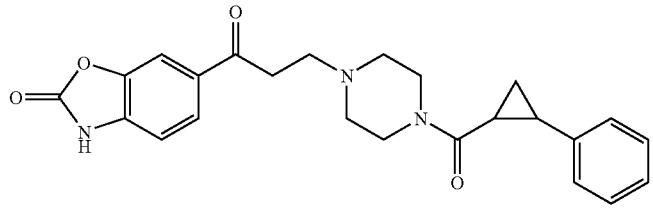 [SMILES: O=C(CCN1CCN(C(=O)C2CC2c2ccccc2)CC1)c1ccc2[nH]c(=O)oc2c1]<br>6-{3-[4-(2-Phenylcyclopropanecarbonyl)-piperazin-1-yl]propionyl}-3H-benzoxazol-2-one | 420 | 3.15 |

-continued

| Compound No. | Name and/or structure | ESI [M + H]+ | HPLC (RT in min) method |
|---|---|---|---|
| "B5" | 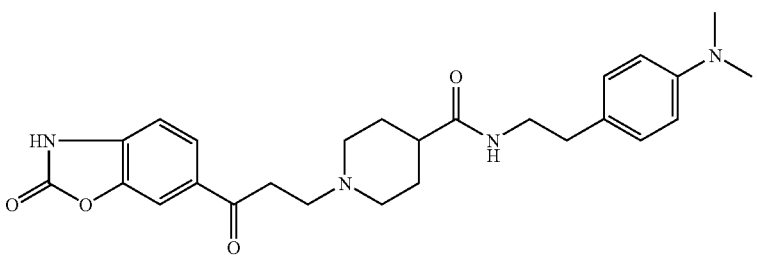 [SMILES: CN(C)c1ccc(CCNC(=O)C2CCN(CCC(=O)c3ccc4[nH]c(=O)oc4c3)CC2)cc1] N-[2-(4-Dimethylaminophenyl)ethyl]-1-[3-oxo-3-(2-oxo-2,3-dihydrobenzooxazol-6-yl)propyl]-piperidine-4-carboxamide | 466 | 1.15 |
| "B6" | 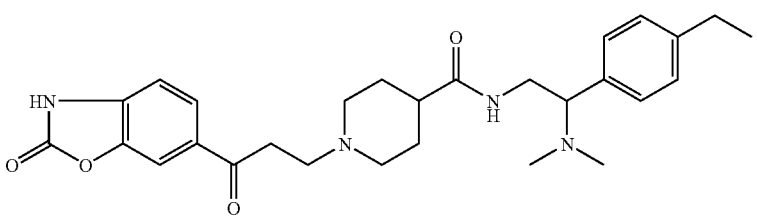 [SMILES: CCc1ccc(C(CNC(=O)C2CCN(CCC(=O)c3ccc4[nH]c(=O)oc4c3)CC2)N(C)C)cc1] N-[2-Dimethylamino-2-(4-ethylphenyl)ethyl]-1-[3-oxo-3-(2-oxo-2,3-dihydrobenzoxazol-6-yl)propyl]-piperidine-4-carboxamide | 494 | 2.85 |
| "B7" | 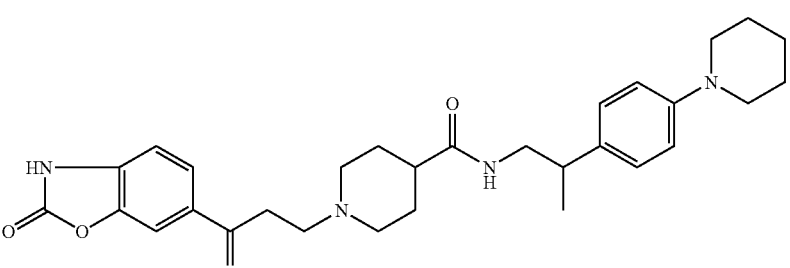 N-[2-(4-Piperidin-1-ylphenyl)propyl]-1-[3-oxo-3-(2-oxo-2,3-dihydrobenzoxazol-6-yl)propyl]-piperidine-4-carboxamide | 520 | 1.49 |
| "B8" | 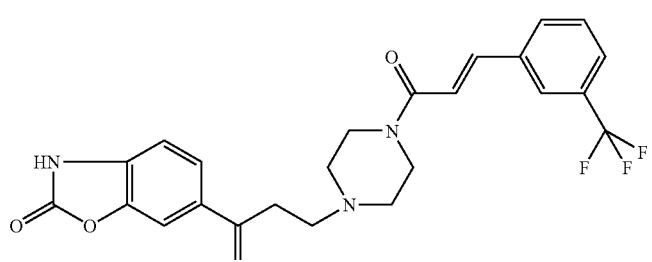 6-(3-{4-[(E)-3-(3-Trifluoromethylphenyl)acryloyl]-piperazin-1-yl}propionyl)-3H-benzoxazol-2-one | 474 | 2.36 |

| Compound No. | Name and/or structure | ESI [M + H]+ | HPLC (RT in min) method |
|---|---|---|---|
| "B9" | 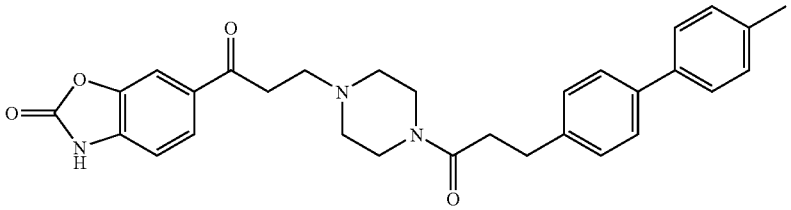 [SMILES: Cc1ccc(-c2ccc(CCC(=O)N3CCN(CCC(=O)c4ccc5[nH]c(=O)oc5c4)CC3)cc2)cc1]  6-{3-[4-(4'-Methylbiphenyl-4-carbonyl)piperazin-1-yl]propionyl}-3H-benzoxazol-2-one | 471 | 3.68 |
| "B10" | 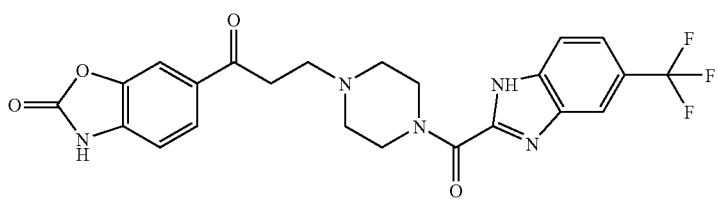 [SMILES: O=C(CCN1CCN(C(=O)c2nc3cc(C(F)(F)F)ccc3[nH]2)CC1)c1ccc2[nH]c(=O)oc2c1]  6-{3-[4-(5-Trifluoromethyl-1H-benzoimidazole-2-carbonyl)piperazin-1-yl]propionyl}-3H-benzoxazol-2-one | 488 | 3.28 |
| "B11" | 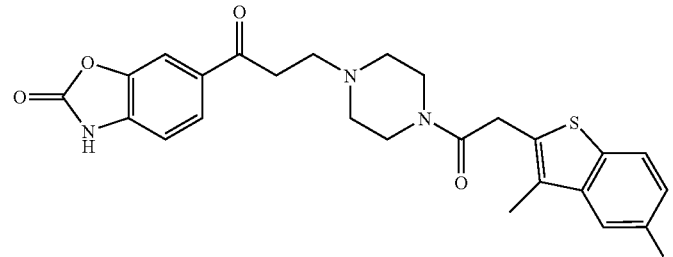  6-(3-{4-[2-(5-Chloro-3-methylbenzo[b]thiophen-2-yl)acetyl]piperazin-1-yl}propionyl)-3H-benzoxazol-2-one | 499 | 3.73 |
| "B12" | 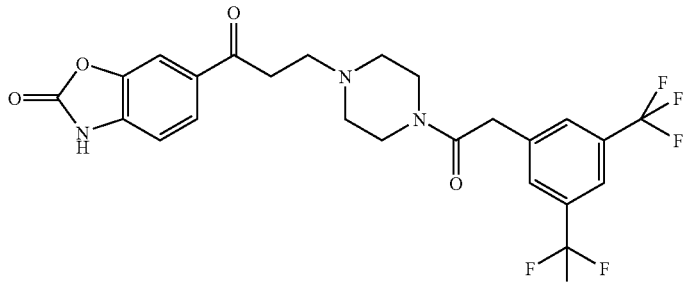  6-(3-{4-[2-(3,5-Bistrifluoromethylphenyl)acetyl]-piperazin-1-yl}propionyl)-3H-benzoxazol-2-one | 530 | 3.68 |

-continued

| Compound No. | Name and/or structure | ESI [M + H]+ | HPLC (RT in min) method |
|---|---|---|---|
| "B13" | 1-(3,5-Dichlorophenyl)-4-{4-[3-oxo-3-(2-oxo-2,3-dihydrobenzoxazol-6-yl)propyl]piperazin-1-yl}-butane-1,4-dione | 505 | 3.52 |
| "B14" | 5,6-Dichloro-2-(2-oxo-2-{4-[3-oxo-3-(2-oxo-2,3-dihydrobenzoxazol-6-yl)propyl]piperazin-1-yl}-ethyl)isoindole-1,3-dione | 532 | 3.47 |
| "B15" | 6-(3-{4-[4-Methyl-2-(4-trifluoromethylphenyl)-thiazole-5-carbonyl]piperazin-1-yl}propionyl)-3H-benzoxazol-2-one | 546 | 3.73 |
| "B16" | 6-(3-{4-[3-(4-Trifluoromethylphenyl)thiophene-2-carbonyl]piperazin-1-yl}propionyl)-3H-benzoxazol-2-one | 531 | 3.57 |

-continued
| Compound No. | Name and/or structure | ESI [M + H]+ | HPLC (RT in min) method |
|---|---|---|---|
| "B17" | 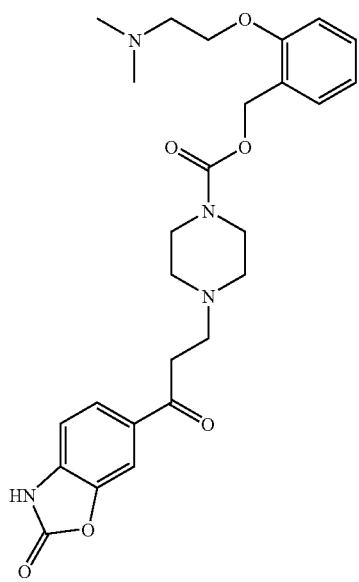 [SMILES: CN(C)CCOc1ccccc1COC(=O)N1CCN(CCC(=O)c2ccc3[nH]c(=O)oc3c2)CC1]<br>2-(2-Dimethylaminoethoxy)benzyl 4-[3-oxo-3-(2-oxo-2,3-dihydrobenzoxazol-6-yl)propyl]-piperazine-1-carboxylate | 498 | 2.80 |
| "B18" | 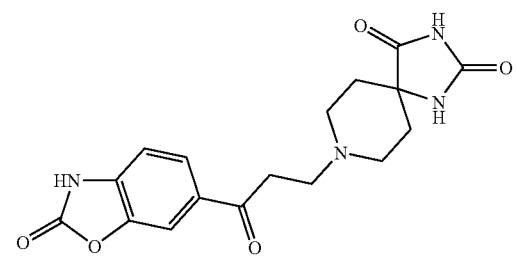 [SMILES: O=C1NC(=O)C2(CCN(CCC(=O)c3ccc4[nH]c(=O)oc4c3)CC2)N1]<br>8-[3-Oxo-3-(2-oxo-2,3-dihydrobenzoxazol-6-yl)-propyl]-1,3,8-triazaspiro[4.5]decane-2,4-dione | 359 | 3.63 |

-continued
| Compound No. | Name and/or structure | ESI [M + H]+ | HPLC (RT in min) method |
|---|---|---|---|
| "B19" | 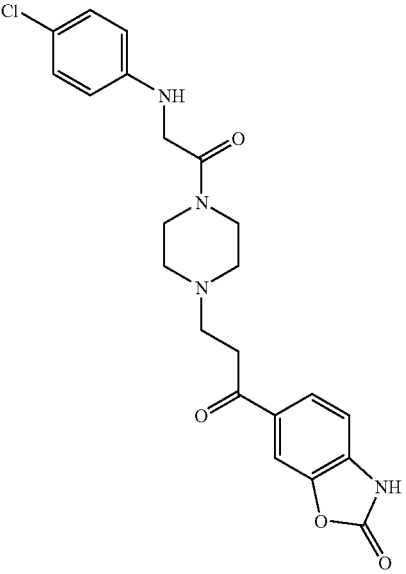 [SMILES: O=C(CCN1CCN(C(=O)CNc2ccc(Cl)cc2)CC1)c1ccc2[nH]c(=O)oc2c1]<br>6-(3-{4-[2-(4-Chlorophenylamino)acetyl]-piperazin-1-yl}propionyl)-3H-benzoxazol-2-one | 444 | 3.23 |
| "B20" | 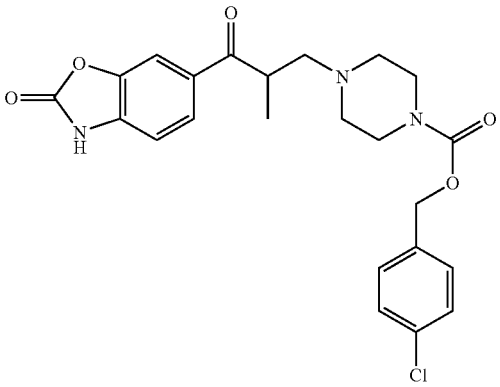 [SMILES: CC(CN1CCN(C(=O)OCc2ccc(Cl)cc2)CC1)C(=O)c1ccc2[nH]c(=O)oc2c1]<br>4-Chlorobenzyl 4-[2-methyl-3-oxo-3-(2-oxo-2,3-dihydrobenzoxazol-6-yl)propyl]piperazine-1-carboxylate | 459 | 3.39 |
| "B21" | 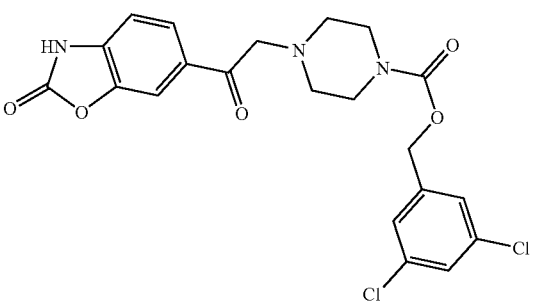 [SMILES: O=C(CN1CCN(C(=O)OCc2cc(Cl)cc(Cl)c2)CC1)c1ccc2[nH]c(=O)oc2c1]<br>3,5-Dichlorobenzyl 4-[2-oxo-2-(2-oxo-2,3-dihydrobenzoxazol-6-yl)ethyl]piperazine-1-carboxylate | 465 | 3.60 |

87 88
-continued
| Compound No. | Name and/or structure | ESI [M + H]+ | HPLC (RT in min) method |
|---|---|---|---|
| "B22" | 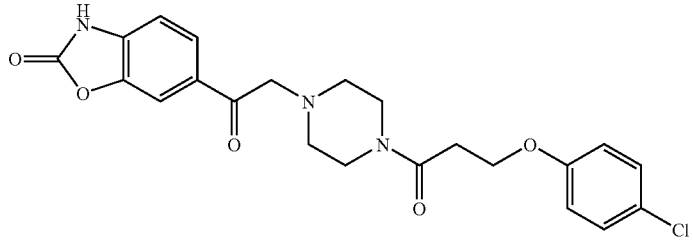 [SMILES: O=C(CN1CCN(C(=O)CCOc2ccc(Cl)cc2)CC1)c1ccc2[nH]c(=O)oc2c1]<br>6-(2-{4-[3-(4-Chlorophenoxy)propionyl]piperazin-1-yl}acetyl)-3H-benzoxazol-2-one | 445 | 3.20 |
| "B23" | 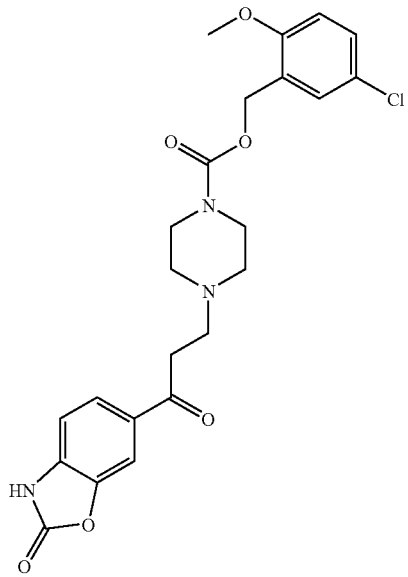 [SMILES: COc1ccc(Cl)cc1COC(=O)N1CCN(CCC(=O)c2ccc3[nH]c(=O)oc3c2)CC1]<br>5-Chloro-2-methoxybenzyl 4-[3-oxo-3-(2-oxo-2,3-dihydrobenzoxazol-6-yl)propyl]piperazine-1-carboxylate | 475 | 3.41 |

| Compound No. | Name and/or structure | ESI [M + H]+ | HPLC (RT in min) method |
|---|---|---|---|
| "B24" | 4'-Trifluoromethylbiphenyl-2-ylmethyl 4-[3-oxo-3-(2-oxo-2,3-dihydrobenzoxazol-6-yl)propyl]-piperazine-1-carboxylate | 555 | 4.24 |
| "B25" | 6-{3-[4-(4'-Methylbiphenyl-3-carbonyl)piperazin-1-yl]propionyl}-3H-benzoxazol-2-one | 471 | 3.49 |

| Compound No. | Name and/or structure | ESI [M + H]⁺ | HPLC (RT in min) method |
|---|---|---|---|
| "B26" | 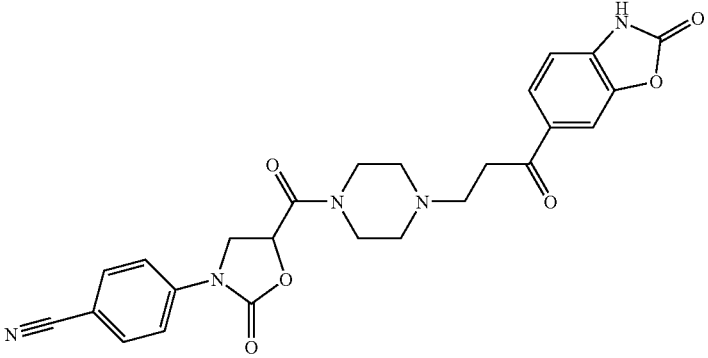 [SMILES: N#Cc1ccc(N2CC(C(=O)N3CCN(CCC(=O)c4ccc5[nH]c(=O)oc5c4)CC3)OC2=O)cc1]<br>4-(2-Oxo-5-{4-[3-oxo-3-(2-oxo-2,3-dihydro-benzoxazol-6-yl)propyl]piperazine-1-carbonyl}-oxazolidin-3-yl)benzonitrile | 490 | 2.77 |
| "B27" | 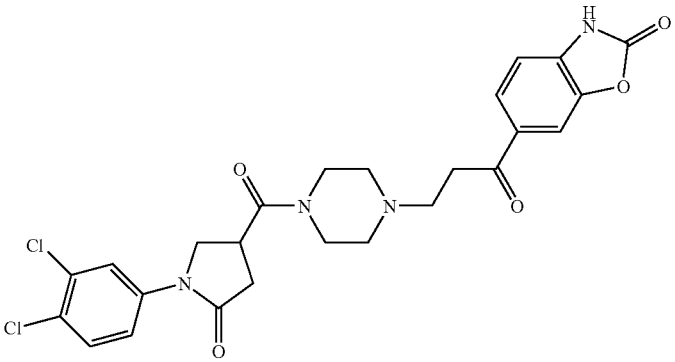 [SMILES: O=C(CCN1CCN(C(=O)C2CC(=O)N(c3ccc(Cl)c(Cl)c3)C2)CC1)c1ccc2[nH]c(=O)oc2c1]<br>6-(3-{4-[2-(3,4-Dichlorophenyl)thiazolidine-4-carbonyl]piperazin-1-yl}propionyl)-3H-benzoxazol-2-one | 536 | 3.41 |
| "B28" | 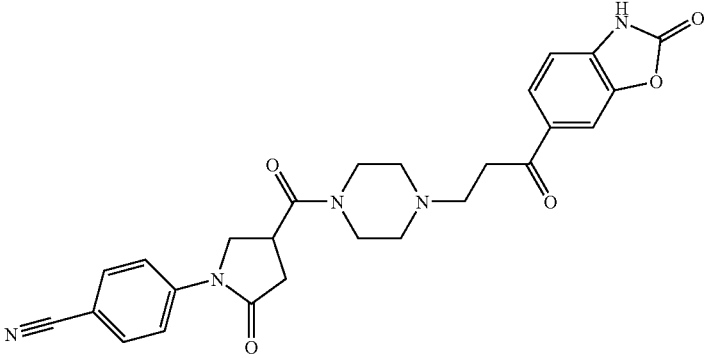 [SMILES: N#Cc1ccc(N2CC(C(=O)N3CCN(CCC(=O)c4ccc5[nH]c(=O)oc5c4)CC3)CC2=O)cc1]<br>4-(2-Oxo-4-{4-[3-oxo-3-(2-oxo-2,3-dihydro-benzoxazol-6-yl)propyl]piperazine-1-carbonyl}-pyrrolidin-1-yl)benzonitrile | 489 | 2.77 |

| Compound No. | Name and/or structure | ESI [M + H]+ | HPLC (RT in min) method |
|---|---|---|---|
| "B29" | 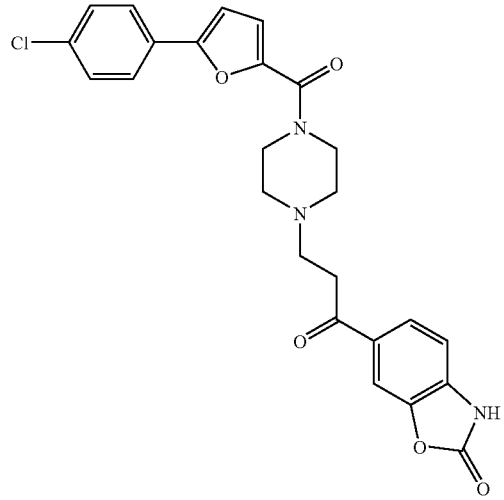 [SMILES: O=C(CCN1CCN(C(=O)c2ccc(-c3ccc(Cl)cc3)o2)CC1)c1ccc2[nH]c(=O)oc2c1]<br>6-(3-{4-[5-(4-Chlorophenyl)furan-2-carbonyl]-piperazin-1-yl}propionyl)-3H-benzoxazol-2-one | 481 | 3.52 |
| "B30" | 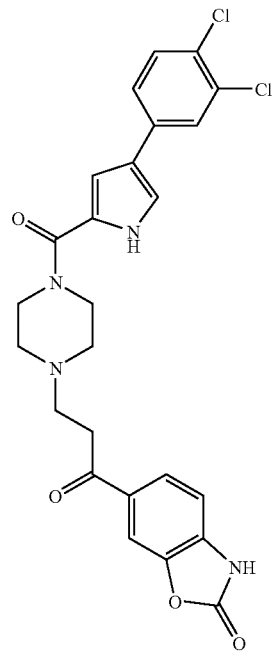 [SMILES: O=C(CCN1CCN(C(=O)c2cc(-c3ccc(Cl)c(Cl)c3)c[nH]2)CC1)c1ccc2[nH]c(=O)oc2c1]<br>6-(3-{4-[4-(3,4-Dichlorophenyl)-1H-pyrrole-2-carbonyl]piperazin-1-yl}propionyl)-3H-benzoxazol-2-one | 514 | 3.76 |
| "B31" | 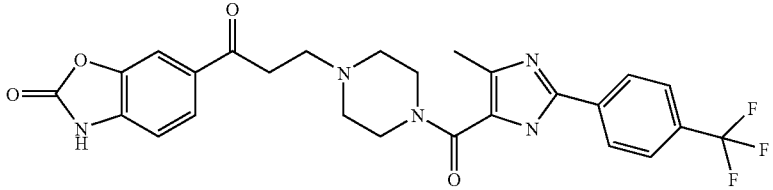<br>6-(3-{4-[4-Methyl-2-(4-trifluoromethylphenyl)-thiazole-5-carbonyl]piperazin-1-yl}propionyl)-3H-benzoxazol-2-one | 546 | 3.71 |

-continued
| Compound No. | Name and/or structure | ESI [M + H]+ | HPLC (RT in min) method |
|---|---|---|---|
| "B32" | 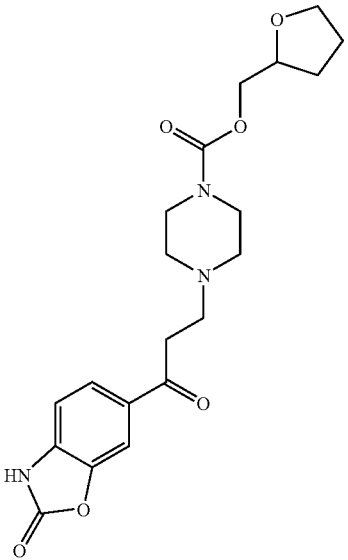 [SMILES: O=C(CCN1CCN(C(=O)OCC2CCCO2)CC1)c1ccc2[nH]c(=O)oc2c1]<br>Tetrahydrofuran-2-ylmethyl 4-[3-oxo-3-(2-oxo-2,3-dihydrobenzoxazol-6-yl)propyl]piperazine-1-carboxylate | 404 | 1.52 |
| "B33" | 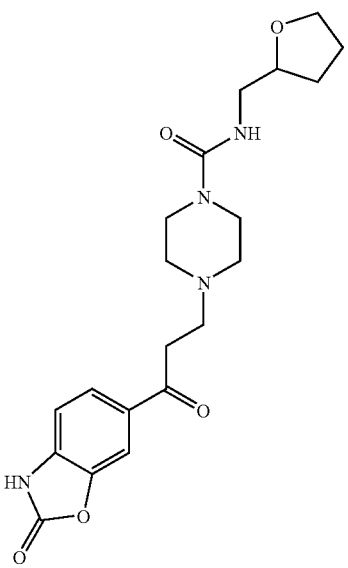 [SMILES: O=C(CCN1CCN(C(=O)NCC2CCCO2)CC1)c1ccc2[nH]c(=O)oc2c1]<br>N-(Tetrahydrofuran-2-ylmethyl)-4-[3-oxo-3-(2-oxo-2,3-dihydrobenzoxazol-6-yl)propyl]-piperazine-1-carboxamide | 403 | 1.28 |

-continued
| Compound No. | Name and/or structure | ESI [M + H]+ | HPLC (RT in min) method |
|---|---|---|---|
| "B34" | 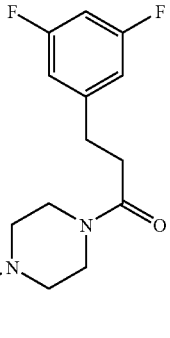<br>6-(3-{4-[3-(3,5-Difluorophenyl)propionyl]-piperazin-1-yl}propionyl)-3H-benzoxazol-2-one | 444 | 3.20 |
| "B35" | 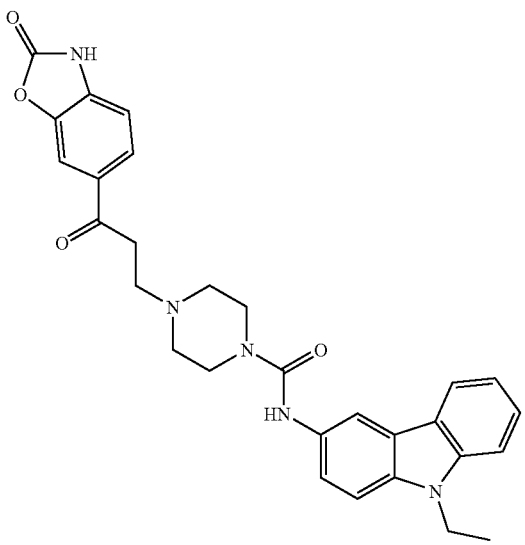 [SMILES: CCn1c2ccccc2c2cc(NC(=O)N3CCN(CCC(=O)c4ccc5[nH]c(=O)oc5c4)CC3)ccc21]<br>N-(9-Ethyl-9H-carbazol-3-yl)-4-[3-oxo-3-(2-oxo-2,3-dihydrobenzoxazol-6-yl)propyl]piperazine-1-carboxamide | 513 | 3.57 |
| "B36" | 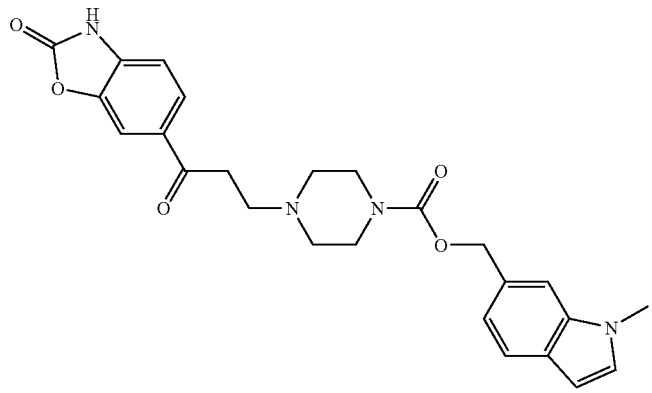 [SMILES: Cn1ccc2ccc(COC(=O)N3CCN(CCC(=O)c4ccc5[nH]c(=O)oc5c4)CC3)cc21]<br>1-Methyl-1H-indol-6-ylmethyl 4-[3-oxo-3-(2-oxo-2,3-dihydrobenzoxazol-6-yl)propyl]piperazine-1-carboxylate | 464 | 3.33 |

-continued

| Compound No. | Name and/or structure | ESI [M + H]+ | HPLC (RT in min) method |
|---|---|---|---|
| "B37" | 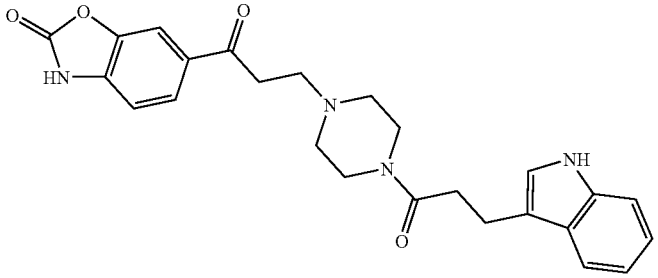 [SMILES: O=C(CCN1CCN(C(=O)CCc2c[nH]c3ccccc23)CC1)c1ccc2[nH]c(=O)oc2c1]<br>6-{3-[4-(3-1H-Indol-3-ylpropionyl)piperazin-1-yl]-propionyl}-3H-benzoxazol-2-one | 448 | 2.83 |
| "B38" | 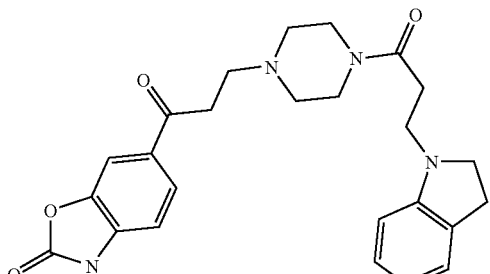<br>6-{3-[4-(3-Indol-1-ylpropionyl)piperazin-1-yl]-propionyl}-3H-benzoxazol-2-one | 448 | 3.12 |
| "B39" | 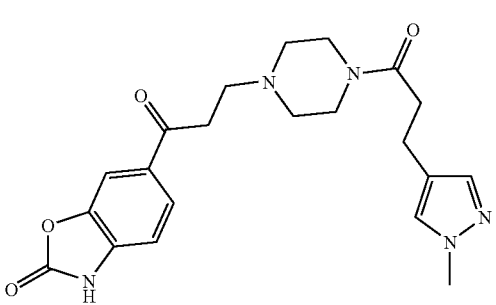 [SMILES: Cn1cc(CCC(=O)N2CCN(CCC(=O)c3ccc4[nH]c(=O)oc4c3)CC2)cn1]<br>6-(3-{4-[3-(1-Methyl-1H-pyrazol-4-yl)propionyl]-piperazin-1-yl}propionyl)-3H-benzoxazol-2-one | 412 | 2.43 |
| "B40" | 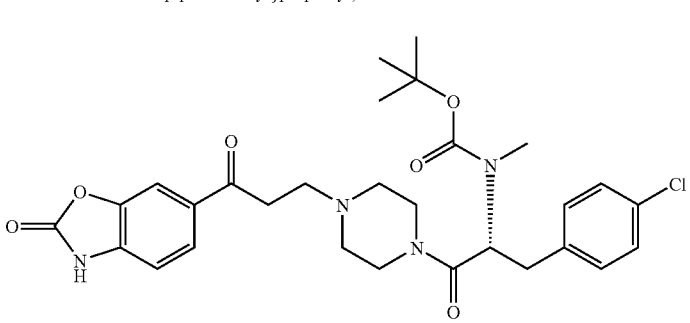<br>tert-Butyl((R)-1-(4-chlorobenzyl)-2-oxo-2-{4-[3-oxo-3-(2-oxo-2,3-dihydrobenzoxazol-6-yl)propyl]-piperazin-1-yl}ethyl)methylcarbamate | 572 | 23.89 |

-continued

| Compound No. | Name and/or structure | ESI [M + H]+ | HPLC (RT in min) method |
|---|---|---|---|
| "B41" | 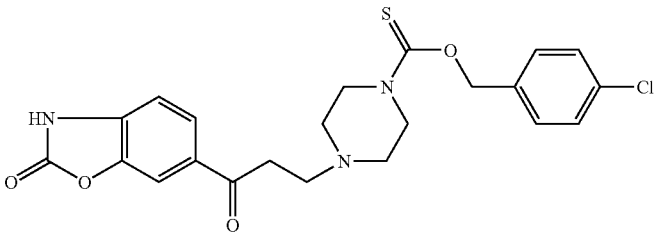 [SMILES: O=C(CCN1CCN(C(=S)OCc2ccc(Cl)cc2)CC1)c1ccc2[nH]c(=O)oc2c1]<br>O-(4-Chlorobenzyl)4-[3-oxo-3-(2-oxo-2,3-dihydrobenzoxazol-6-yl)propyl]piperazine-1-carbothiolate | 461 | 3.76 |
| "B42" | 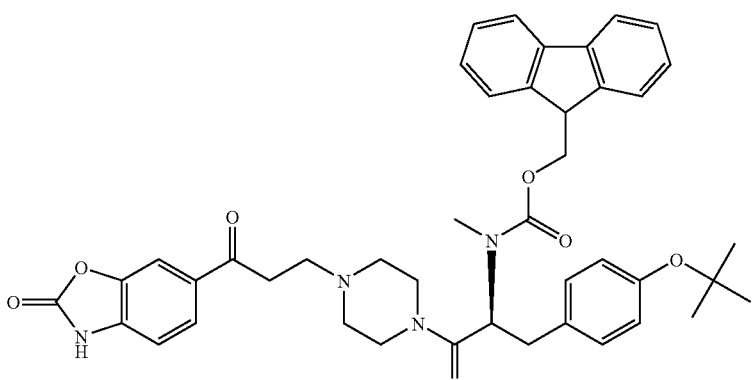<br>9H-Fluoren-9-ylmethyl((S)-1-(4-tert-butoxy-benzyl)-2-oxo-2-{4-[3-oxo-3-(2-oxo-2,3-di hydro-benzoxazol-6-yl)propyl]piperazin-1-yl}ethyl)-methylcarbamate | 732 | 4.03 |
| "B43" | 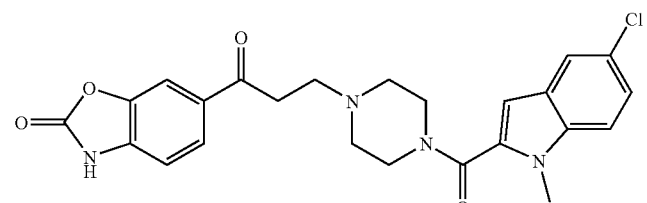<br>6-{3-[4-(5-Chloro-1-methyl-1H-indole-2-carbonyl)piperazin-1-yl]propionyl}-3H-benzoxazol-2-one | 468 | 3.49 |
| "B44" | 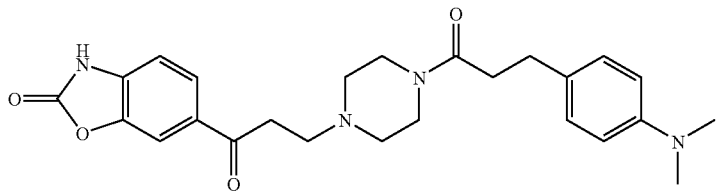 [SMILES: CN(C)c1ccc(CCC(=O)N2CCN(CCC(=O)c3ccc4[nH]c(=O)oc4c3)CC2)cc1]<br>6-(3-{4-[3-(4-Dimethylaminophenyl)propionyl]-piperazin-1-yl}propionyl)-3H-benzoxazol-2-one | 452 | 1.07 |

| Compound No. | Name and/or structure | ESI [M + H]+ | HPLC (RT in min) method |
|---|---|---|---|
| "B45" | 2-Methyl-5-phenyl-2H-pyrazol-3-ylmethyl 4-[3-oxo-3-(2-oxo-2,3-dihydrobenzoxazol-6-yl)propyl]-piperazine-1-carboxylate | 491 | 3.17 |
| "B46" | 6-(3-{4-[3-(4-Chlorobenzyl)-1,2,4-oxadiazol-5-yl]-piperidin-1-yl}propionyl)-3H-benzoxazol-2-one | 468 | 3.55 |
EXAMPLE 7
Synthesis of 3,5-dichlorobenzyl 4-[2-(3H-benzotriazole-5-sulfinyl)ethyl]-piperazine-1-carboxylate ("B48"); hydrochloride 8
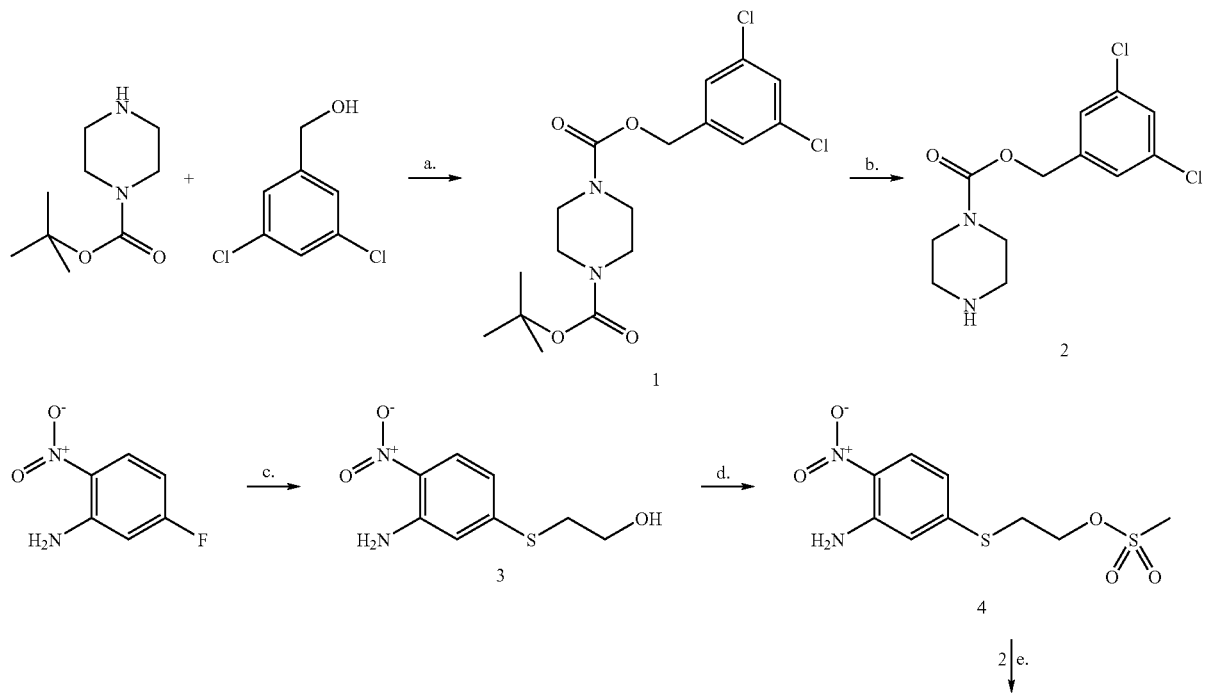

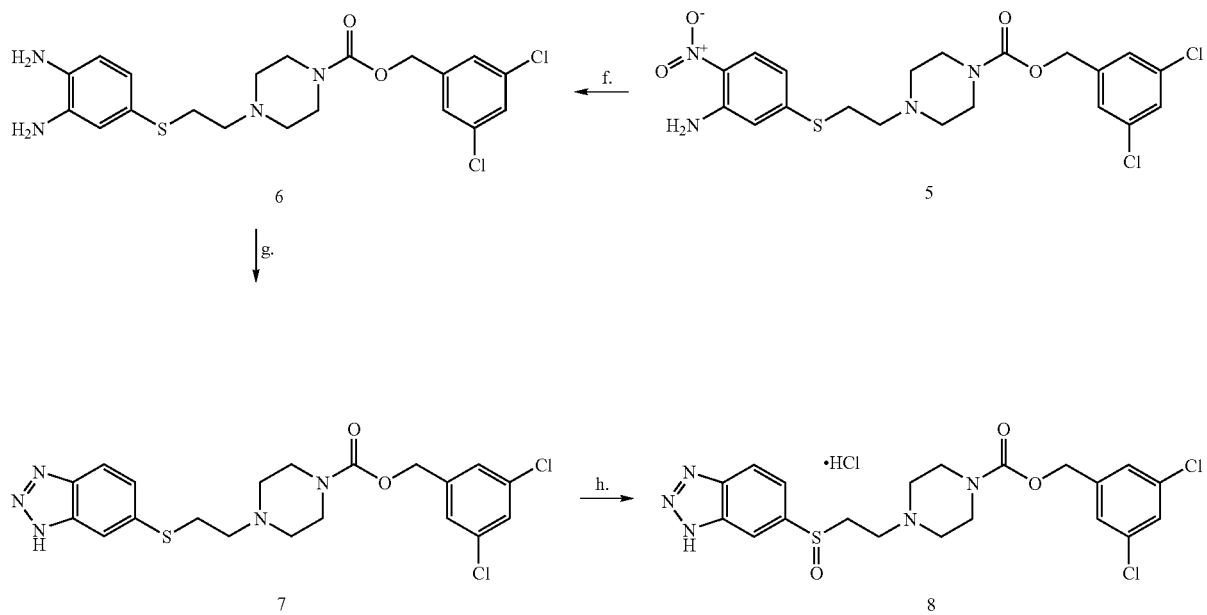

a. 1,1'-Carbonyldiimidazole (5.10 g, 31.4 mmol) and (3,5-dichlorophenyl)-methanol (5.55 g, 31.3 mmol) is dissolved in DMF (70 ml) and stirred at RT for 2 h. tert-Butyl piperazine-1-carboxylate (5.30 g, 28.4 mmol) is subsequently added, and stirring is continued at RT for 18 h. The solvent is removed in a rotary evaporator, diluted with DCM (100 ml) and washed 2× with water. The organic phase is separated off, dried over magnesium sulfate, filtered off and evaporated to dryness. The colourless product 1 obtained (10.60 g, 27.2 mmol, 95.6%) is reacted without further purification.

b. Compound 1 (10.60 g, 27.2 mmol) is taken up in 6N HCl in 2-propanol (100 ml) and stirred at RT for 2 h. The reaction mixture is evaporated to dryness, giving a colourless solid (10.0 g, 30.7 mmol, 112%), which proved to be compound 2.

c. 5-Fluoro-2-nitroaniline (5.0 g, 32.0 mmol) and 2-mercaptoethanol (2.23 ml, 32.0 mmol) is dissolved in 50 ml of acetonitrile and warmed to 80° C. After 10 minutes, triethylamine (4.44 ml, 32.0 mmol) is carefully added. The mixture is stirred at 80° C. for 48 h, with 2-mercaptoethanol being added twice (in total 4.46 ml, 64.0 mmol). The reaction mixture is evaporated, diluted with 200 ml of ethyl acetate and washed 2× with 100 ml of water. The organic phase is separated off, dried over magnesium sulfate, filtered off and evaporated to dryness. The crude product is purified by chromatography on 150 g of silica gel (eluent petroleum ether/ethyl acetate 1:1). Evaporation of the corresponding fractions gives an oil, which can be crystallised from etanol by addition of ether, giving 6.9 g (32.2 mmol 100.6%) of colourless crystals 3.

d. 3 (2.8 g, 13.07 mmol) and trieethylamine (1.80 ml, 13.07 mmol) is dissolved in 40 ml of DCM. Methanesulfonyl chloride (1.01 ml, 13.07 mmol) was then added dropwise. The reaction mixture is stirred for 2 h and subsequently evaporated. The crude product 4 (3.8 g, 13.0 mmol, 99.5%) is not purified further.

e. Compounds 2 (4.23 g, 13.0 mmol), 4 (3.80 g, 13.0 mmol) and triethylamine (3.60 ml, 26.0 mmol) are dissolved in 40 ml of DMF and stirred at 60° C. for 72 h. The reaction mixture is evaporated, diluted with 200 ml of ethyl acetate and washed 2× with 100 ml of water. The organic phase is separated off, dried over magnesium sulfate, filtered off and evaporated to dryness. The crude product is purified by chromatography on 100 g of silica gel (eluent petroleum ether/ethyl acetate 1:1). Evaporation of the corresponding fractions gives 0.73 g (1.50 mmol, 11.6%) of 5 as yellowish solid substance.

f. 5 (0.73 g, 1.50 mmol) are dissolved in 10 ml of tetrahydrofuran, 0.60 g of Pd/C (5%) is added, and the mixture is hydrogenated to completeness at RT. The duration of the experiment is 30 h. The catalyst is filtered off. Evaporation of the solution gives 0.66 g (1.45 mmol, 96.4%) of 6 as solid substance.

g. 0.66 g (1.45 mmol) of 6 are dissolved in 20 ml of acetic acid, and sodium nitrite (0.10 g, 1.45 mmol) is added. The mixture is stirred at RT for 1 h, then diluted with water and extracted with 100 ml of ethyl acetate. The organic phase is dried using magnesium sulfate and evaporated, giving 0.82 g (content 82%, 1.44 mmol, 99.3%) of 7 as colourless solid substance.

h. 0.82 g (1.44 mmol) of 7 are dissolved in 20 ml of acetic acid, and hydrogen peroxide (30%) (0.33 ml, 2.90 mmol) is added. The mixture is stirred at RT for 24 h, then diluted with water and neutralised using saturated, aqueous NaHCO3 solution. The mixture is then extracted with 100 ml of ethyl acetate. The organic phase is dried using magnesium sulfate and evaporated. The crude product is purified by chromatography on 100 g of silica gel (eluent ethyl acetate/methanol 4:1). After evaporation of the corresponding fractions, the residue is dissolved in 10 ml of methanol, and 0.25 ml (1.5 mmol) of 6N HCl in isopropanol is added. Evaporation gives 0.2 g (0.39 mmol, 27%) of 8 as amorphous solid substance.

The following compounds can be prepared using methods known to the person skilled in the art. They are preferably prepared by the synthetic methods from Example 7:

"B47" 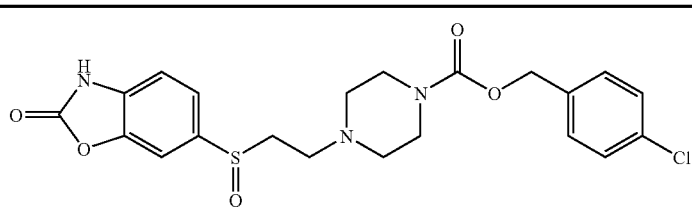 465 2.64
4-Chlorobenzyl 4-[2-(2-oxo-2,3-dihydrobenz-
oxazole-6-sulfinyl)ethyl]piperazine-1-carboxylate
"B48" 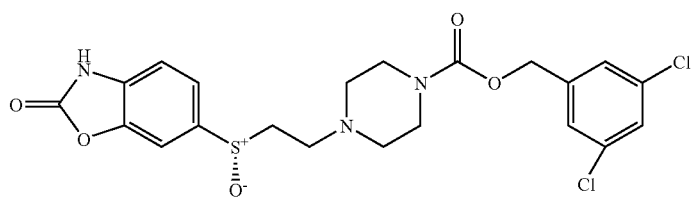 [SMILES: O=C(OCc1cc(Cl)cc(Cl)c1)N1CCN(CC[S@+]([O-])c2ccc3[nH]c(=O)oc3c2)CC1] 499 3.01
"B49" 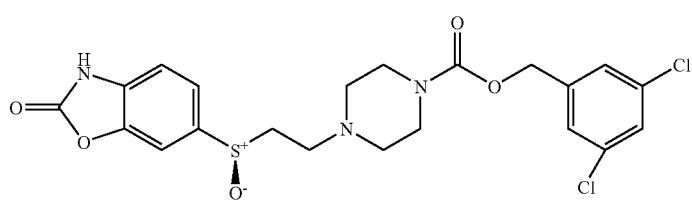 [SMILES: O=C(OCc1cc(Cl)cc(Cl)c1)N1CCN(CC[S@@+]([O-])c2ccc3[nH]c(=O)oc3c2)CC1] 499 3.01
"B50" 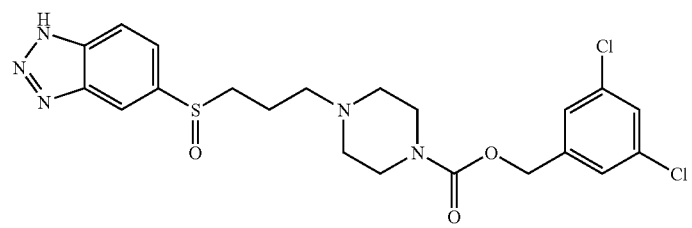 [SMILES: O=C(OCc1cc(Cl)cc(Cl)c1)N1CCN(CCCS(=O)c2ccc3[nH]nnc3c2)CC1] 497 2.72
3,5-Dichlorobenzyl 4-[3-(1H-benzotriazole-5-
sulfinyl)propyl]piperazine-1-carboxylate
"B51" 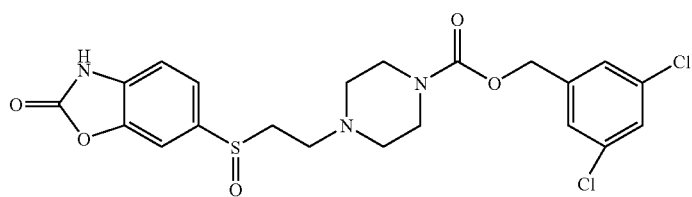 499 3.01
3,5-Dichlorobenzyl 4-[2-(2-oxo-2,3-dihydrobenz-
oxazole-6-sulfinyl)ethyl]piperazine-1-carboxylate
"B52" 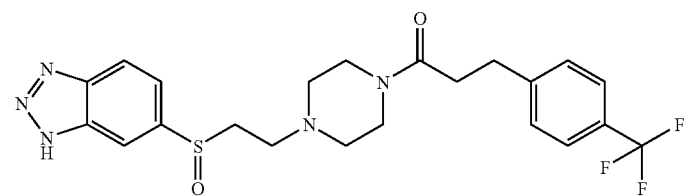 [SMILES: O=C(CCc1ccc(C(F)(F)F)cc1)N1CCN(CCS(=O)c2ccc3nn[nH]c3c2)CC1] 481 2.64
1-{4-[2-(3H-Benzotriazole-5-sulfinyl)ethyl]-
piperazin-1-yl}-3-(4-trifluoromethylphenyl)-
propan-1-one

"B53"

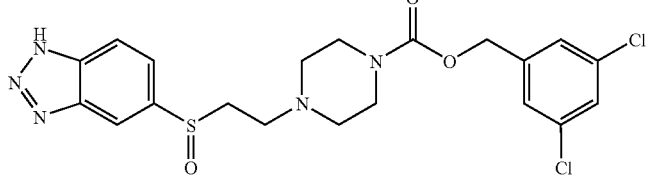

483    2.91

3,5-Dichlorobenzyl 4-[2-(1H-benzotriazole-5-sulfinyl)ethyl]piperazine-1-carboxylate

"B54"

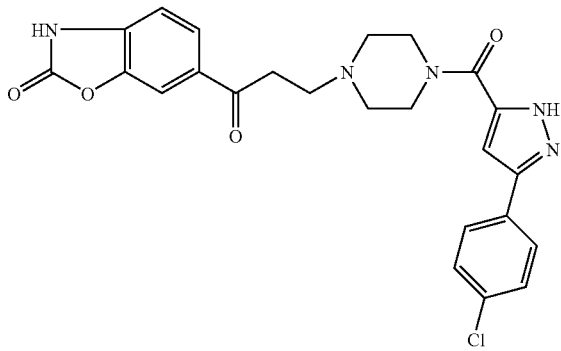 [SMILES: O=C(CCN1CCN(C(=O)c2cc(-c3ccc(Cl)cc3)n[nH]2)CC1)c1ccc2[nH]c(=O)oc2c1]

481

6-(3-{4-[5-(4-Chlorophenyl)-2H-pyrazole-3-carbonyl]piperazin-1-yl}propionyl)-3H-benzoxazol-2-one

EXAMPLE A

Autotaxin Test

Test Description

The autotaxin activity is measured indirectly using Amplex Red reagent. Amplex Red is measured here as fluorogenic indicator for the $H_2O_2$ formed. In detail, autotaxin converts the substrate lysophosphatidylcholine (LPC) into phosphocholine and lysophosphatidylic acid (LPA). After this reaction, the phosphocholine is reacted with alkaline phosphatase to give inorganic phosphate and choline. In the next step, choline is oxidised by choline oxidase to give betaine, with formation of $H_2O_2$. $H_2O_2$ reacts with Amplex Red reagent in the presence of peroxidase (horseradish peroxidase) in a 1:1 stoichiometry and forms the highly fluorescent resorufin. The fluorescence is measured in a reaction-dependent kinetic mode in order that fluorescent signals from possible other fluorescent substances which are not involved in the reaction can be corrected out.

Test Procedure 1.5 μl of a standard solution or of the test substances (substances with the name A(n)) in individual concentrations dissolved in 20 mM Hepes pH 7.2 with a maximum of 7.7% of DMSO are pre-incubated together with 10 μl (16 ng) of highly purified recombinant autotaxin in a black microtitre plate provided with 384 wells at 22° C. for 30 min. The reaction is then initiated by addition of 5 μl of L-a-lysophosphatidylcholine (LPC), where the final concentration of LPC is 75 μM. The mixture is incubated at 37° C. for 90 min. After the incubation, Amplex Red reagent, peroxidase (horseradish peroxidase) and choline oxidase is added, and the fluorescence is immediately measured at 612 nm with excitation of 485 nm in a "Tecan Ultra multimode" reader. The activity of autotaxin is calculated indirectly via detection of the $H_2O_2$ formed.

Material:

Microtitre plate: PS microplate, 384 wells, small volume, black Corning, Cat#3677

Protein: recombinant autotaxin (Baculovirale Hi5 Expression)

Substrate: L-a-lysophosphatidylcholine (chicken egg)); Avanti Polar Lipids #830071P Standard: C14 LPA, Avanti Polar Lipids, Cat#857120P Detection reagent: Amplex Red reagent; Invitrogen #A12222; dissolved in 1.923 ml of DMSO peroxidase type VI-A (horseradish) from Sigma # P6782; dissolved in 7.45 ml of test buffer, choline oxidase; Sigma # C5896; dissolved in 2.47 ml of test buffer Detection reagent mix: 1:100 dilution of Amplex Red reagent in test buffer Test buffer: 200 mM Tris HCl, Merck, Cat #1.08219, pH 7.9, 0.1% of BSA, lipid-free, Roche Cat#775835

The following examples relate to medicaments:

EXAMPLE B

Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

EXAMPLE C

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

EXAMPLE D

Solution

A solution is prepared from 1 g of an active ingredient of the formula I, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE E

Ointment 500 mg of an active ingredient of the formula I are mixed with 99.5 g of Vaseline under aseptic conditions.

EXAMPLE F

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE G

Dragees

Tablets are pressed analogously to Example E and subsequently coated in a conventional manner with a coating of sucrose, potato starch, talc, tragacanth and dye.

EXAMPLE H

Capsules 2 kg of active ingredient of the formula I are introduced into hard gelatine capsules in a conventional manner in such a way that each capsule contains 20 mg of the active ingredient.

EXAMPLE I

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:
1. A compound of formula I

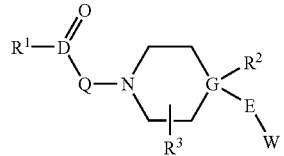

in which
$R^1$ denotes

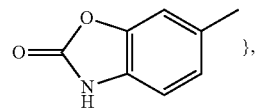

which is optionally mono- or disubstituted by A, Hal, $NR_2$, $(CR_2)_nCN$ and/or $OR^5$,
D denotes C or S,
G denotes N,
$R^2$ is absent,
Q denotes unbranched or branched alkylene having 1, 2, 3 or 4 C atoms, in which 1-5 H atoms may be replaced by A, $(CR_2)_n[X(CR_2)_n]_p$—Y, F and/or Cl,
$R^3$ denotes H, A, Ar, OR, SR, $NR_2$, Hal, $NO_2$, CN or $(CR_2)_n[X(CR_2)_n]_p$—Y,
X denotes O, NR or $CR_2$,
Y denotes OR or $NR_2$,
$R^5$ denotes H or unbranched or branched alkyl having 1, 2, 3, 4, 5 or 6 C atoms, in which 1-7 H atoms may be replaced by F and/or Cl,
E denotes $COO(CR_2)_n$, $COO(CRR^4)$, $CO(CR_2)_mO$, $CONH(CR_2)_n$, $C(=S)NH(CR_2)_n$, $S(O)_qNH(CR_2)_n$, $S(O)_q(CR_2)_n$, $COCH_2CH_2$, $CO(CR_2)_mO(CR_2)_n$, $CO(CR_2)_mNH(CR_2)_n$, $CO(CH_2)_nCO$, $COCHR^6CHR^7$, $C(=S)O(CR_2)_n$, $CO(CRR^4)(CR_2)_n$, $COO(CRR^4)$, $(CRR^4)(CR_2)_n$, $S(O)_qCR=CR$, $COCR=CR$, $CONH(CR_2)_mCRR^4$ or $(CR_2)_mCONR$,
$R^4$ denotes $COOR^5$, $Ar^1$, $NRCOOR^8$, $(CR_2)_nNR_2$ or NRCOOA,
$R^6,R^7$ together denote $(CH_2)_{1-4}$,
$R^8$ denotes phenyl, naphthyl or fluorenyl,
R denotes H or unbranched or branched alkyl having 1, 2, 3, 4, 5 or 6 C atoms,
W denotes Ar or Het,
Ar denotes phenyl, indanyl, naphthyl or biphenyl, each of which is unsubstituted or mono-, di-, tri-, tetra- or pentasubstituted by Hal, A, $(CR_2)_nOR$, $O(CR_2)_n$, $Ar^1$, $(CR_2)_nNR_2$, SR, $NO_2$, CN, COOR, $CONR_2$, NRCOA, $NRSO_2A$, $SO_2NR_2$, $S(O)_qA$, CO-Het, $(CR_2)_nHet$, $O(CR_2)_nNR_2$, $O(CR_2)_nHet$, NHCOOA, $NHCONR_2$, $NHCOO(CR_2)_nNR_2$, $NHCOO(CR_2)_nHet$, $CR^5=CR^5Ar^1$, $SO_2Het$, $NHCONH(CR_2)_nNR_2$, $NHCONH(CR_2)_nHet$, $OCONH(CR_2)_nNR_2$, $OCONH(CR_2)_nHet$, $CONR(CR_2)_nNR_2$, $CONR(CR_2)_nHet$ and/or COA,
Het denotes a mono-, bi- or tricyclic saturated, unsaturated or aromatic heterocycle having 1 to 4 N, O and/or S atoms, which may be unsubstituted or mono-, di- or trisubstituted by Hal, A, $(CR_2)_nAr^1$, $O(CR_2)_nAr^1$, $(CR_2)_nOR$, $(CR_2)_nNR_2$, SR, $NO_2$, CN, COOR, $CONR_2$, NRCOA, NRSO₂A, SO₂NR₂, S(O)$_q$A, CO-Het¹, (CR₂)$_n$Het¹, O(CR₂)$_n$NR₂, O(CR₂)$_n$Het¹, NHCOOA, NHCONR₂, NHCOO(CR₂)$_n$NR₂, NHCOO(CR₂)$_n$-Het¹, NHCONH(CR₂)$_n$NR₂, NHCONH(CR₂)$_n$Het¹, OCONH(CR₂)$_n$NR₂, OCONH(CR₂)$_n$Het¹, CO-Het¹, CHO, COA, =S, =NH, =NA and/or =O (carbonyl oxygen), Het¹ denotes a monocyclic saturated heterocycle having 1 to 2 N and/or O atoms, which may be mono- or disubstituted by A, OA, OH, Hal and/or =O (carbonyl oxygen), Ar¹ denotes phenyl which is unsubstituted or mono-, di-, tri-, tetra- or pentasubstituted by Hal, CN, A and/or (CR₂)$_n$OR, A denotes unbranched or branched alkyl having 1-10 C atoms, in which 1-7 H atoms may be replaced by OR, CN, NR₂, F and/or Cl and/or in which one or two non-adjacent CH₂ groups may be replaced by O, NH, S, SO, SO₂ and/or by CH=CH groups, or cyclic alkyl having 3-7 C atoms, m denotes 1, 2, 3, 4, 5 or 6, n denotes 0, 1, 2, 3, 4, 5, 6, 7 or 8, p denotes 1, 2, 3, 4, 5 or 6, q denotes 0, 1 or 2, and Hal denotes F, Cl, Br or I, or a pharmaceutically acceptable tautomer, salt or stereoisomer thereof.

2. A compound according to claim 1 in which R¹ denotes

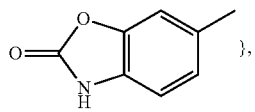

which is unsubstituted, or a pharmaceutically acceptable tautomer, salt or stereoisomer thereof.

3. A compound according to claim 1 in which R³ denotes H, or a pharmaceutically acceptable tautomer, salt or stereoisomer thereof.

4. A compound according to claim 1 in which

Q denotes unbranched or branched methylene, ethylene, propyl-ene or butylene, or a pharmaceutically acceptable tautomer, salt or stereoisomer thereof.

5. A compound according to claim 1 in which

R⁵ denotes H or unbranched or branched alkyl having 1, 2, 3 or 4 C atoms, in which 1-5 H atoms may be replaced by F, or a pharmaceutically acceptable tautomer, salt or stereoisomer thereof.

6. A compound according to claim 1 in which

R denotes H, methyl or ethyl, or a pharmaceutically acceptable tautomer, salt or stereoisomer thereof.

7. A compound according to claim 1 in which

R denotes H, or a pharmaceutically acceptable tautomer, salt or stereoisomer thereof.

8. A compound according to claim 1 in which

Ar denotes phenyl, indanyl, naphthyl or biphenyl, each of which is unsubstituted or mono-, di-, tri-, tetra- or pentasubstituted by Hal, A, (CR₂)$_n$OR, O(CR₂)$_n$Ar¹, (CR₂)$_n$NR₂, SR, NO₂, CN, COOR, CONR₂, NRCOA, NRSO₂A, SO₂NR₂, S(O)$_q$A, CO-Het, (CR₂)$_n$Het, O(CR₂)$_n$NR₂, CR⁵=CR⁵Ar¹ and/or SO₂Het, or a pharmaceutically acceptable tautomer, salt or stereoisomer thereof.

9. A compound according to claim 1 in which

Het denotes a mono- or bicyclic saturated, unsaturated or aromatic heterocycle having 1 to 3 N, O and/or S atoms, which is unsubstituted or mono- or disubstituted by Hal, A, (CR₂)$_n$Ar¹ and/or =O (carbonyl oxygen), or a pharmaceutically acceptable tautomer, salt or stereoisomer thereof.

10. A compound according to claim 1 in which

Het denotes piperidinyl, piperazinyl, pyrrolidinyl, morpholinyl, furanyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, indolyl, benzo-1,3-dioxolyl, indazolyl, 2,3-dihydrobenzo-1,4-dioxinyl, chromanyl, thiazolidinyl, isoindolyl, tetrahydrofuranyl, carbazolyl, benzo[b]thiophenyl or benzo-2,1,3-thiadiazolyl, each of which is unsubstituted or mono- or disubstituted by Hal, A, (CR₂)$_n$Ar¹ and/or =O (carbonyl oxygen), or a pharmaceutically acceptable tautomer, salt or stereoisomer thereof.

11. A compound according to claim 1 in which

A denotes unbranched or branched alkyl having 1-10 C atoms, in which 1-7 H atoms may be replaced by F and/or Cl, or a pharmaceutically acceptable tautomer, salt or stereoisomer thereof.

12. A compound according to claim 1 in which m denotes 1, 2, 3 or 4, n denotes 0, 1, 2, 3 or 4, P denotes 1, 2, 3 or 4, q denotes 0, 1 or 2, or a pharmaceutically acceptable tautomer, salt or stereoisomer thereof.

13. A compound according to claim 1 in which

Q denotes unbranched or branched methylene, ethylene, propylene or butylene,

R³ denotes H,

R⁵ denotes H or unbranched or branched alkyl having 1, 2, 3 or 4 C atoms, in which 1-5 H atoms may be replaced by F, E denotes COO(CR₂)$_n$, COO(CRR⁴), CO(CR₂)$_m$O, CONH(CR₂)$_n$, S(O)$_q$(CR₂)$_n$, COCH₂CH₂, CO(CR₂)$_m$O(CR₂)$_p$, CO(CR₂)$_m$NH(CR₂)$_p$, C(=S)O(CR₂)$_n$, CO(CRR⁴)(CR₂)$_n$, COO(CRR⁴), (CRR⁴)(CR₂)$_n$, S(O)$_q$CR=CR, COCR=CR, or (CR₂)$_m$CONR, R⁴ denotes COOR⁵, Ar¹, (CR₂)$_n$NR₂ or NRCOOA, R denotes H or unbranched or branched alkyl having 1, 2, 3, 4, 5 or 6 C atoms, W denotes Ar or Het, Ar denotes phenyl, indanyl, naphthyl or biphenyl, each of which is unsubstituted or mono-, di-, tri-, tetra- or pentasubstituted by Hal, A, (CR₂)$_n$OR, O(CR₂)$_n$Ar¹, (CR₂)$_n$NR₂, SR, NO₂, CN, COOR, CONR₂, NRCOA, NRSO₂A, SO₂NR₂, S(O)$_q$A, CO-Het, (CR₂)$_n$Het, O(CR₂)$_n$NR₂, CR⁵=CR⁵Ar¹ and/or SO₂Het, Het denotes a mono- or bicyclic saturated, unsaturated or aro-matic heterocycle having 1 to 3 N, O and/or S atoms, which is unsubstituted or mono- or disubstituted by Hal, A, (CR₂)$_n$Ar¹ and/or =O (carbonyl oxygen), Ar¹ denotes phenyl which is unsubstituted or mono-, di-, tri-, tetra- or pentasubstituted by Hal, CN, A and/or $(CR_2)_nOR$, A denotes unbranched or branched alkyl having 1-10 C atoms, in which 1-7 H atoms may be replaced by F and/or Cl, m denotes 1, 2, 3 or 4,
n denotes 0, 1, 2, 3 or 4,
p denotes 1, 2, 3 or 4,
q denotes 0, 1 or 2, and
Hal denotes F, Cl, Br or I,
or a pharmaceutically acceptable tautomer, salt or stereoisomer thereof.

14. A compound according to claim 1 in which $R^1$ denotes

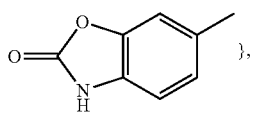, which is optionally mono- or disubstituted by A, Hal, $NR_2$, $(CR_2)_nCN$ and/or $OR^5$, Q denotes methylene, ethylene, propylene or butylene,
$R^3$ denotes H,
$R^5$ denotes H or unbranched or branched alkyl having 1, 2, 3 or 4 C atoms, in which 1-5 H atoms may be replaced by F, E denotes $COO(CR_2)_n$, $COO(CRR^4)$, $CO(CR_2)_mO$, $CONH(CR_2)_n$, $S(O)_q(CR_2)_n$, $COCH_2CH_2$, $CO(CR_2)_mO(CR_2)_p$, $CO(CR_2)_mNH(CR_2)_p$, $C(=S)O(CR_2)_n$, $CO(CRR^4)(CR_2)_n$, $COO(CRR^4)$, $(CRR^4)(CR_2)_n$, $S(O)_qCR=CR$, $COCR=CR$, or $(CR_2)_mCONR$, $R^4$ denotes $COOR^5$, $Ar^1$, $(CR_2)_nNR_2$ or $NRCOOA$,
R denotes H, methyl or ethyl,
W denotes Ar or Het, Ar denotes phenyl, indanyl, naphthyl or biphenyl, each of which is unsubstituted or mono-, di-, tri-, tetra- or pentasubstituted by Hal, A, $(CR_2)_nOR$, $O(CR_2)_nAr^1$, $(CR_2)_nNR_2$, SR, $NO_2$, CN, COOR, $CONR_2$, NRCOA, $NRSO_2A$, $SO_2NR_2$, $S(O)_qA$, CO-Het, $(CR_2)_n$Het, $O(CR_2)_nNR_2$, $CR^5=CR^5Ar^1$ and/or $SO_2$Het, Het denotes piperidinyl, piperazinyl, pyrrolidinyl, morpholinyl, furanyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, indolyl, benzo-1,3-dioxolyl, indazolyl, 2,3-dihydrobenzo-1,4-dioxinyl, chromanyl, thiazolidinyl, isoindolyl, tetrahydrofuranyl, carbazolyl, benzo[b]thiophenyl or benzo-2,1,3-thiadiazolyl, each of which is unsubstituted or mono- or disubstituted by Hal, A, $(CR_2)_nAr^1$ and/or =O (carbonyl oxygen), Ar¹ denotes phenyl which is unsubstituted or mono-, di-, tri-, tetra- or pentasubstituted by Hal, CN, A and/or $(CR_2)_nOR$, A denotes unbranched or branched alkyl having 1-10 C atoms, in which 1-7 H atoms may be replaced by F and/or Cl, m denotes 1, 2, 3 or 4,
n denotes 0, 1, 2, 3 or 4,
p denotes 1, 2, 3 or 4,
q denotes 0, 1 or 2, and
Hal denotes F, Cl, Br or I,
or a pharmaceutically acceptable tautomer, salt or stereoisomer thereof.

15. A compound, which is one of the following compounds

| Compound No. | Name and/or structure |
| --- | --- |
| "A1" | 4-Chlorobenzyl 4-[3-oxo-3-(2-oxo-2,3-dihydrobenzoxazol-6-yl)propyl]piperazine-1-carboxylate |
| "A2" | 6-(3-{4-[2-(4-Chlorophenoxy)acetyl]piperazin-1-yl}propionyl)-3H-benzoxazol-2-one |
| "A3" | 6-(3-{4-[2-(4-Chlorophenyl)ethylsulfonyl]piperazin-1-yl}-propionyl)-3H-benzoxazol-2-one |
| "A4" | N-(4-Trifluoromethoxybenzyl)-4-[3-oxo-3-(2-oxo-2,3-dihydro-benzoxazol-6-yl)propyl]piperazine-1-carboxamide |
| "A5" | 6-(3-{4-[3-(4-Trifluoromethylphenyl)propionyl]piperazin-1-yl}-propionyl)-3H-benzoxazol-2-one |
| "A6" | 4-Chlorobenzyl 4-[2-oxo-2-(2-oxo-2,3-dihydrobenzoxazol-6-yl)ethyl]piperazine-1-carboxylate |
| "A10" | 6-{3-[4-(2,3-Dihydrobenzo-1,4-dioxin-2-carbonyl)piperazin-1-yl]propionyl}-3H-benzoxazol-2-one |
| | 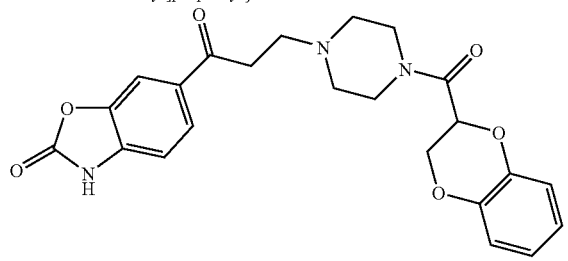 |
| "A11" | 6-(3-{4-[2-(4-Fluorophenyl)ethyl]piperazin-1-yl}propionyl)-3H-benzoxazol-2-one |

-continued

| Compound No. | Name and/or structure |
|---|---|
| "A12" | 6-{3-[4-(Pyridine-4-carbonyl)piperazin-1-yl]propionyl}-3H-benzoxazol-2-one 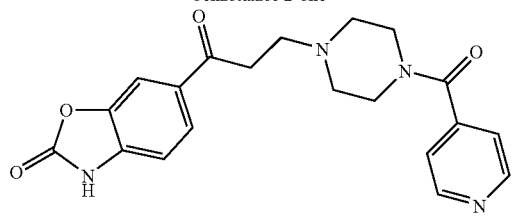 |
| "A13" | 6-(3-{4-[2-(2,3-Dimethoxyphenyl)acetyl]piperazin-1-yl}-propionyl)-3H-benzoxazol-2-one 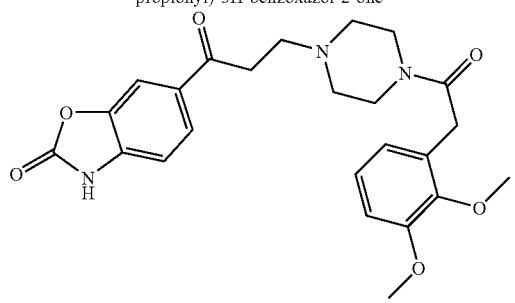 |
| "A19" | Benzyl 4-[3-oxo-3-(2-oxo-2,3-dihydrobenzoxazol-6-yl)-propyl]piperazine-1-carboxylate 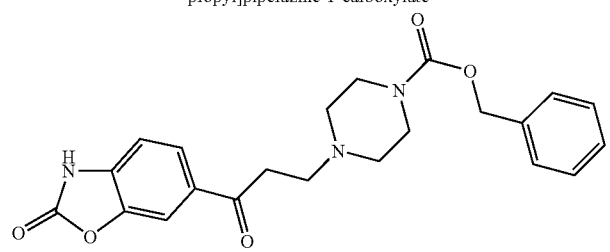 |
| "A20" | 3,4-Dimethoxybenzyl 4-[3-oxo-3-(2-oxo-2,3-dihydrobenzoxazol-6-yl)propyl]piperazine-1-carboxylate 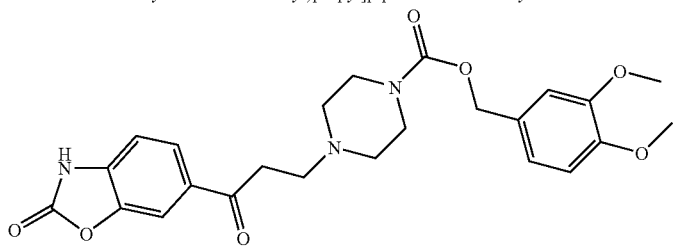 |
| "A21" | 2-Chlorobenzyl 4-[3-oxo-3-(2-oxo-2,3-dihydrobenzoxazol-6-yl)propyl]piperazine-1-carboxylate 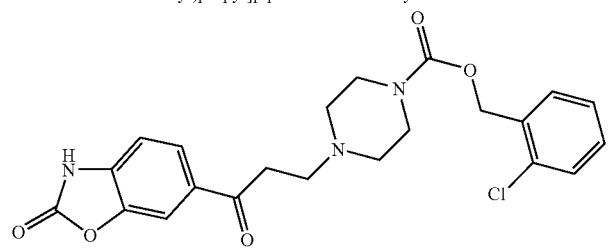 |

-continued

| Compound No. | Name and/or structure |
|---|---|
| "A22" | 2,4-Dichlorobenzyl 4-[3-oxo-3-(2-oxo-2,3-dihydrobenzoxazol-6-yl)propyl]piperazine-1-carboxylate 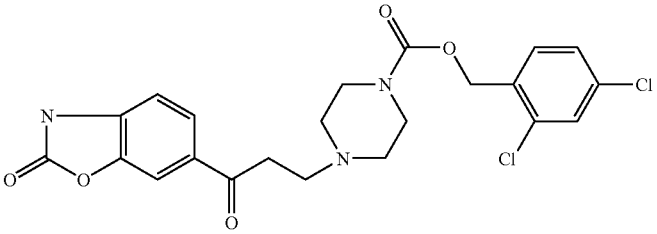 [SMILES: O=C(CCN1CCN(C(=O)OCc2ccc(Cl)cc2Cl)CC1)c1ccc2[nH]c(=O)oc2c1] |
| "A23" | tert-Butylbenzyl 4-[3-oxo-3-(2-oxo-2,3-dihydrobenzoxazol-6-yl)propyl]piperazine-1-carboxylate |
| "A24" | 4-Methylbenzyl 4-[3-oxo-3-(2-oxo-2,3-dihydrobenzoxazol-6-yl)propyl]piperazine-1-carboxylate |
| "A25" | 4-Ethylbenzyl 4-[3-oxo-3-(2-oxo-2,3-dihydrobenzoxazol-6-yl)propyl]piperazine-1-carboxylate |
| "A26" | 3,4-Dimethylbenzyl 4-[3-oxo-3-(2-oxo-2,3-dihydro-benzoxazol-6-yl)propyl]piperazine-1-carboxylate |
| "A27" | 4-Chloro-2-methylbenzyl 4-[3-oxo-3-(2-oxo-2,3-dihydro-benzoxazol-6-yl)propyl]piperazine-1-carboxylate |
| "A29" | Indan-1-yl 4-[3-oxo-3-(2-oxo-2,3-dihydrobenzoxazol-6-yl)-propyl]piperazine-1-carboxylate 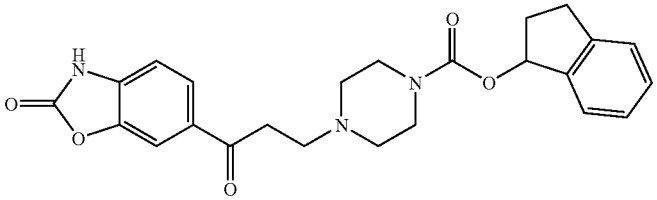 [SMILES: O=C(CCN1CCN(C(=O)OC2CCc3ccccc32)CC1)c1ccc2[nH]c(=O)oc2c1] |
| "A30" | 3-Benzyloxybenzyl 4-[3-oxo-3-(2-oxo-2,3-dihydro-benzoxazol-6-yl)propyl]piperazine-1-carboxylate 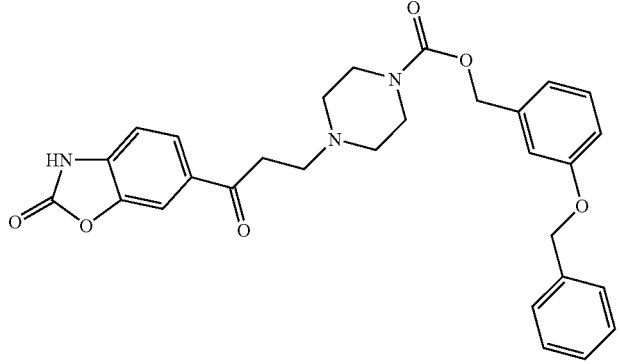 [SMILES: O=C(CCN1CCN(C(=O)OCc2cccc(OCc3ccccc3)c2)CC1)c1ccc2[nH]c(=O)oc2c1] |
| "A31" | Ethoxycarbonylphenylmethyl 4-[3-oxo-3-(2-oxo-2,3-dihydro-benzoxazol-6-yl)propyl]piperazine-1-carboxylate 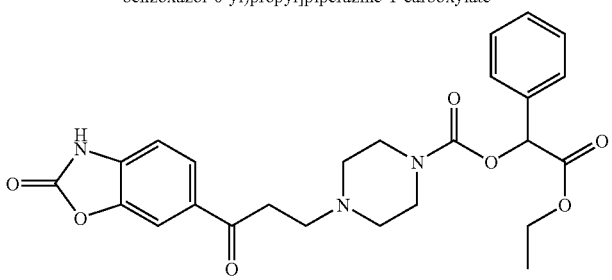 |

-continued

| Compound No. | Name and/or structure |
|---|---|
| "A32" | Benzohydryl 4-[3-oxo-3-(2-oxo-2,3-dihydrobenzoxazol-6-yl)-propyl]piperazine-1-carboxylate |
| "A33" | 3-Methoxybenzyl 4-[3-oxo-3-(2-oxo-2,3-dihydrobenzoxazol-6-yl)propyl]piperazine-1-carboxylate |
| "A34" | 2-Methoxybenzyl 4-[3-oxo-3-(2-oxo-2,3-dihydrobenzoxazol-6-yl)propyl]piperazine-1-carboxylate |
| "A35" | 1-(4-Fluorophenyl)ethyl 4-[3-oxo-3-(2-oxo-2,3-dihydro-benzoxazol-6-yl)propyl]piperazine-1-carboxylate |
| "A36" | 3-Dimethylaminobenzyl 4-[3-oxo-3-(2-oxo-2,3-dihydro-benzoxazol-6-yl)propyl]piperazine-1-carboxylate |
| "A37" | 4-Butoxybenzyl 4-[3-oxo-3-(2-oxo-2,3-dihydrobenzoxazol-6-yl)propyl]piperazine-1-carboxylate |
| "A38" | 4-Methoxybenzyl 4-[3-oxo-3-(2-oxo-2,3-dihydrobenzoxazol-6-yl)propyl]piperazine-1-carboxylate |
| "A39" | 4-Methoxycarbonylbenzyl 4-[3-oxo-3-(2-oxo-2,3-dihydro-benzoxazol-6-yl)propyl]piperazine-1-carboxylate |
| "A40" | 4-Trifluoromethylsulfanylbenzyl 4-[3-oxo-3-(2-oxo-2,3-dihydrobenzoxazol-6-yl)propyl]piperazine-1-carboxylate |
| "A41" | 4-Isopropylbenzyl 4-[3-oxo-3-(2-oxo-2,3-dihydrobenzoxazol-6-yl)propyl]piperazine-1-carboxylate |
| "A43" | 4-Chlorobenzyl 4-[3-(5-methyl-2-oxo-2,3-dihydrobenzoxazol-6-yl)-3-oxopropyl]piperazine-1-carboxylate |
| "A45" | 3,4-Dichlorobenzyl 4-[3-oxo-3-(2-oxo-2,3-dihydro-benzoxazol-6-yl)propyl]piperazine-1-carboxylate |
| "A46" | 2-(4-Fluorophenyl)ethyl 4-[3-oxo-3-(2-oxo-2,3-dihydro-benzoxazol-6-yl)propyl]piperazine-1-carboxylate |

| Compound No. | Name and/or structure |
|---|---|
| "A47" | Chroman-4-yl 4-[3-oxo-3-(2-oxo-2,3-dihydrobenzoxazol-6-yl)propyl]piperazine-1-carboxylate |
| "A48" | 3-Chlorobenzyl 4-[3-oxo-3-(2-oxo-2,3-dihydrobenzoxazol-6-yl)propyl]piperazine-1-carboxylate |
| "A49" | 3,5-Dichlorobenzyl 4-[3-oxo-3-(2-oxo-2,3-dihydro-benzoxazol-6-yl)propyl]piperazine-1-carboxylate |
| "A50" | 4-Trifluoromethylbenzyl 4-[3-oxo-3-(2-oxo-2,3-dihydro-benzoxazol-6-yl)propyl]piperazine-1-carboxylate |
| "A51" | 2-Fluoro-5-trifluoromethylbenzyl 4-[3-oxo-3-(2-oxo-2,3-dihydrobenzoxazol-6-yl)propyl]piperazine-1-carboxylate |
| "A52" | 6-Bromopyridin-2-ylmethyl 4-[3-oxo-3-(2-oxo-2,3-dihydro-benzoxazol-6-yl)propyl]piperazine-1-carboxylate |
| "A53" | 2-Fluoro-4-trifluoromethylbenzyl 4-[3-oxo-3-(2-oxo-2,3-dihydrobenzoxazol-6-yl)propyl]piperazine-1-carboxylate |
| "A54" | 4-Chloropyridin-2-ylmethyl 4-[3-oxo-3-(2-oxo-2,3-dihydro-benzoxazol-6-yl)propyl]piperazine-1-carboxylate |
| "A55" | 4-Fluorobenzyl 4-[3-oxo-3-(2-oxo-2,3-dihydrobenzoxazol-6-yl)propyl]piperazine-1-carboxylate |
| "A56" | 4-Methyl-3-nitrobenzyl 4-[3-oxo-3-(2-oxo-2,3-dihydro-benzoxazol-6-yl)propyl]piperazine-1-carboxylate |
| "A57" | Naphthalen-2-ylmethyl 4-[3-oxo-3-(2-oxo-2,3-dihydro-benzoxazol-6-yl)propyl]piperazine-1-carboxylate |

-continued

| Compound No. | Name and/or structure |
| --- | --- |
| "A58" | N-(4-tert-Butylbenzyl)-4-[3-oxo-3-(2-oxo-2,3-dihydrobenzoxazol-6-yl)propyl]piperazine-1-carboxamide |

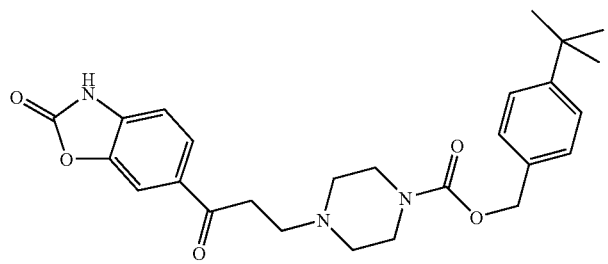 [SMILES: CC(C)(C)c1ccc(COC(=O)N2CCN(CCC(=O)c3ccc4[nH]c(=O)oc4c3)CC2)cc1]

| | |
| --- | --- |
| "A59" | N-(4-Chloro-3-trifluoromethylbenzyl)-4-[3-oxo-3-(2-oxo-2,3-dihydrobenzoxazol-6-yl)propyl]piperazine-1-carboxamide |
| "A60" | N-(4-Cyanobenzyl)-4-[3-oxo-3-(2-oxo-2,3-dihydro-benzoxazol-6-yl)propyl]piperazine-1-carboxamide |
| "A61" | 2-(4-Bromophenyl)ethyl 4-[3-oxo-3-(2-oxo-2,3-dihydro-benzoxazol-6-yl)propyl]piperazine-1-carboxylate |
| "A62" | Indan-2-yl 4-[3-oxo-3-(2-oxo-2,3-dihydrobenzoxazol-6-yl)-propyl]piperazine-1-carboxylate |
| "A63" | 2-(4-Methoxyphenyl)ethyl 4-[3-oxo-3-(2-oxo-2,3-dihydro-benzoxazol-6-yl)propyl]piperazine-1-carboxylate |
| "A64" | Phenethyl 4-[3-oxo-3-(2-oxo-2,3-dihydrobenzoxazol-6-yl)-propyl]piperazine-1-carboxylate |
| "A65" | 6-(3-{4-[2-(4-Chlorophenyl)acetyl]piperazin-1-yl}propionyl)-3H-benzoxazol-2-one |

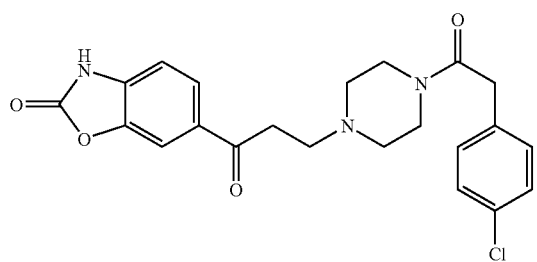 [SMILES: O=C(CCN1CCN(C(=O)Cc2ccc(Cl)cc2)CC1)c1ccc2[nH]c(=O)oc2c1]

| | |
| --- | --- |
| "A67" | 4-Styrylbenzyl 4-[3-oxo-3-(2-oxo-2,3-dihydrobenzoxazol-6-yl)propyl]piperazine-1-carboxylate |

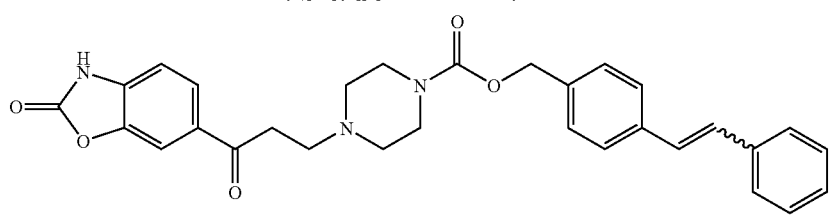

| | |
| --- | --- |
| "A68" | 4-Acetylaminobenzyl 4-[3-oxo-3-(2-oxo-2,3-dihydro-benzoxazol-6-yl)propyl]piperazine-1-carboxylate |
| "A69" | N-(4-Chlorobenzyl)-4-[3-oxo-3-(2-oxo-2,3-dihydro-benzoxazol-6-yl)propyl]piperazine-1-carboxamide |
| "A70" | 4-Methylsulfanylbenzyl 4-[3-oxo-3-(2-oxo-2,3-dihydro-benzoxazol-6-yl)propyl]piperazine-1-carboxylate |

| Compound No. | Name and/or structure |
|---|---|
| "A71" | Benzo-1,3-dioxol-5-ylmethyl 4-[3-oxo-3-(2-oxo-2,3-dihydro-benzoxazol-6-yl)propyl]piperazine-1-carboxylate 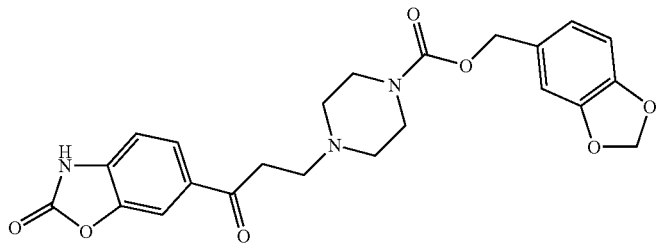 [SMILES: O=C(CCN1CCN(C(=O)OCc2ccc3c(c2)OCO3)CC1)c1ccc2[nH]c(=O)oc2c1] |
| "A72" | 4-Trifluoromethoxybenzyl 4-[3-oxo-3-(2-oxo-2,3-dihydro-benzoxazol-6-yl)propyl]piperazine-1-carboxylate |
| "A75" | Ethyl 2-{4-[3-oxo-3-(2-oxo-2,3-dihydrobenzoxazol-6-yl)-propyl]piperazin-1-yl}-4-phenylbutyrate 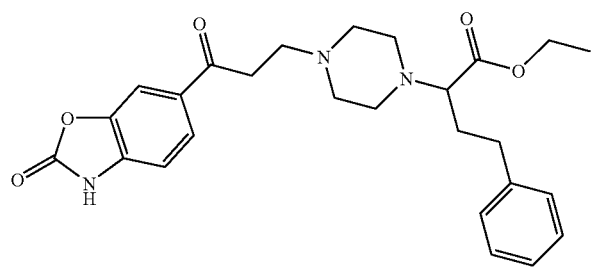 [SMILES: CCOC(=O)C(CCc1ccccc1)N1CCN(CCC(=O)c2ccc3[nH]c(=O)oc3c2)CC1] |
| "A77" | 4-[2-(4-Chlorophenoxy)acetyl]-1,1-bis[3-oxo-3-(2-oxo-2,3-dihydrobenzoxazol-6-yl)propyl]piperazin-1-ium 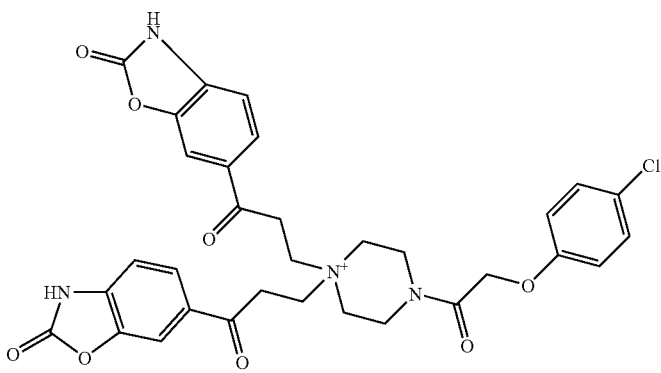 [SMILES: O=C(CC[N+]1(CCC(=O)c2ccc3[nH]c(=O)oc3c2)CCN(C(=O)COc2ccc(Cl)cc2)CC1)c1ccc2[nH]c(=O)oc2c1] |
| "A78" | 2-{4-[3-Oxo-3-(2-oxo-2,3-dihydrobenzoxazol-6-yl)propyl]-piperazin-1-yl}-N-pyridin-2-ylacetamide 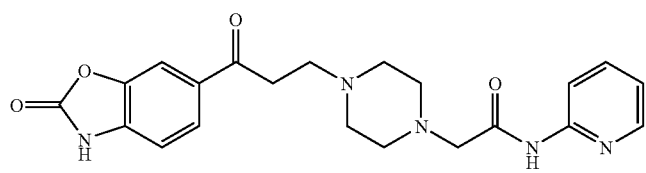 [SMILES: O=C(CN1CCN(CCC(=O)c2ccc3[nH]c(=O)oc3c2)CC1)Nc1ccccn1] |

| Compound No. | Name and/or structure |
|---|---|
| "A79" | 6-{3-[4-(2-Oxo-2-pyrrolidin-1-ylethyl)piperazin-1-yl]-propionyl}-3H-benzoxazol-2-one |
| "A80" | 6-(3-{4-[3-(2,4-Dichlorophenyl)propionyl]piperazin-1-yl}-propionyl)-3H-benzoxazol-2-one |
| "A81" | 6-(3-{4-[5-(3-Trifluoromethylphenyl)-2H-pyrazole-3-carbonyl]piperazin-1-yl}propionyl)-3H-benzoxazol-2-one |
| "A83" | 6-{3-[4-(2-Dimethylamino-3-phenylpropionyl)piperazin-1-yl]-propionyl}-3H-benzoxazol-2-one |
| "A84" | tert-Butyl ((S)-1-(4-chlorobenzyl)-2-oxo-2-{4-[3-oxo-3-(2-oxo-2,3-dihydrobenzoxazol-6-yl)propyl]piperazin-1-yl}ethyl)-carbamate |

-continued

| Compound No. | Name and/or structure |
|---|---|
| "A85" | 6-(3-{4-[(S)-2-Amino-3-(4-chlorophenyl)propionyl]piperazin-1-yl}propionyl)-3H-benzoxazol-2-one |
| "A86" | 5-Bromopyridin-3-ylmethyl 4-[3-oxo-3-(2-oxo-2,3-dihydro-benzoxazol-6-yl)propyl]piperazine-1-carboxylate |
| "A87" | Pyridin-2-ylmethyl 4-[3-oxo-3-(2-oxo-2,3-dihydrobenzoxazol-6-yl)propyl]piperazine-1-carboxylate |
| "A88" | 5-(4-Fluorophenyl)pyridin-3-ylmethyl 4-[3-oxo-3-(2-oxo-2,3-dihydrobenzoxazol-6-yl)propyl]piperazine-1-carboxylate |
| "A89" | Pyridin-3-ylmethyl 4-[3-oxo-3-(2-oxo-2,3-dihydrobenzoxazol-6-yl)propyl]piperazine-1-carboxylate |
| "A90" | 6-Chloropyridin-3-ylmethyl 4-[3-oxo-3-(2-oxo-2,3-dihydro-benzoxazol-6-yl)propyl]piperazine-1-carboxylate |
| "A91" | 2-Chloropyridin-4-ylmethyl 4-[3-oxo-3-(2-oxo-2,3-dihydro-benzoxazol-6-yl)propyl]piperazine-1-carboxylate |
| "A92" | N-(3,5-Dichlorobenzyl)-4-[3-oxo-3-(2-oxo-2,3-dihydro-benzoxazol-6-yl)propyl]piperazine-1-carboxamide |
| "A93" | 2-Trifluoromethoxybenzyl 4-[3-oxo-3-(2-oxo-2,3-dihydro-benzoxazol-6-yl)propyl]piperazine-1-carboxylate |
| "A94" | 3,4,5-Trimethoxybenzyl 4-[3-oxo-3-(2-oxo-2,3-dihydro-benzoxazol-6-yl)propyl]piperazine-1-carboxylate |
| "A95" | 3-Trifluoromethylsulfanylbenzyl 4-[3-oxo-3-(2-oxo-2,3-dihydrobenzoxazol-6-yl)propyl]piperazine-1-carboxylate |
| "A96" | Furan-2-ylmethyl 4-[3-oxo-3-(2-oxo-2,3-dihydrobenzoxazol-6-yl)propyl]piperazine-1-carboxylate |

-continued

| Compound No. | Name and/or structure |
|---|---|
| "A97" | 6-{3-[4-(2-Phenylethylsulfonyl)piperazin-1-yl]propionyl}-3H-benzoxazol-2-one |
| "A98" | 6-{3-[4-((E)-2-Phenylethenesulfonyl)piperazin-1-yl]-propionyl}-3H-benzoxazol-2-one |
| "A99" | 6-{3-[4-((E)-2-Methyl-3-phenylacryloyl)piperazin-1-yl]-propionyl}-3H-benzoxazol-2-one |
| "A100" | 6-(3-{4-[(E)-(3-Phenylacryloyl)]piperazin-1-yl}propionyl)-3H-benzoxazol-2-one |
| "A101" | N-Methyl-2-{4-[3-oxo-3-(2-oxo-2,3-dihydrobenzoxazol-6-yl)-propyl]piperazin-1-yl}-N-phenylacetamide |
| "A102" | 3,5-Bistrifluoromethylbenzyl 4-[3-oxo-3-(2-oxo-2,3-dihydro-benzoxazol-6-yl)propyl]piperazine-1-carboxylate |
| "A103" | 3-Chloro-5-trifluoromethylbenzyl 4-[3-oxo-3-(2-oxo-2,3-dihydrobenzoxazol-6-yl)propyl]piperazine-1-carboxylate |
| "A104" | 3,5-Dimethoxybenzyl 4-[3-oxo-3-(2-oxo-2,3-dihydro-benzoxazol-6-yl)propyl]piperazine-1-carboxylate |
| "A105" | 3,5-Dimethylbenzyl 4-[3-oxo-3-(2-oxo-2,3-dihydro-benzoxazol-6-yl)propyl]piperazine-1-carboxylate |
| "A106" | 3,5-Dibromobenzyl 4-[3-oxo-3-(2-oxo-2,3-dihydro-benzoxazol-6-yl)propyl]piperazine-1-carboxylate |

| Compound No. | Name and/or structure |
|---|---|
| "A107" | 3-Fluoro-5-trifluoromethylbenzyl 4-[3-oxo-3-(2-oxo-2,3-dihydrobenzoxazol-6-yl)propyl]piperazine-1-carboxylate |
| "A108" | 3-Chloro-5-fluorobenzyl 4-[3-oxo-3-(2-oxo-2,3-dihydrobenzoxazol-6-yl)propyl]piperazine-1-carboxylate |
| "A109" | 3-Trifluoromethylbenzyl 4-[3-oxo-3-(2-oxo-2,3-dihydrobenzoxazol-6-yl)propyl]piperazine-1-carboxylate |
| "A110" | 3,5-Difluorobenzyl 4-[3-oxo-3-(2-oxo-2,3-dihydrobenzoxazol-6-yl)propyl]piperazine-1-carboxylate |
| "A111" | 2-Fluorobenzyl 4-[3-oxo-3-(2-oxo-2,3-dihydrobenzoxazol-6-yl)propyl]piperazine-1-carboxylate |
| "A112" | 3-(Morpholine-4-sulfonyl)benzyl 4-[3-oxo-3-(2-oxo-2,3-dihydrobenzoxazol-6-yl)propyl]piperazine-1-carboxylate 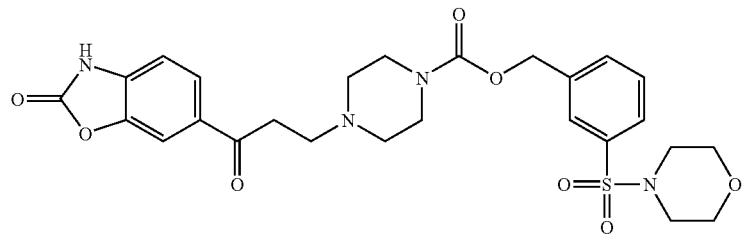 [SMILES: O=C(CCN1CCN(C(=O)OCc2cccc(S(=O)(=O)N3CCOCC3)c2)CC1)c1ccc2[nH]c(=O)oc2c1] |
| "A113" | 4-Cyanobenzyl 4-[3-oxo-3-(2-oxo-2,3-dihydrobenzoxazol-6-yl)propyl]piperazine-1-carboxylate |
| "A114" | 4-Chlorobenzyl 4-[3-oxo-3-(2-oxo-3-prop-2-ynyl-2,3-dihydrobenzoxazol-6-yl)propyl]piperazine-1-carboxylate 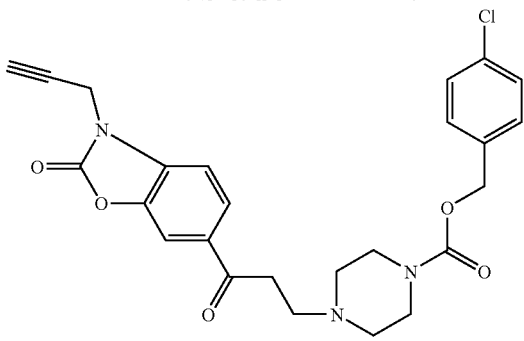 [SMILES: C#CCn1c(=O)oc2cc(C(=O)CCN3CCN(C(=O)OCc4ccc(Cl)cc4)CC3)ccc21] |
| "A115" | 6-{3-[4-(5-Chloroindane-2-carbonyl)piperazin-1-yl]propionyl}-3H-benzoxazol-2-one 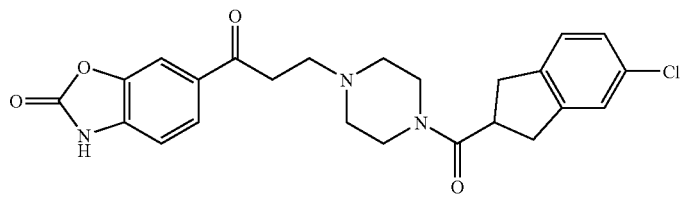 [SMILES: O=C(CCN1CCN(C(=O)C2Cc3ccc(Cl)cc3C2)CC1)c1ccc2[nH]c(=O)oc2c1] |
| "A116" | 6-{3-[4-(4-Chlorophenylmethanesulfonyl)piperazin-1-yl]-propionyl}-3H-benzoxazol-2-one 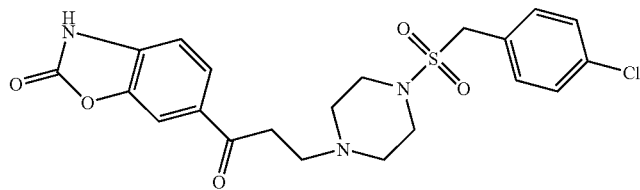 [SMILES: O=C(CCN1CCN(S(=O)(=O)Cc2ccc(Cl)cc2)CC1)c1ccc2[nH]c(=O)oc2c1] |

-continued

| Compound No. | Name and/or structure |
|---|---|
| "A117" | 4-(2-Oxo-5-{4-[3-oxo-3-(2-oxo-2,3-dihydrobenzoxazol-6-yl)-propyl]piperazin-1-ylmethyl}oxazolidin-3-yl)benzonitrile |
| "A118" | 6-(3-{4-[2-Aminomethyl-3-(4-chlorophenyl)propionyl]-piperazin-1-yl}propionyl)-3H-benzoxazol-2-one |
| "A119" | 4-(2-Dimethylaminoethoxy)benzyl 4-[3-oxo-3-(2-oxo-2,3-dihydrobenzoxazol-6-yl)propyl]piperazine-1-carboxylate |
| "A120" | 2,4,6-Trimethylbenzyl 4-[3-oxo-3-(2-oxo-2,3-dihydro-benzoxazol-6-yl)propyl]piperazine-1-carboxylate |
| "A121" | 6-{3-[4-(4-Chlorobenzenesulfonyl)piperazin-1-yl]propionyl}-3H-benzoxazol-2-one |
| "A122" | 6-(3-{4-[(E)-2-(4-Chlorophenyl)ethenesulfonyl]piperazin-1-yl}propionyl)-3H-benzoxazol-2-one |
| "A124" | 3-Cyanobenzyl 4-[3-oxo-3-(2-oxo-2,3-dihydrobenzoxazol-6-yl)propyl]piperazine-1-carboxylate |
| "A125" | 6-(3-{4-[2-(3,5-Difluorophenyl)acetyl]piperazin-1-yl}-propionyl)-3H-benzoxazol-2-one |

| Compound No. | Name and/or structure |
|---|---|
| "A126" | 6-{3-[4-(5-Methyl-1H-indole-2-carbonyl)piperazin-1-yl]-propionyl}-3H-benzoxazol-2-one |
| "A127" | 6-{3-[4-(5-Chloro-1H-indole-2-carbonyl)piperazin-1-yl]-propionyl}-3H-benzoxazol-2-one |
| "A128" | 6-{3-[4-(6-Chlorochroman-3-carbonyl)piperazin-1-yl]-propionyl}-3H-benzoxazol-2-one |
| "A129" | 6-{3-[4-(4'-Methylbiphenyl-2-carbonyl)piperazin-1-yl]-propionyl}-3H-benzoxazol-2-one |
| "A130" | 6-(3-{4-[3-(4-Chlorophenoxy)propionyl]piperazin-1-yl}-propionyl)-3H-benzoxazol-2-one | or or a pharmaceutically acceptable tautomer, salt or stereoisomer thereof.

16. A compound, which is one of the following compounds

| Compound No. | Name and/or structure |
|---|---|
| "B1" | 6-(3-{4-[3-(3,4-Dichlorophenyl)propionyl]piperazin-1-yl}-propionyl)-3H-benzoxazol-2-one |
| "B2" | 6-(3-{4-[3-(3-Trifluoromethylphenyl)propionyl]piperazin-1-yl}-propionyl)-3H-benzoxazol-2-one |
| "B3" | 6-{3-[4-((S)-2-Hydroxy-3-phenylpropionyl)piperazin-1-yl]-propionyl}-3H-benzoxazol-2-one |
| "B4" | 6-{3-[4-(2-Phenylcyclopropanecarbonyl)piperazin-1-yl]-propionyl}-3H-benzoxazol-2-one |

| Compound No. | Name and/or structure |
|---|---|
| "B8" | 6-(3-{4-[(E)-3-(3-Trifluoromethylphenyl)acryloyl]piperazin-1-yl}propionyl)-3H-benzoxazol-2-one |
| "B9" | 6-{3-[4-(4'-Methylbiphenyl-4-carbonyl)piperazin-1-yl]-propionyl}-3H-benzoxazol-2-one |
| "B10" | 6-{3-[4-(5-Trifluoromethyl-1H-benzoimidazole-2-carbonyl)-piperazin-1-yl]propionyl}-3H-benzoxazol-2-one |
| "B11" | 6-(3-{4-[2-(5-Chloro-3-methylbenzo[b]thiophen-2-yl)acetyl]-piperazin-1-yl}propionyl)-3H-benzoxazol-2-one |
| "B12" | 6-(3-{4-[2-(3,5-Bistrifluoromethylphenyl)acetyl]piperazin-1-yl}propionyl)-3H-benzoxazol-2-one |
| "B13" | 1-(3,5-Dichlorophenyl)-4-{4-[3-oxo-3-(2-oxo-2,3-dihydro-benzoxazol-6-yl)propyl]piperazin-1-yl}butane-1,4-dione |
| "B14" | 5,6-Dichloro-2-(2-oxo-2-{4-[3-oxo-3-(2-oxo-2,3-dihydro-benzoxazol-6-yl)propyl]piperazin-1-yl}ethyl)isoindole-1,3-dione |
| "B15" | 6-(3-{4-[4-Methyl-2-(4-trifluoromethylphenyl)thiazole-5-carbonyl]piperazin-1-yl}propionyl)-3H-benzoxazol-2-one |
| "B16" | 6-(3-{4-[3-(4-Trifluoromethylphenyl)thiophene-2-carbonyl]-piperazin-1-yl}propionyl)-3H-benzoxazol-2-one |
| "B17" | 2-(2-Dimethylaminoethoxy)benzyl 4-[3-oxo-3-(2-oxo-2,3-dihydrobenzoxazol-6-yl)propyl]piperazine-1-carboxylate |
| "B19" | 6-(3-{4-[2-(4-Chlorophenylamino)acetyl]piperazin-1-yl}-propionyl)-3H-benzoxazol-2-one |
| "B20" | 4-Chlorobenzyl 4-[2-methyl-3-oxo-3-(2-oxo-2,3-dihydro-benzoxazol-6-yl)propyl]piperazine-1-carboxylate |
| "B21" | 3,5-Dichlorobenzyl 4-[2-oxo-2-(2-oxo-2,3-dihydro-benzoxazol-6-yl)ethyl]piperazine-1-carboxylate |
| "B22" | 6-(2-{4-[3-(4-Chlorophenoxy)propionyl]piperazin-1-yl}acetyl)-3H-benzoxazol-2-one |
| "B23" | 5-Chloro-2-methoxybenzyl 4-[3-oxo-3-(2-oxo-2,3-dihydro-benzoxazol-6-yl)propyl]piperazine-1-carboxylate |
| "B24" | 4'-Trifluoromethylbiphenyl-2-ylmethyl 4-[3-oxo-3-(2-oxo-2,3-dihydrobenzoxazol-6-yl)propyl]piperazine-1-carboxylate |
| "B25" | 6-{3-[4-(4'-Methylbiphenyl-3-carbonyl)piperazin-1-yl]-propionyl}-3H-benzoxazol-2-one |
| "B26" | 4-(2-Oxo-5-{4-[3-oxo-3-(2-oxo-2,3-dihydrobenzoxazol-6-yl)-propyl]piperazine-1-carbonyl}oxazolidin-3-yl)benzonitrile |
| "B27" | 6-(3-{4-[2-(3,4-Dichlorophenyl)thiazolidine-4-carbonyl]-piperazin-1-yl}propionyl)-3H-benzoxazol-2-one |
| "B28" | 4-(2-Oxo-4-{4-[3-oxo-3-(2-oxo-2,3-dihydrobenzoxazol-6-yl)-propyl]piperazine-1-carbonyl}pyrrolidin-1-yl)benzonitrile |
| "B29" | 6-(3-{4-[5-(4-Chlorophenyl)furan-2-carbonyl]piperazin-1-yl}-propionyl)-3H-benzoxazol-2-one |
| "B30" | 6-(3-{4-[4-(3,4-Dichlorophenyl)-1H-pyrrole-2-carbonyl]-piperazin-1-yl}propionyl)-3H-benzoxazol-2-one |
| "B31" | 6-(3-{4-[4-Methyl-2-(4-trifluoromethylphenyl)thiazole-5-carbonyl]piperazin-1-yl}propionyl)-3H-benzoxazol-2-one |
| "B32" | Tetrahydrofuran-2-ylmethyl 4-[3-oxo-3-(2-oxo-2,3-dihydro-benzoxazol-6-yl)propyl]piperazine-1-carboxylate |
| "B33" | N-(Tetrahydrofuran-2-ylmethyl)-4-[3-oxo-3-(2-oxo-2,3-dihydrobenzoxazol-6-yl)propyl]piperazine-1-carboxamide |
| "B34" | 6-{3-[4-[3-(3,5-Difluorophenyl)propionyl]piperazin-1-yl]-propionyl)-3H-benzoxazol-2-one |
| "B35" | N-(9-Ethyl-9H-carbazol-3-yl)-4-[3-oxo-3-(2-oxo-2,3-dihydro-benzoxazol-6-yl)propyl]piperazine-1-carboxamide |
| "B36" | 1-Methyl-1H-indol-6-ylmethyl 4-[3-oxo-3-(2-oxo-2,3-dihydro-benzoxazol-6-yl)propyl]piperazine-1-carboxylate |
| "B37" | 6-{3-[4-(3-1H-Indol-3-ylpropionyl)piperazin-1-yl]propionyl}-3H-benzoxazol-2-one |
| "B38" | 6-{3-[4-(3-Indol-1-ylpropionyl)piperazin-1-yl]propionyl}-3H-benzoxazol-2-one |
| "B39" | 6-(3-{4-[3-(1-Methyl-1H-pyrazol-4-yl)propionyl]piperazin-1-yl}propionyl)-3H-benzoxazol-2-one |
| "B40" | tert-Butyl ((R)-1-(4-chlorobenzyl)-2-oxo-2-{4-[3-oxo-3-(2-oxo-2,3-dihydrobenzoxazol-6-yl)propyl]piperazin-1-yl}ethyl)-methylcarbamate |
| "B41" | O-(4-Chlorobenzyl) 4-[3-oxo-3-(2-oxo-2,3-dihydro-benzoxazol-6-yl)propyl]piperazine-1-carbothiolate |
| "B42" | 9H-Fluoren-9-ylmethyl ((S)-1-(4-tert-butoxybenzyl)-2-oxo-2-{4-[3-oxo-3-(2-oxo-2,3-dihydrobenzoxazol-6-yl)propyl]-piperazin-1-yl}ethyl)methylcarbamate |
| "B43" | 6-{3-[4-(5-Chloro-1-methyl-1H-indole-2-carbonyl)piperazin-1-yl]propionyl}-3H-benzoxazol-2-one |
| "B44" | 6-(3-{4-[3-(4-Dimethylaminophenyl)propionyl]piperazin-1-yl}-propionyl)-3H-benzoxazol-2-one |

| Compound No. | Name and/or structure |
|---|---|
| "B45" | 2-Methyl-5-phenyl-2H-pyrazol-3-ylmethyl 4-[3-oxo-3-(2-oxo-2,3-dihydrobenzoxazol-6-yl)propyl]piperazine-1-carboxylate |
| "B47" | 4-Chlorobenzyl 4-[2-(2-oxo-2,3-dihydrobenzoxazole-6-sulfinyl)ethyl]piperazine-1-carboxylate |
| "B48" | 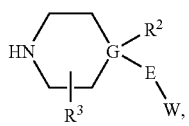 |
| "B49" | 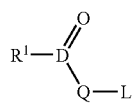 |
| "B51" | 3,5-Dichlorobenzyl 4-[2-(2-oxo-2,3-dihydrobenzoxazole-6-sulfinyl)ethyl]piperazine-1-carboxylate |
| "B54" | 6-(3-{4-[5-(4-Chlorophenyl)-2H-pyrazole-3-carbonyl]-piperazin-1-yl}propionyl)-3H-benzoxazol-2-one | or a pharmaceutically acceptable tautomer, salt or stereoisomer thereof.

17. A process for preparing a compound of formula I according to claim 1, or a pharmaceutically acceptable tautomer, salt or stereoisomer thereof, comprising a) reacting a compound of formula II

II in which $R^2$, $R^3$, G, E and W have the meanings indicated for the compound of formula I, with a compound of formula III $$R^1-D\overset{O}{\underset{Q-L}{\|}}$$

III in which $R^1$, D and Q have the meanings indicated for the compound of formula I, and L denotes Cl, Br, I or a free or reactively functionally modified OH group, or b) reacting a compound of formula IV

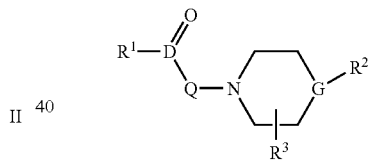

IV in which $R^1$, $R^2$, $R^3$, D and Q have the meanings indicated for the compound of formula I and G=N with a compound of formula V

L-E-W    V in which

E and W have the meanings indicated for the compound of formula I, and

L denotes Cl, Br, I or a free or reactively functionally modified OH group, and/or converting a base or acid of a compound of formula I into one of its salts.

18. A pharmaceutical composition comprising at least one compound of formula I according to claim 1, or a pharmaceutically acceptable tautomer, salt or stereoisomer thereof, and one or more pharmaceutically acceptable excipients and/or adjuvants.

19. A method for treating a tumour that originates from monocytic leukaemia, lung adenocarcinoma, small-cell lung carcinoma, pancreatic cancer, glioblastoma, breast carcinoma, colocarcinoma, acute myeloid leukaemia, chronic myeloid leukaemia, acute lymphatic leukaemia or chronic lymphatic leukaemia, comprising administering an effective amount of a compound according to claim 1, or a pharmaceutically acceptable tautomer, salt or stereoisomer thereof, to a subject in need thereof.

20. A method for treating a tumour that originates from monocytic leukaemia, lung adenocarcinoma, small-cell lung carcinoma, pancreatic cancer, glioblastoma, breast carcinoma, colocarcinoma, acute myeloid leukaemia, chronic myeloid leukaemia, acute lymphatic leukaemia or chronic lymphatic leukaemia, comprising administering an effective amount of a compound according to claim 15, or a pharmaceutically acceptable tautomer, salt or stereoisomer thereof, to a subject in need thereof.

21. A method for treating a tumour that originates from monocytic leukaemia, lung adenocarcinoma, small-cell lung carcinoma, pancreatic cancer, glioblastoma, breast carcinoma, colocarcinoma, acute myeloid leukaemia, chronic myeloid leukaemia, acute lymphatic leukaemia or chronic lymphatic leukaemia, comprising administering an effective amount of a compound according to claim 16, or a pharmaceutically acceptable tautomer, salt or stereoisomer thereof, to a subject in need thereof.

22. A method according to claim 19, where the tumour originates from monocytic leukaemia, lung adenocarcinoma, small-cell lung carcinoma, pancreatic cancer, glioblastoma, breast carcinoma or colocarcinoma.

23. A method for treating a tumour that originates from monocytic leukaemia, lung adenocarcinoma, small-cell lung carcinoma, pancreatic cancer, glioblastoma, breast carcinoma, colocarcinoma, acute myeloid leukaemia, chronic myeloid leukaemia, acute lymphatic leukaemia or chronic lymphatic leukaemia, comprising administering an effective amount of a compound according to claim 14, or a pharmaceutically acceptable tautomer, salt or stereoisomer thereof, to a subject in need thereof.

24. A method according to claim 19, where the tumour originates from acute myeloid leukaemia, chronic myeloid leukaemia, acute lymphatic leukaemia and/or chronic lymphatic leukaemia.

25. A method according to claim 19, wherein the compound of formula I or a pharmaceutically acceptable salt thereof is administered in combination with radiotherapy and a compound selected from the group consisting of 1) oestrogen receptor modulator, 2) androgen receptor modulator, 3) retinoid receptor modulator, 4) cytotoxic agent, 5) antiproliferative agent, 6) prenyl-protein transferase inhibitor, 7) HMG-CoA reductase inhibitor, 8) HIV protease inhibitor, 9) reverse transcriptase inhibitor and 10) angiogenesis inhibitors.

26. A compound according to claim 1 in which
E denotes $COO(CR_2)_n$, $COO(CRR^4)$, $CO(CR_2)_mO$, $CONH(CR_2)_n$, $C(=S)NH(CR_2)_n$, $S(O)_qNH(CR_2)_n$, $S(O)_q(CR_2)_n$, $CO(CR_2)_mO(CR_2)_n$, $CO(CR_2)_mNH(CR_2)_n$, $CO(CH_2)_nCO$, $COCHR^6CHR^7$, $C(=S)O(CR_2)_n$, $CO(CRR^4)(CR_2)_n$, $COO(CRR^4)$, $(CRR^4)(CR_2)_n$, $S(O)_qCR=CR$, $COCR=CR$, $CONH(CR_2)_mCRR^4$ or $(CR_2)_mCONR$.

* * * * *

UNITED STATES PATENT AND TRADEMARK OFFICE
CERTIFICATE OF CORRECTION

PATENT NO. : 8,791,111 B2  Page 1 of 1
APPLICATION NO. : 12/681440
DATED : July 29, 2014
INVENTOR(S) : Kai Schiemann et al.

It is certified that error appears in the above-identified patent and that said Letters Patent is hereby corrected as shown below:

IN THE CLAIMS:

Columns 115 and 116, (Claim 15), last two lines, delete: ""A11" 6-(3-{4-[2-(4-Flourophenyl)ethyl]piperazin-1-yl}propionyl)-3H-benzoxazol-2-one"

Columns 125 and 126 (Claim 15), the formula of Compound "A58" reads as:

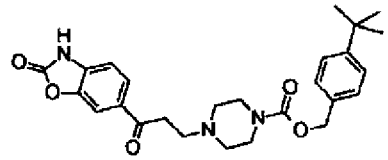

Should read as:

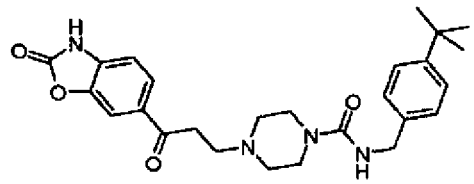

Signed and Sealed this
Tenth Day of February, 2015

Michelle K. Lee
*Deputy Director of the United States Patent and Trademark Office*